United States Patent
Lardizabal et al.

(10) Patent No.: US 6,492,509 B1
(45) Date of Patent: *Dec. 10, 2002

(54) FATTY ACYL-COA: FATTY ALCOHOL ACYLTRANSFERASES

(75) Inventors: Kathryn Dennis Lardizabal, Woodland, CA (US); James George Metz, Davis, CA (US); Michael W. Lassner, Davis, CA (US)

(73) Assignee: Calgene LLC, Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/205,815

(22) Filed: Dec. 4, 1998

Related U.S. Application Data

(63) Continuation-in-part of application No. 09/092,562, filed on Jun. 5, 1998, which is a continuation-in-part of application No. PCT/US98/11590, filed on Jun. 5, 1998, which is a continuation of application No. 08/265,047, filed on Jun. 23, 1994, now Pat. No. 5,679,881.
(60) Provisional application No. 60/048,651, filed on Jun. 5, 1997.

(51) Int. Cl.⁷ .............................................. C07H 21/04
(52) U.S. Cl. ..................................... 536/23.6; 536/23.2
(58) Field of Search ............................... 536/23.1, 23.2, 536/23.6

(56) References Cited

U.S. PATENT DOCUMENTS

| | | |
|---|---|---|
| 5,370,996 A | 12/1994 | Metz et al. |
| 5,403,918 A | 4/1995 | Metz |
| 5,411,879 A | 5/1995 | Pollard et al. |
| 5,420,034 A | 5/1995 | Kridl et al. |
| 5,445,947 A | 8/1995 | Metz et al. |
| 5,679,881 A | 10/1997 | Metz et al. |
| 5,723,747 A | 3/1998 | Lassner et al. |
| 5,728,412 A | 3/1998 | Fujii et al. |

FOREIGN PATENT DOCUMENTS

| | | |
|---|---|---|
| WO | WO 91/16421 | 10/1991 |
| WO | WO 92/14816 | 9/1992 |
| WO | WO 93/10241 | 5/1993 |
| WO | WO 95/15387 | 6/1995 |
| WO | WO 95/33055 | 12/1995 |
| WO | WO 98/55632 | 12/1998 |

OTHER PUBLICATIONS

Bork, "Go hunting in sequence databses but watch out for the traps", 1996, TIG, vol. 12 No. 10, pp. 425–427.*
Smith et al, The challenges of genome sequence annotation or "The devil is in the details", 1997, Nature Biotechnology vol. 15, pp. 1222–1223.*
Doerks, "Protein annotation: detecive work for function prediction",1998, TIG, vol. 14 No. 6 pp. 248–250.*
Broun et al, Catalytic Plasticity of Fatty Acid Modification Enzymes Underlying Chemical Diversity of Plant Lipids, 1998, Science vol. 282, pp. 1315–1317.*
Van de Loo et al, An oleate 12–hydroxylase from *Ricinus communis L.* is a fatyy acyl desaturase homolog, 1995, Proc. Nat. Acad. Sci. vol. 92, pp. 6743–6747.*
Brener, "Errors in genome annotation", 1999, vol. 15, No. 4 pp. 132–133.*
Zou et al., "The *Arabidopsis thaliana* TAG1 mutant has a mutation in a diacylglycerol acyltransferase gene" *The Plant Journal* 19(6):645–53 (1999).
Garver, "Partial Purification Characterization of Acyl–CoA: Alcohol Transacylase in Subcellular Organelles from Developing Jojoba Cotyledons (*Simmondsia Chinensis*)" Database XP002081026 (1991).
International Search Report, PCT/US99/28678 (1999).
Lardizabal et al., "Purification of a Jojoba Embryo Wax Synthase, Cloning of its cDNA, and Production of High Levels of Wax in Seeds in Transgenic Arabidopsis" *Plant Physiology* 122:645–55 (2000).
Metz et al., "Purification of a Jojoba Embryo Fatty Acyl–Coenzyme A Reductase and Expression of Its cDNA in High Erucic Acid Rapeseed" *Plant Physiology* 122:635–44 (2000).
Routaboul et al., "The TAGI locus of Arabidopsis encodes for a diacylglycerol acyltransferase" *Plant Physiol Biochem.* 37(11) 831–40 (1999).
Smith et al. "Obesity resistance and multiple mechanisms of triglyceride synthesis in mice lacking Dgat" *Nature* 25 (1) 87–90 (2000).
International Search Report, PCT/US98/11590 (1998).
Lassner, et al., "A Jojoba B–Ketoacyl–CoA Synthase cDNA Complements the Canola Fatty Acid Elongation Mutation in Transgenic Plants" *The Plant Cell* 8, 281–292 (1996).
Garver, et al., "A High–performance Liquid Chromatography–Based Radiometric Assay for Acyl–CoA: Alcohol Transacylase from Jojoba" *Analytical Biochemistry* 207, 335–340 (1992).
Shockey, et al., "Photoaffinity Labeling of Developing Jojoba Seed Microsomal Membranes with a Photoreactive Analog of Acyl–Coenzyme A (Acyl–CoA)" *Plant Physiology* 107, 155–160 (1995).

(List continued on next page.)

*Primary Examiner*—Elizabeth F. McElwain
(74) *Attorney, Agent, or Firm*—Arnold & Porter; Alissa M. Eagle

(57) ABSTRACT

By this invention, nucleic acid sequences encoding for fatty acyl-CoA: fatty alcohol acyltransferase (wax synthase) are provided, wherein wax synthase is active in the formation of a wax ester from fatty alcohol and fatty acyl-CoA substrates. Of special interest is are nucleic acid sequences obtainable from a jojoba embryo wax synthase having an apparent molecular mass of approximately 33 kD. Also considered are amino acid and nucleic acid sequences obtainable from wax synthase proteins and the use of such sequences to provide transgenic host cells capable of producing wax esters.

2 Claims, 24 Drawing Sheets

OTHER PUBLICATIONS

Wu, et al., "Studies of Biosynthesis of Waxes by Developing Jojoba Seed: III. Biosynthesis of Wax Esters from Acyl–CoA and Long Chain Alcohols" *Lipids* 16(12), 897–902 (1981).

Pollard, et al., "Studies on Biosynthesis of Waxes by Developing Jojoba Seed. II. The Demonstration of wax Biosynthesis by Cell–Free Homogenates" *Lipids* 14(7), 651–662 (1979).

Ohlrogge, et al., "Studies on Biosynthesis of Waxes on Developing Jojoba Seed Tissue" *Lipids* 13(3), 203–210 (1978).

Wildner, et al., "Abstract: Wax Ester Biosynthesis in *Euglena gracilis*" *The Southwest Consortium Fifth Annual Meeting,* Apr. 22–24, Las Cruces, New Mexico (1990).

Pushnik, et al., "Abstract: Characterization of the Biosynthetic Pathway for Formation of Liquid wax in Jojoba" *The Southwest Consortium Fourth Annual Meeting,* Feb. 7, Las Cruces, New Mexico (1989).

Kamisaka, et al., "Characterization of the Diacylglycerol Acyltransferase Activity in the Lipid Body Fraction from an Oleaginous Fungus" *Journal of Biochemistry* 116, 1295–1301 (1994).

Little, et al., "Abstract: Factors Affecting the Assay of Diacylglycerol Acyltransferase from Microspore–derived Cultures of *Brassica Napus L.* and Solubilization of the Enzyme" *National Plant Lipid Cooperative—Plant Lipid Symposium,* Jul. 29–31, Minneapolis, Minnesota (1993).

Kamisaka, et al., "Activation of Detergent–Solubilized Diacylglycerol Acyltransferase by Anionic Phospholipids" *Journal of Biochemistry* 119, 530–523 (1996).

Kamisaka, et al., "Purification and Characterization of Diacylglycerol Acyltransferase from the Lipid Body Fraction of an Oleaginous Fungus" *Journal of Biochemistry* 121, 1107–1114 (1997).

Kwanyuen, et al., "Subunit and Amino Acid Composition of Diacylglycerol Acyltransferase from Germinating Soybean Cotyledons" *Biochimica et Biophysica Acta* 1039, 67–72 (1990).

Kwanyuen, et al., "Isolation and Purification of Diacylglycerol Acyltransferase from Germinating Soybean Cotyledons" *Biochimica et Biophysica Acta* 877, 238–245 (1986).

Andersson, et al., "Purification of Diacylglycerol: Acyltransferase from Rat Liver to Near Homogeneity" *Journal of Lipid Research* 35, 535–545 (1994).

Kamisaka, et al., "Characterization of the Diacylglycerol Acyltransferase Activity in the Membrane Fraction from a Fungus" *Lipids* 28(7), 583–587 (1993).

Polokoff, et al., "Solubilization, Partial Purification and Characterization of Rat Liver Microsomal Diacylglycerol Acyltransferase" *Biochimica et Biophysica Acta* 618, 129–142 (1980).

Canevascini, et al., "Tissue–Specific Expression and Promoter Analysis of the Tobacco Itp1 Gene" *Plant Physiology* 112, 513–524 (1996).

Li, et al., "Arabidopsis Rho–related GTPases: Differential Gene Expression in Pollen and Polar Localization in Fission Yeast" *Plant Physiology* 118, 407–417 (1998).

Hamilton, et al., "A Monocot Pollen–Specific Promoter Contains Separable Pollen–Specific and Quantitative Elements" *Plant Molecular Biology* 38, 663–669 (1998).

Klein, et al., "Transformation of Microbes, Plants, and Animals by Particle Bombardment" *Bio/Technology* 10, 286–291 (1992).

Chopra, et al., "Metabolic Engineering of Plant Lipids" *Journal of Plant Biochemistry and Biotechnology* 5(2), 63–68 (1996).

Nakamura, Y. Et al., "*Arabidopsis thaliana* genomic DNA chromosome 5, P1 clone MTE17" EMBL Sequence Database, Jun. 19, 1998, XP002138250.

* cited by examiner

DNA SEQUENCE OF THE PCR PRODUCT FROM PRIMERS
WSPEP14-F1 AND WSPEP33-R2

GATGACCCCAAWSNAAYGACCATGAGAAAAACAAGAGAACTCTGAGTTTTGAGTGGCGT
AAAGTTGTTCTTTTGTTGCTAAGTTGGTGTTTTTGCGGTATTTAAAGATTTAT
GAGTTTAGAAAAGATTTGCCTCATTTTGTGATCTCGGTGCTTTACTGTTTTCACTTC
TATCTCGGGACGGAGATCACCTTAGCAGCGCAGTCATAGCGCGAGCCACGCTA
GGGTTAGACCTATACCCCAGTTCAACGAGCCATTAGCCACCTCGCTGCAAGAC
TTCTGGGGCGCAGGTGGAACCTCATGGTCAGACATCTTGGGTTGACAACATAC
CAGCCCTGTCCGGCGTCCTGGCCGTTGGGGTCAGGCTGCAGGTCATGAAGTGTTTTCTTNTAC
GCAATGTGTTGGTGGGCGAGGCCCTCGTGGGAGGTGACGGGGTTCTTTGTBTTGCATGGGGTT
TTAACTCGCGCGAGGCCGTGGAGATGGTGGTGAAGAAGGCGGTTTCAGGCAAGGTGCGGCTGCGC
TGCACAGCCGTGGAGATGGTGGTGAAGAAGGCGGTTTCGTGATGGTGACTGGAGGGTGCTGCG
CGGGAGGTGTCAGGGCGCTGAGGCATGGGGGGTAGATTTGAAGACCATTGATGAGTATCCT
TTTTGCCGCAGCTGTGAGGCATGGGGGGTAGATTTGAAGACCATTGATGAGTATCCT
GTCATGTTYAAYTAYACCCAGAAA

*FIG. 3A*

DNA SEQUENCE OF THE WAX cDNA INFERRED FROM 5' AND 3' RACE PRODUCTS.

```
GTCTCCATTACAATGGAGGTGGAGAAGGAGCTAAAGACCTTCTCAGAGGTATGGATC
TCCGCCATAGCCGCCGCCTGCTACTGCCGTTCGTCGTCCCCGCCGTTGCCCCTCACGGC
GGCGCTCTCCGCCCTCCTCCTCCTCCCCGTCGTCCTCCTCCTCTCATTTCCTCCCC
CTCCGCCTCTCCTCCTTCCACCTCGGCGGCCCACCGCCTTGTATCTCGTCTGGCTT
GCCAACTTCAAGCTCCTTCTCTTCGCCTTCATCTTGGCCTTTATCTAACCCCTCT
CTCTCTCCTTCACTTCATCTCCACCACCCTCCCCCATCAAGTTCAGAGATGAC
CCATCTAATGATCATGAGAAAAACAAGAGAACTCGAGTTTTGAGTGGCGTAAAGTT
GTTCTTTTTGTTGCTAAGTTGGTGTTTGTGATCTCGGGTATTTAAAGATTTATGAGTTT
AGAAAAGATTTGCCTCACCTTAGCAGCAAGCGCAGTCATAGCTCGAGCCACGCTAGGGTTA
GGGACGGAGATCACCCTTAGCAGCAAGCGCAGTCATAGCTCGAGCCACGCTAGGGTTA
GACCTATACCCCCAGTTCAACGAGCCATTAGCCACCTCGCTGCAAGACTTCTGG
GGGCGCAGGTGGAACCTCATGGTGTCAGACATCTTGGGGTTGACAACATACCAGCCT
GTCCGGCGTGTCCTTCACGGTGTCGGGCGAGGTGAAGTGCATGAAGTGTTTTCTTCTTAACT
TTGGTGGCGTTCACGGTGTCGGGCGAGGTGAAGTGCATGAAGTGTTTTCTTCTTAACT
CGCGCGAGGCCCTCGTGGAGGTGACGCGGGGTTTCGTGATGGTGCAAGGTGCGGCTGCCGGGAG
GCCGTGGAGATGGTGGTGAAGAAGGCGGTTCGTGATGGTGACGAAGGTGCGGCCGGGAG
GTGTCAGGGCGCTGAGGCATGGGGGTAGATTGAAGACCATTGATGAGTATCCTGTCATG
CCGCAGCTGGTGAGGCATGGGGGTAGATTGAAGACCATTGATGAGTATCCTGTCATG
TTAATTATACTCAGAAGAAATTGATGGGTTTGTTGGGGTGGTGATGAATGATGAGA
TGATGATCATGCATCTTCTTTTCGAGATCGGTTGTACGTCGGTGATCGAGAACCCAT
GAAAAATGCAGATCARACGGCAAGACAGGTCGGAAAAAATGATCAATTTTTC
TTAAGTAGCCGGCCTGCCACCCTGCCGATTGGCATTTTGTGGTCACTTTTCA
TATCGTGTAGTATTTTGGTTTTGTTTTTAATGTTTTCTATGAATTTGAATAAT
TTGTGCTTCATGAAAATTTTTTTT
```

FIG. 3B

RADIOIMAGE OF TLC PLATE SHOWING INCORPORATION OF 1-$^{14}$C 16:0 CoA INTO WAX IN ASSAYS OF THE PELLET FRACTIONS PREPARED FROM DEVELOPING SEEDS OF ARABIDOPSIS TRANSFORMED WITH pCGN8559. A MEMBRANE FRACTION FROM DEVELOPING JOJOBA SEED IS THE POSITIVE CONTROL. BACKGROUND ACTIVITY IS ILLUSTRATED IN THE ASSAYS OF ARABIDOPSIS PLANTS 8612-3 AND 8613-2.

```
GTCTCCATTACAATGGAGGTGGAGAAGGAGCTAAAGACCTTCTCAGAGGTA
TGGATCTCCGCCATAGCCGCCGCTGCTACGCCGCTTCGTCCCCGCCGT
TGCCCCTCACGGGCGCGCTCTCCCCCTCCGCCTCCTCCTCCCCGTCGTCC
TCCTCTTCATTTTCCTCCCGCCTCCGGCTTGCCAACTTCCACCTCGGCGGC
CCACCGCCCTTGTATCTCGTCTTTATCTAACCCCTCTCTCCTTCTCTTCGC
CTTTCATCTTGGCCCTTTATCTAACCCCTCTCTCTCCTTCACTTCATCT
CCACCACCCCTCCCCATCAAGTTCAGAGATGACCCATCTAATGATCATGA
GAAAAACAAGAGAACTCGAGTTTTGAGTGGCGTAAAGTTGTTCTTTTGTT
GCTAAGTTGTGTTTTGTGATCTCGGTGCTTTACTGTTTTCACTTCTATCTCGGG
ATTTGCCTCATTTTGTGATCTCGGTGCTTTACTGTTTTCACTTCTATCTCGGG
ACGGAGATCACCCTAGCAAGCGCAGTCATAGCTCGAGCTCCACGCTAGG
GTTAGACCCTATACCCCCAGTTCAACGAGCCATACTTAGCCACCTCGCTGCA
AGACTTCTGGGGCGCAGGTGAACCTCATGGTGTCAGAGTCGATCTTGGGT
TGACAACATACCAGCCCTGTCCGGCAATGTTGGTGGCGTTCACGGTGTCGGGGCTG
CGGTGGGAGGTGGTCCGCCGGCAATGTTGGTGGCGTTCACGGTGTCGGGGC
TAATGCATGAAGTGTTTCTTTGTTCTTCTTGTTGCATGCAAGGTGCGCGAGCCCTCGTGGG
AGGTGACGGGGGTTCTTTGTTGCATGCAAGGTGCGCGAGCCCGTGGAGATG
GTGGTGAAGAAGGCGGTTCAGGCAAGGTGCGCGCTGGAGGGTGGTTGTTT
CAGGGGCGCTGAGCGGTGGAGGCATGGAGATTGAAGACCATTGATGAGTAT
TTGCCGCAGCTGGTGAGGCATGGAGATTGAAGACCATTGATGAGTAT
CCTGTCATGTTTAATTATACTCAGAAGAAATTGATGGGTTTGTTGGGTGGT
GATGAATGATGAGATGATGATCATGAAAAATTTTCATCGTGTAGATCGGTTGTA
CGTCACGAGGAGAACCATGAAAATTTTCACTTGGTCTGTAGATCGGTTGTA
GGGAAAAAAAAATGATCAATTTCCTTAAGTAGCCGGCCTGCCACCCTGTC
CGATTGTGGCATTTTGTGGTCACTTTCATATCGTGTAGTATTTTGGTTT
TTTGTTTTAATGTTTTCTATGTGAATAATTTGAATAATTTGCTTCATGAAAATTT
TTTTT
```

FIG. 10

MEVEKELKTFSEVWISAIAAACYCRFVPAVAPHGGALRLLLLLLPVVLLFIFLPLRL
SSFHLGGPTALYLVWLANFKLLFAFHLGPLSNPSLSLLHFISTLLPIKFRDDPS
NDHEKNKRTLSFEWRKVVLFVAKLVFFAGILKIYEFRKDLPHFVISVLYCFHFYL
GTEITLAASAVIARATLGLDLYPQFNEPYLATSLQDFWGRRWNLMVSDILGLTT
YQPVRRVLSRWVRLRWEVAGAMLVAFTVSGLMHEVFFFYLTRARPSWEVTGF
FVLHGVCTAVEMVVKKAVSGKVRLRREVSGALTVGFVMVTGGWLFLPQLVRH
GVDLKTIDEYPVMFNYTQKKLMGLLGW

*FIG. 11*

```
ATGGAAGAAAAGTTTAGAAAACTTAATCGAGGTATGGATCTCTGCTTTAATCT
CTCTATCTTACTGTTATTACATATCGTCTAAACTCTCCAAAGGTGTTCTTCGT
CTCCTCTCTATTCTTCCAGTCTCTGCCATTTCTGTTCTTCTTCCTCTGTTCCT
CTCTTGTGTGCACTTTTGCCCTTTCAGTTCTTTTTCTTTCATGGCTTGCAA
ACTTAAGCTTCTTCTATTTGCCTTTGCCTTCGCTTCGTTGTTCCCACTTCCT
CCAAAACTCTCCCGTTTCATCTGCTTTGATGAGGACCCTTGTTCCCACTTCCT
AAGACCCTTCTCCAAATGCGATACCAAATCTTCATCCTAAACCTATGCCTAA
ATGGGTTTTGGCTGTGTTAAAATTTTGGTCTTGGCGTCTTGTTACATGTTTAT
GAATACAGGGATGGTTTGCCTCGGTTTGTTCTTGGCTCTCTATTGTCTCC
ATATTACCTTGAGGTAGAAACTTGTCTTGGTCTTCTTTGGAGCCGTGGTATC
TACTCTTCTTGGGTGTAACATCGAGCCGGTGTTCAATGAGCCCTACCTAGC
TACCTCCCTACAAGACTTCTGGAGCCCGCAGATGGAACCTCATGGTTTCAGC
CGTCCTACGCTCAACCGTTCACATTCCGGTTCAGCGTTTTTCAAACGCATA
CTCAGTCCAGACGGGCTATGTTTGCTGGGGTCATGGCATCGTTCTTTGTC
TCAGGCTTGATGCATGAGCTGCTCTACTTTTACATGATCCGTAAGCCTCCAA
CTTGGGAAGTCACTTGTTCTTTGTTGTGCATGGTGCTGCCACTGCCACTG
AGATAGCGGTGAAGAGAACACAATGGTTGAGGCCACCGCACCGGGCTGTC
TCTGGTCTTGTAGTTCTGACGTTGTGAGTGTGACGGGCGTTTGGCTATTC
CTCGCTCAAGTGCTGAGAAAACAATGTCCATGAGAAAGCGATTGGAGAATGT
TTATTGGTTCTTGACCTAGCCAAGTTATTCACTTCTTCATGA
```

FIG. 12

```
ATGAAACAGTTAGCAACCAACAGAACCAAGAGAGAGAAAGATGGAAGAAGAG
TTGAGAAACCTAATCAAGGTTTGGATCTCTGCCTTAATCTCCATATCTTACT
GTTACTACATCTCATCATCAAAAATCTCCAAAGGTGTTCTTCGTCTCCTCTT
CTTCCCCATCTTCATCCTCAGGTTTCTTCTTCACATGGCTCGCAAATTCAAGCTC
CTTCTGCGTCATCTCAGGTTTCTTCTTCACATGGCTCGCAAATTCAAGCTC
TTTCTCTTTGCTCTTCGATCAAGAACCCTTAAGCCCACTTCCCTCAAATCTCAC
CCGTTCTTCTGCTTCGCTTGTTTCCCCATCAAAATCAATAAAAACCCTTCTT
CAAATCGAATCCACACAAACCTATGTCTAAATGGGTCCTTGCTTTCAAACT
TTTGATCTTTTCCTTCGCTTTATTACATGTGCTCTCTTTACCATTCATGATTCCGTT
TATCACGGTTCGCTTCTTGGCTTTCGTCGGTTGCCCTTGATGTCTATGCTTCTTGGTTGT
AGAACTTATCTTAGTCCGGTATTCAATGATCCTTAGCCACTTCTTTACAAGAGT
GAAATGGAACCGGTATTCAATGATCCTTAGCCACTTCTTTACAAGAGT
TTTGGAGCCGTAGATGGAACCTCATGGAAGCCGTTACTCCGTCCGTCCAGCC
GTCCACATACCGGTTCAGCGATTTGTGCACCGATTTATTGTCTCTGGTTAATGCATG
GCTTTTTACGCTGGAATGTTAGCCACGTTTATTGTCTCTGGTTAATGCATG
AGCTGATTACTTTTATGTTGTAACTTGCCTAGAGATAGCGATGAAGAGG
CTTCTTTCTTTTGCATGGAGTTGTAACTTGCCTAGAGATAGCGATGAAGAGG
ATGCGGGTGGCTTCCTCGTTACAGCCACGTCGGTTGGTTTTTACCCTCAAATGTTAAGA
GGTGTTTTTGCATGGCATAAGAGTGATAAGTGAATGTTTGTTGTTATTGACGTTG
AATGATGTGCATAAGAGTGATAAGTGAATGTTTGTTGGTTATTGACGTTG
TTAAAGGCACGTTGTCTGTATTTTAATGTAA
```

```
ATGGAAGAAGAACTCAAGAACTTCATCAAGCTTTGGATTTCAGCAATAATCT
CCATATCTTACTGTTACTACTTATCAACAGGAATCAAAGCTGGTGTTTTCGA
TTACTCTCTGTTCTTCCTGTATGTGCTCTGTTCTTCTTGTTTTCCTCTGTTTTC
TCCTATGTTCACTTCATCCTCTCCTTGGTTGCATGGCTTTTTCCTCTCATGCAA
ATTTCAAACTCTCCCGATTCATATGCATCACTTGCTCTTCCCCATCAAGCCTCAAC
AAACCCTAATATTCAAAATTATAAAATCCCCATATGGCTTTTCGCCATTAAA
GTTGTCATCTTTGTTGTCTTGTTACAAATGTATGAATACAAACAATATCTGTC
TCCGGCTTTATTATTGGTTTTTAATTCTCTACATATATTCTTGGAGCTTGAGA
TTGTCTTTATGCTCGTCAAAGCATTGGTTCTTTATCACTCTCTTGGCTTGCGATCT
AGAGCCACAGTCCAATGAACCATACTTAGCCACTTCTCTTCAAGACTTCTGG
GGTCGTCGGTGGGAACCTCATGGTCCCCGATTCTCCGGCCCGGCTGTCTA
CCTCCCGGCGAGACGAATGGCCTGTCGGAAAGTTAACTCCGATCAGGCTAT
GTTCTTGGGAGTTTCGCAGCGTTTCGTCTCCGTCCTACAGGGGAAGTCACTTGGTTC
GCTCTTCTTCTATCTTACCCGTGAGGTTCCTGAGGTTGGCGGTGGGAAGTGGCGGTGGG
TTTTGTTACATGGAGTTTGCACGGTGGAGAGTGGCGGTGGGAGTGGCGGTGAAGAAGAGT
ACATTTGTGCGCGATGGTGGTGTTGTGTGACGAGTGGTGTCTTTTTTCCCTCTTCT
GACGGTCGGTTTTTGTTGTTGTGACGAGTGGTTGGTTCTTTCCCTCTTATA
AGGAGTGGCATCATCGAAAGACTCGCTAGCGAAGCCTTAATGTGCATTGAT
TTCGTCAAGCACAAGTTTCTTCGTTACTTTTGGGTGATTAA
```

```
ATGGAGGAAGAACTCATGAGCTTAATCAAAGTATGGGTTTATGCAATAATCT
CCATATCTTACTGTTCTTCCTGTTACTACATCAACAAGAATCAAATCTGGTGTTTTCGA
TTACTATCTGTTCTTCCTGTTTGTTCTGTTTCTGTTCCTGTTCTTGTTCTCTCCCTCTGTTTGT
TTCCTCTGTTCACTTTTCTGGTTCCACAGCATTTTCCTCTCATGGCCTTGCCA
ATTCAAACTAAATCCCTCTTCCCTTCGACCAAGGTCCACTTTTCCCAGTTCC
CTCAAATCTCCCGATTCGTCTGCTTCACTTGCTTGCCCATCAAGCTTCAA
CAAAACCCTAAAATCAAAATGCCTAAAATGGGGTTTCGCAGTTAAAC
TTGCCTTCTTTGGTGTGTTGTTGCATATGTATGAATACAACAACATATGTCT
CCGACTGTTCTCTATTCTTGGTTCTCTGCATATATCTCTCTGGAGTATGAGA
TTCTCTTAGCTCCCCTGAAAGTTCTGCTTAGTATCTCTCTTTGGTGCGACCT
CGAGCCCGCATTTCAATGAACCATACTTATCCACCTCTCTTCAAGACTTCTGG
GGTCGTCGATGGAACCTCATGGTCCCCGGCGATTCTCCGGCCGGCTGTCTA
CCTCCCCGGTGCGACAAATGGCCGGTCGGAAAATGAACTCTGATCAGGCTTT
GTTCTTGGGAGTTTTGCCTCGTTGCCTCTTGTTCCGGTGGTTCACGAGCTT
ATTTCTTCTTATTTTACACGTGCACTGCAGAATCGCCGCTGAATGCGCTGAAGTCACTTTGTTCTT
TGTATTACATGGAGTTTGTTATGACCGGTGAGTGAGGTGGTTCACGACGAG
GTTGGTGCGGCGATGGAAGGTGAGTGAGTAGAGACTAGACTGAAGAGACGAG
TGGGATTTGTTGTTATGACCGGTGAGTGGTTGGTTTTTCCCTCACCTTGCAAG
GAGTGGCATGATCGAGAGACTAGACTGACGAAGCCTTTTGTTTATTGGTTTC
GTCAAGCACAAGTTTTTCTACCTTTGTAGAAACCAATCGCTAAAATCGTAG
```

FIG. 15

```
ATGGATGAAGAACTCAAGAACTTGATCAAAGTATGGGTTTCTGCAATAATCT
CGATATCTTATTGTTACTACATACCACCTAGAATCAAATCTGGTGCTCCTCG
ATTCCTCTCTGTTTCCCCTGTTCTCTGTTCTTGCTCTGTTCTTCCTCTGTTTT
TCTCCTCTCTGCATTTATCTTTAATCACAGCGTTTTCCTCACATGGCTTGCT
AATTTCAAACTCATCCTCTTCCTTCGATAAAGGTCCTTTAATCCAATTCC
AACAAATTTCCCTCGATTCTTCTGCTTCACTTGCTTCCCCATCAAGTTCAG
CAAAACCCTAAATCTCAAAACCATTGCCCAAATTGGTTTTCGCCATTAAACT
TGCAATCTTTGCAGTGCTATTACATTTGTATAGCTACAGACAAAATCTGTCTC
CGACTATACTATTAGTCTCTATTTGTGTTTTATCTCTCTGGCTGCGATCTTGA
ATATTAACGTTTGTTAAAGTTGTGTTTTTATCTCTCTGGCTGCGATCTTGA
GCCACACAGTCCAATAAAACCGTACTTAGCCACATCTCTACAAGACTTCTGGGG
TCGCCGGTGGAATCTCATGGTTCCGGCGATTCTCCGGCCAGCCGTTTACG
CACCAATGCGGCGAGTCTCTGAACGCAAAATGAGTTCCGGTTGGGCTCTGT
TTCCGGGATTTTGGCAGCGTTTATCGTCTCCGGTTTGGTTCACGAATTGC
TCTTCTCTATTTGATACGTTTGTACTGCTGTAGAATTGGCGGTGAAGAAAAC
TGTGTTACATGGCGTTTGTACTGCTGTAGAATTGGCGGTGAAGAAAAC
GACGGTAGCACAGCGGTGGCGGTTGAGTGCGGTTGTGTCGCGGGTTCTC
ACGGTGGGTTTGTTTGTGACTGGTTGGTTGTTTACACCTCAGCTT
AAAAGGAGCGGGGTGATGGAGAGATTCACATCTGAAGCTGTGTTGCTCGTT
GAGTTCATTAAGCGATAA
```

FIG. 16

```
ATGGAGGAAGAACTCAAGTTATTCATCCAAGTATGGGTTTCTGCAATCATTT
CAGTAACTTATTGTTACTACTTAACACCCAAAATCAAAACCAGTCTTCTTCGA
TTACTATCTGTTCTTCCTGTTTGTTTGTTTCTTATTATTCCTATCTTTTTC
TCCACTGTTCATTCCTCTCTTTCACTATTGCATTTTCCTCTCAGGTCTTGCAGT
TCCAAAACTCATCCTCTTTGCATTAGAAAAAAGGTCCCTCTTTTTCCACTTCCTC
CTAATCTCCCTCATTCGTCTTTGCTTTGCTTCCCATCAAGCTTCAAAA
AAAACCTAACCTGAAAATACCATTTCCCCAAATGGGTTTTTGCCCTG
AAGTTTTCATCTCTTTGGTGCCTTGTTACTACAAGCGTATCATTACAAACAATT
TCTATCTACGAATTTCTTATTGGGTCTCTCTATGCTCTGCATATATATCTTGGAGC
TTGAGATTTCCTTAACCTTGATAAAATTTCGTCAGTATCACTCTTGGGTGT
GACCTCGAGCCACAATTCAACGAACCATACTTAGCCACCTCTACATGACT
TCTGGGGTCACCGATGGAACCTCATGGTCTCGAAGATTCTCTGGCTCGCAG
TGTACAACCCCATACGGCAATGGGCGAGCCAAGAGCTCCGAGTGGGATCGG
TTCTTCGCGATTTTCGCCACGTCCCTCCCACGTGTTGCATGACACGTGT
CTCTACTTCTATTTGACATGGGTTTGCATGGCCGGCTGAAGTGGCACTGGTTCT
TTGTGTTACATGGGTTGTGTTGTGACTGGTTTGGCTATTTCCCCAGCCT
CGAAGTTGGTGCAGGCTGCAGTGTTCATGGAGAGGTTCATCAATGAAGACTTGTTCTAATTG
ACGGTGGGTTTGTTTGATGGAGAGGTTCATCAATGAAGACTTGTTCTAATTG
ATTAGGCACGGCTTGATGGAGAGGTTCATCAATGAAGACTTGTTCTAATTG
ATTTCTTTAATCGTAAGTTATATATCCCTCTTAGGGTTGTGTTTACGAGTCTTTAA
```

FIG. 17

ATGGAGGAAGAAATCAAGAGCTTGATCAATGTAGGGTTTTAACAATTATCT
CAGTATCTTACTGCTACTTCCGGTCTGTGTTTGTTAGTTGTTCTTCCTGTTCT
ATTACTCTCTATTTTCACTTCCACCAGCGTTTTCTTATCAGCTATTGCC
TCTCCTTTTCAATTTCACTCCTCTTTTCCTTTGATCAAGGTCCCTCTTTTCCACTACC
AATTCAAGACTCATCCTCTTTTCCTTTGATCAAGGTCCCTCTTTTCCACTACC
TTCAAATCTATTCAGATTTACCTGCTTTACTTGCTTCCCAATCCAGCGTCAAC
AAAACCCTAAATCTCAAGATCATTTGTCCACGTATGTTTTCCCGTTAAAATT
GCAATCTTTGTTGTGTTATATGTGCATAACGACATAACAAAACCTTCCTC
GTACTTTCTATTGTGTCTCCATCGTATGTATATTGTTACTTGAGATT
CTCTTAACGCTCCTTAGAATTCTAATGACTATCATTCTTGGTTGTGACCTAGA
GCCACATTTTCACGAACCATAGTCCACACATCTCTTCAAGACTTTTGGGGT
CGCAGGTGGAACCTCATAGTCTCGGCAAGTCTTCGGCAATCGTCTACACT
CCTGTGCGGCCGTGTCTGCCAACGAGTAATGAGCTCTGATTATGCAATGTTG
ATTGGTGTTTTGCGACGTTTGTAACCCTCGGTGGCTCATGAAGTGGTTT
TCTTTATATAACCCGTGCGATGCCTACAGGGGAAGTCGCTTTATTCTTTCT
CTTACATGGAGTTTGCACGGTGGCGGAAGTGGCAGCGAAGAGGACGGCGT
TTGTACGGAGGTGGCCGGTGAGACCAGTCGTATCTTGGATGTTCACGATAG
CGTTTGTAAATGTGACCGCTGGTTGGCTGTGTTTTTTCCTCAGTTGATTCGGAA
CAACCCTGGGGAGAGAGATGCTCCAATGAAATCTCCCTTGCTCTTGATTTCTTC
AGAAGCAAGTTATTTTATTTTCCCCAGTGA

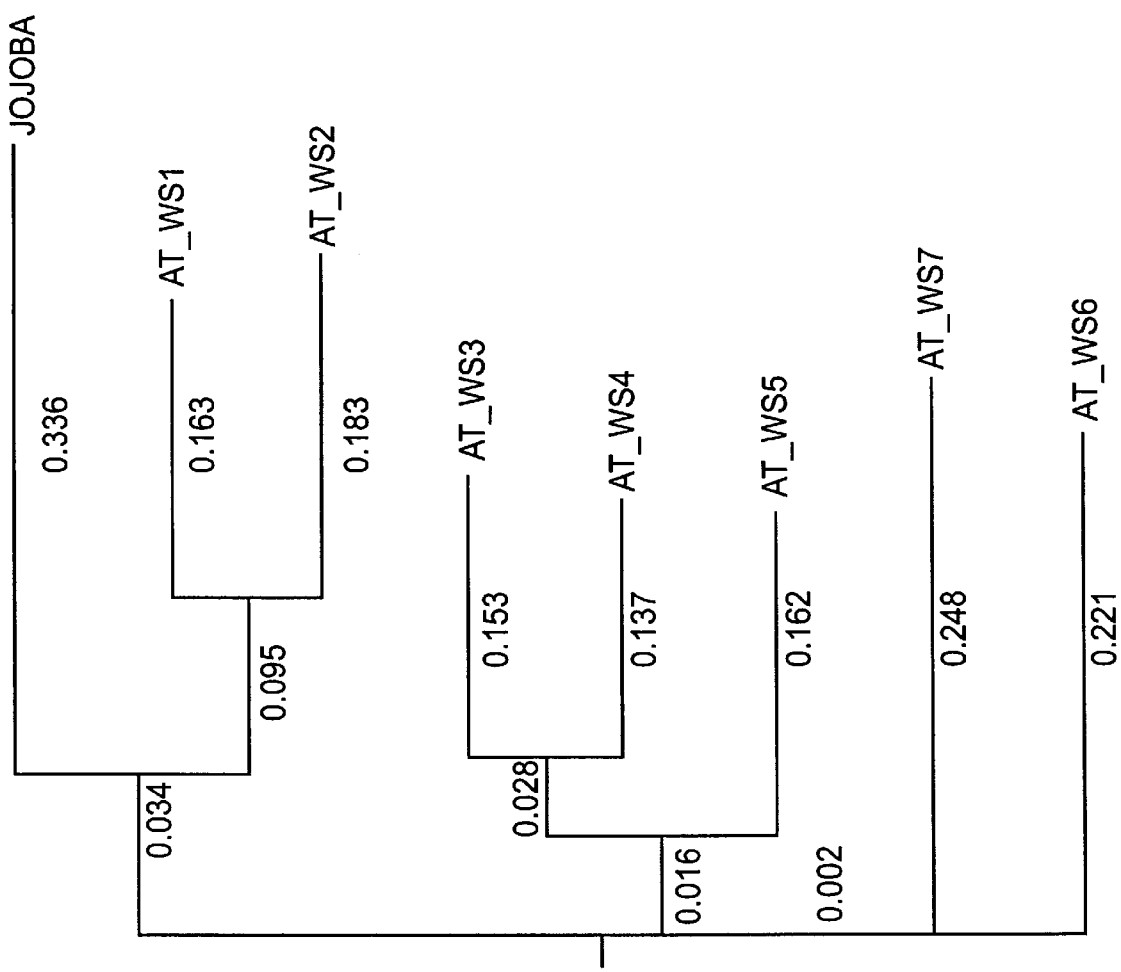

SEQUENCE LISTING

```
<160> NUMBER OF SEQ ID NOS: 49

<210> SEQ ID NO 1
<211> LENGTH: 13
<212> TYPE: PRT
<213> ORGANISM: Simmondsia chinensis
<220> FEATURE:
<221> NAME/KEY: PEPTIDE
<222> LOCATION: (1)..(13)
<223> OTHER INFORMATION: Jojoba wax synthase tryptic peptide WSpep29

<400> SEQUENCE: 1

Phe Val Pro Ala Val Ala Pro His Gly Gly Ala Leu Arg
 1               5                  10

<210> SEQ ID NO 2
<211> LENGTH: 14
<212> TYPE: PRT
<213> ORGANISM: Simmondsia chinensis
<220> FEATURE:
<221> NAME/KEY: PEPTIDE
<222> LOCATION: (1)..(14)
<223> OTHER INFORMATION: Jojoba wax synthase tryptic peptide WSpep33

<400> SEQUENCE: 2

Thr Ile Asp Glu Tyr Pro Val Met Phe Asn Tyr Thr Gln Lys
 1               5                  10

<210> SEQ ID NO 3
<211> LENGTH: 13
<212> TYPE: PRT
<213> ORGANISM: Simmondsia chinensis
<220> FEATURE:
<221> NAME/KEY: PEPTIDE
<222> LOCATION: (1)..(13)
<223> OTHER INFORMATION: peptide WSpep33

<400> SEQUENCE: 3
```

Phe Val Pro Ala Val Ala Pro His Gly Gly Ala Leu Arg
1               5                   10

<210> SEQ ID NO 4
<211> LENGTH: 14
<212> TYPE: PRT
<213> ORGANISM: Simmondsia chinensis
<220> FEATURE:
<221> NAME/KEY: PEPTIDE
<222> LOCATION: (1)..(14)
<223> OTHER INFORMATION: peptide WSpep29

<400> SEQUENCE: 4

Thr Ile Asp Glu Tyr Pro Val Met Phe Asn Tyr Thr Gln Lys
1               5                   10

<210> SEQ ID NO 5
<211> LENGTH: 9
<212> TYPE: PRT
<213> ORGANISM: Simmondsia chinensis
<220> FEATURE:
<221> NAME/KEY: PEPTIDE
<222> LOCATION: (1)..(9)
<223> OTHER INFORMATION: peptide WSpep14

<400> SEQUENCE: 5

Phe Arg Asp Asp Pro Ser Asn Asp His
1               5

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: unsure
<222> LOCATION: (1)..(17)
<223> OTHER INFORMATION: Y represents either C or T
<221> NAME/KEY: unsure
<222> LOCATION: (1)..(17)
<223> OTHER INFORMATION: N represents either A, C, G or T
<221> NAME/KEY: misc_feature
<222> LOCATION: (1)..(17)
<223> OTHER INFORMATION: corresponds to forward PCR primer WSpep29-F1

<400> SEQUENCE: 6
ttygtnccng cngtngc                                                    17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: unsure
<222> LOCATION: (1)..(17)
<223> OTHER INFORMATION: Y represents either C or T
<221> NAME/KEY: unsure
<222> LOCATION: (1)..(17)
<223> OTHER INFORMATION: N represents either A, C, G or T
<221> NAME/KEY: misc_feature
<222> LOCATION: (1)..(17)
<223> OTHER INFORMATION: corresponds to forward primer WSpep29-F2

<400> SEQUENCE: 7
gcnccncayg gnggngc                                                    17

<210> SEQ ID NO 8

<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: unsure
<222> LOCATION: (1)..(17)
<223> OTHER INFORMATION: R represents A or G
<221> NAME/KEY: unsure
<222> LOCATION: (1)..(17)
<223> OTHER INFORMATION: N represents A, C, G or T
<221> NAME/KEY: misc_feature
<222> LOCATION: (1)..(17)
<223> OTHER INFORMATION: corresponds to reverse PCR primer WSpep29-R1

<400> SEQUENCE: 8
gcnccnccrt gnggngc                                                   17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: unsure
<222> LOCATION: (1)..(17)
<223> OTHER INFORMATION: R represents either A or G
<221> NAME/KEY: unsure
<222> LOCATION: (1)..(17)
<223> OTHER INFORMATION: N represents either A, C, G or T
<221> NAME/KEY: misc_feature
<222> LOCATION: (1)..(17)
<223> OTHER INFORMATION: corresponds to reverse PCR primer WSpep29-R2

<400> SEQUENCE: 9
gcnacngcng gnacraa                                                   17

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: unsure
<222> LOCATION: (1)..(20)
<223> OTHER INFORMATION: N represents either A, C, G, or T
<221> NAME/KEY: misc_feature
<222> LOCATION: (1)..(20)
<223> OTHER INFORMATION: corresponds to forward PCR primer WSpep33-F1
<221> NAME/KEY: unsure
<222> LOCATION: (1)..(20)
<223> OTHER INFORMATION: R represents either A or G
<221> NAME/KEY: unsure
<222> LOCATION: (1)..(20)
<223> OTHER INFORMATION: Y represents either C or T

<400> SEQUENCE: 10
acnathgayg artayccngt                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: unsure
<222> LOCATION: (1)..(20)
<223> OTHER INFORMATION: Y represents either C or T
<221> NAME/KEY: unsure

```
<222> LOCATION: (1)..(20)
<223> OTHER INFORMATION: N represents either A, C, G or T
<221> NAME/KEY: misc_feature
<222> LOCATION: (1)..(20)
<223> OTHER INFORMATION: corresponds to forawrd PCR primer WSpep33-F2

<400> SEQUENCE: 11
ccngtnatgt tyaaytayac                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: unsure
<222> LOCATION: (1)..(20)
<223> OTHER INFORMATION: R represents either A or G
<221> NAME/KEY: unsure
<222> LOCATION: (1)..(20)
<223> OTHER INFORMATION: N represents either A, C, G or T
<221> NAME/KEY: misc_feature
<222> LOCATION: (1)..(20)
<223> OTHER INFORMATION: corresponds to reverse PCR primer WSpep33-R1
<221> NAME/KEY: unsure
<222> LOCATION: (1)..(20)
<223> OTHER INFORMATION: Y represents either C or T

<400> SEQUENCE: 12
ttytgngtrt arttraacat                                                 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: unsure
<222> LOCATION: (1)..(20)
<223> OTHER INFORMATION: R represents either A or G
<221> NAME/KEY: unsure
<222> LOCATION: (1)..(20)
<223> OTHER INFORMATION: N represents either A, C, G or T
<221> NAME/KEY: misc_feature
<222> LOCATION: (1)..(20)
<223> OTHER INFORMATION: corresponds to reverse PCR primer WSpep33-R2
<221> NAME/KEY: unsure
<222> LOCATION: (1)..(20)
<223> OTHER INFORMATION: Y represents either C or T

<400> SEQUENCE: 13
aacatnacng grtaytcrtc                                                 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: unsure
<222> LOCATION: (1)..(20)
<223> OTHER INFORMATION: Y represents either C or T
<221> NAME/KEY: unsure
<222> LOCATION: (1)..(20)
<223> OTHER INFORMATION: N represents A, C, G or T
<221> NAME/KEY: unsure
<222> LOCATION: (1)..(20)
<223> OTHER INFORMATION: W represents A or T
<221> NAME/KEY: unsure
<222> LOCATION: (1)..(20)
```

<223> OTHER INFORMATION: S represents either G or C
<221> NAME/KEY: misc_feature
<222> LOCATION: (1)..(20)
<223> OTHER INFORMATION: corresponds to forward PCR primer WSpep14-F1

<400> SEQUENCE: 14
gaygayccnw snaaygayca                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: unsure
<222> LOCATION: (1)..(20)
<223> OTHER INFORMATION: R represents A or G
<221> NAME/KEY: unsure
<222> LOCATION: (1)..(20)
<223> OTHER INFORMATION: N represents A, C, G or T
<221> NAME/KEY: unsure
<222> LOCATION: (1)..(20)
<223> OTHER INFORMATION: S represents G or C
<221> NAME/KEY: unsure
<222> LOCATION: (1)..(20)
<223> OTHER INFORMATION: W represents A or T
<221> NAME/KEY: misc_feature
<222> LOCATION: (1)..(20)
<223> OTHER INFORMATION: corresponds to reverse PCR primer WSpep14-R1

<400> SEQUENCE: 15
tgrtcrttns wnggrtcrtc                                              20

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(29)
<223> OTHER INFORMATION: forward PCR primer WSRACEF1

<400> SEQUENCE: 16
gatttgcctc attttgtgat ctcggtgct                                    29

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(30)
<223> OTHER INFORMATION: forward Primer WSRACEF2

<400> SEQUENCE: 17
gacctatacc cccagttcaa cgagccatac                                   30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(30)

<223> OTHER INFORMATION: forward PCR primer WSRACEF3

<400> SEQUENCE: 18
ttcaacgagc catacttagc cacctcgctg                                    30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(30)
<223> OTHER INFORMATION: reverse PCR primer WSRACER1

<400> SEQUENCE: 19
aacaaccacc ctccagtcac catcacgaac                                    30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(30)
<223> OTHER INFORMATION: reverse PCR primer WSRACER2

<400> SEQUENCE: 20
ttgcctgaaa ccgccttctt caccaccatc                                    30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(30)
<223> OTHER INFORMATION: reverse PCR primer WSRACER3

<400> SEQUENCE: 21
aagatgtctg acaccatgag gttccacctg                                    30

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(39)
<223> OTHER INFORMATION: forward PCR primer WAXSYNFOR

<400> SEQUENCE: 22
ggatccgtcg acacaatgga ggtggagaag gagctaaag                          39

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature

```
<222> LOCATION: (1)..(33)
<223> OTHER INFORMATION: reverse PCR primer WAXSYNREV

<400> SEQUENCE: 23
gcatgcagat ctcaccaccc caacaaaccc atc                                33

<210> SEQ ID NO 24
<211> LENGTH: 9
<212> TYPE: PRT
<213> ORGANISM: Arabidopsis thaliana
<220> FEATURE:
<221> NAME/KEY: UNSURE
<222> LOCATION: (1)..(9)
<223> OTHER INFORMATION: X at positions 2, 7, and 8 represent any amino
      acid
<221> NAME/KEY: UNSURE
<222> LOCATION: (1)..(9)
<223> OTHER INFORMATION: X at position 5 represents either A or S
<221> NAME/KEY: UNSURE
<222> LOCATION: (1)..(9)
<223> OTHER INFORMATION: X at position 6 represents F or L
<221> NAME/KEY: UNSURE
<222> LOCATION: (1)..(9)
<223> OTHER INFORMATION: X at position 9 represents G or E
<221> NAME/KEY: PEPTIDE
<222> LOCATION: (1)..(9)
<223> OTHER INFORMATION: conserved sequence

<400> SEQUENCE: 24

Leu Xaa Leu Phe Xaa Xaa Xaa Xaa Xaa
  1               5

<210> SEQ ID NO 25
<211> LENGTH: 19
<212> TYPE: PRT
<213> ORGANISM: Arabidopsis thaliana
<220> FEATURE:
<221> NAME/KEY: UNSURE
<222> LOCATION: (1)..(19)
<223> OTHER INFORMATION: X at position 4 represents either an A or S
<221> NAME/KEY: UNSURE
<222> LOCATION: (1)..(19)
<223> OTHER INFORMATION: X at position 8 represents either Q or H
<221> NAME/KEY: UNSURE
<222> LOCATION: (1)..(19)
<223> OTHER INFORMATION: X at position 9 represents either D or E
<221> NAME/KEY: UNSURE
<222> LOCATION: (1)..(19)
<223> OTHER INFORMATION: X at position 12 represents either G or S
<221> NAME/KEY: UNSURE
<222> LOCATION: (1)..(19)
<223> OTHER INFORMATION: X at position 13 represents either R or H
<221> NAME/KEY: UNSURE
<222> LOCATION: (1)..(19)
<223> OTHER INFORMATION: X at position 18 represents either M or I
<221> NAME/KEY: PEPTIDE
<222> LOCATION: (1)..(19)
<223> OTHER INFORMATION: conserved sequence

<400> SEQUENCE: 25

Pro Tyr Leu Xaa Thr Ser Leu Xaa Xaa Phe Trp Xaa Xaa Arg Trp Asn
  1               5                  10                  15

Leu Xaa Val

<210> SEQ ID NO 26
<211> LENGTH: 17
<212> TYPE: PRT
<213> ORGANISM: Arabidopsis thaliana
<220> FEATURE:
<221> NAME/KEY: UNSURE
<222> LOCATION: (1)..(17)
<223> OTHER INFORMATION: X at positions 2, 6, 7, 10, 11, and 15
```

```
      represent any amino acid
<221> NAME/KEY: UNSURE
<222> LOCATION: (1)..(17)
<223> OTHER INFORMATION: X at position 3 represents either V or T
<221> NAME/KEY: UNSURE
<222> LOCATION: (1)..(17)
<223> OTHER INFORMATION: X at position 12 represents either F or Y
<221> NAME/KEY: UNSURE
<222> LOCATION: (1)..(17)
<223> OTHER INFORMATION: X at position 16 represents either I or T
<221> NAME/KEY: PEPTIDE
<222> LOCATION: (1)..(17)
<223> OTHER INFORMATION: conserved sequence

<400> SEQUENCE: 26

Phe Xaa Xaa Ser Gly Xaa Xaa His Glu Xaa Xaa Xaa Phe Tyr Xaa Xaa
 1               5                  10                  15

Arg

<210> SEQ ID NO 27
<211> LENGTH: 13
<212> TYPE: PRT
<213> ORGANISM: Arabidopsis thaliana
<220> FEATURE:
<221> NAME/KEY: UNSURE
<222> LOCATION: (1)..(13)
<223> OTHER INFORMATION: X at position 7 represents any amino acid
<221> NAME/KEY: UNSURE
<222> LOCATION: (1)..(13)
<223> OTHER INFORMATION: X at position 3 represents either P or S
<221> NAME/KEY: UNSURE
<222> LOCATION: (1)..(13)
<223> OTHER INFORMATION: X at position 3 represents either W or G
<221> NAME/KEY: UNSURE
<222> LOCATION: (1)..(13)
<223> OTHER INFORMATION: X at position 6 represents either T or A
<221> NAME/KEY: UNSURE
<222> LOCATION: (1)..(13)
<223> OTHER INFORMATION: X at position 10 represents either V or L
<221> NAME/KEY: PEPTIDE
<222> LOCATION: (1)..(13)
<223> OTHER INFORMATION: conserved sequence

<400> SEQUENCE: 27

Pro Xaa Xaa Glu Val Xaa Xaa Phe Phe Xaa Leu His Gly
 1               5                  10

<210> SEQ ID NO 28
<211> LENGTH: 56
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(56)
<223> OTHER INFORMATION: adapter ligated into cloning vector pBC SK+

<400> SEQUENCE: 28
cgcgatttaa atggcgcgcc ctgcaggcgg ccgcctgcag ggcgcgccat ttaaat        56

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(32)
<223> OTHER INFORMATION: one of two sequences ligated into pCGN7770 to
      form pCGN8618
```

```
<400> SEQUENCE: 29
tcgaggatcc gcggccgcaa gcttcctgca gg                                32

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(32)
<223> OTHER INFORMATION: two of two sequences ligated into pCGN7770 to
      form pCGN8618

<400> SEQUENCE: 30
tcgacctgca ggaagcttgc ggccgcggat cc                                32

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(32)
<223> OTHER INFORMATION: one of two sequences ligated into pCGN7770 to
      form pCGN8619

<400> SEQUENCE: 31
tcgacctgca ggaagcttgc ggccgcggat cc                                32

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(32)
<223> OTHER INFORMATION: two of two sequences ligated into pCGN7770 to
      form pCGN8619

<400> SEQUENCE: 32
tcgaggatcc gcggccgcaa gcttcctgca gg                                32

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(32)
<223> OTHER INFORMATION: one of two sequences ligated into pCGN7787 to
      form pCGN8620

<400> SEQUENCE: 33
tcgaggatcc gcggccgcaa gcttcctgca ggagct                            36

<210> SEQ ID NO 34
<211> LENGTH: 28
<212> TYPE: DNA
<213> ORGANISM: Artificial Sequence
<220> FEATURE:
```

<223> OTHER INFORMATION: Description of Artificial Sequence: synthetic
      oligonucleotide
<221> NAME/KEY: misc_feature
<222> LOCATION: (1)..(28)
<223> OTHER INFORMATION: two fo two sequences ligated into pCGN7787 to
      form pCGN8620

<400> SEQUENCE: 34
cctgcaggaa gcttgcggcc gcggatcc                                        28

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(36)
<223> OTHER INFORMATION: one of two sequences ligated into pCGN7787 to
      form pCGN 8621

<400> SEQUENCE: 35
tcgacctgca ggaagcttgc ggccgcggat ccagct                               36

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(28)
<223> OTHER INFORMATION: two of two sequences ligated into pCGN7787 to
      form pCGN8621

<400> SEQUENCE: 36
ggatccgcgg ccgcaagctt cctgcagg                                        28

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(41)
<223> OTHER INFORMATION: one of two primers used to amplify AT-WS2

<400> SEQUENCE: 37
ggatccgcgg ccgcattatg aaacagttag caaccaacag a                         41

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: synthetic
      oligonucleotide
<221> NAME/KEY: misc_feature
<222> LOCATION: (1)..(40)
<223> OTHER INFORMATION: two fo two primers used to amplify AT-WS2

<400> SEQUENCE: 38
ggatcccctg caggttacat taaaatacag acaacgtgcc                           40

<210> SEQ ID NO 39

```
<211> LENGTH: 708
<212> TYPE: DNA
<213> ORGANISM: Simmondsia chinensis
<220> FEATURE:
<221> NAME/KEY: source
<222> LOCATION: (1)..(708)
<223> OTHER INFORMATION: DNA sequence of the PCR product from primers
      WSPEP14-F1 and WSPEP33-R2

<400> SEQUENCE: 39
gatgacccaw snaaygacca tgagaaaaac aagagaactc tgagttttga gtggcgtaaa      60
gttgttcttt ttgttgctaa gttggtgttt tttgcgggta ttttaaagat ttatgagttt     120
agaaaagatt tgcctcattt tgtgatctcg gtgctttact gttttcactt ctatctcggg     180
acggagatca ccttagcagc aagcgcagtc atagctcgag ccacgctagg gttagaccta     240 taccccagt tcaacgagcc atacttagcc acctcgctgc aagacttctg ggggcgcagg      300
tggaacctca tgtgtcaga catcttgggg ttgacaacat accagcctgt ccggcgtgtc     360
ctctcgaggt gggtcaggct gcggtgggag gtcgccggcg caatgttggt ggcgttcacg     420
gtgtcggggc taatgcatga agtgtttttc ttntacttaa ctcgcgcgag gccctcgtgg     480
gaggtgacgg ggttctttgt bttgcatggg gtttgcacag ccgtggagat ggtggtgaag     540
aaggcggttt caggcaaggt gcggctgcgc cgggaggtgt caggggcgct gacggtgggg     600
ttcgtgatgg tgactggagg gtggttgttt ttgccgcagc tggtgaggca tggggtagat     660
ttgaagacca ttgatgagta tcctgtcatg ttyaaytaya cccagaaa                 708

<210> SEQ ID NO 40
<211> LENGTH: 1335
<212> TYPE: DNA
<213> ORGANISM: Simmondsia chinensis
<220> FEATURE:
<221> NAME/KEY: source
<222> LOCATION: (1)..(1335)
<223> OTHER INFORMATION: DNA sequence of the Wax cDNA inferred from 5'
      and 3' RACE products

<400> SEQUENCE: 40
gtctccatta caatggaggt ggagaaggag ctaaagacct tctcagaggt atggatctcc      60
gccatagccg ccgcctgcta ctgccgcttc gtccccgccg ttgccccctca cggcggcgct    120 ctccgcctcc tcctcctcct cccgtcgtc ctcctcttca ttttcctccc cctccgcctc     180
tcctccttcc acctcggcgg gcccaccgcc ttgtatctcg tctggcttgc caacttcaag    240
ctccttctct tcgcctttca tcttggccct ttatctaacc cctctctctc tctccttcac    300
ttcatctcca ccaccctcct ccccatcaag ttcagagatg acccatctaa tgatcatgag    360
aaaaacaaga gaactctgag ttttgagtgg cgtaaagttg ttcttttttgt tgctaagttg     420 gtgttttttg cgggtatttt aaagatttat gagtttagaa aagatttgcc tcattttgtg    480
atctcggtgc tttactgttt tcacttctat ctcgggacgg agatcacctt agcagcaagc    540
gcagtcatag ctcgagccac gctagggtta gacctatacc cccagttcaa cgagccatac    600
ttagccacct cgctgcaaga cttctggggg cgcaggtgga acctcatggt gtcagacatc    660
ttggggttga acaatacca gcctgtccgg cgtgtcctct cgaggtgggt caggctgcgg    720
tgggaggtcg ccggcgcaat gttggtggcg ttcacgtgt cggggctaat gcatgaagtg    780
ttttctttct acttaactcg cgcgaggccc tcgtgggagg tgacgggtt ctttgtgttg    840 catgggtttt gcacagccgt ggagatggtg gtgaagaagg cggtttcagg caaggtgcgg    900
ctgcgccggg aggtgtcagg ggcgctgacg gtggggttcg tgatggtgac tggagggtgg    960
```

```
ttgtttttgc cgcagctggt gaggcatggg gtagatttga agaccattga tgagtatcct    1020
gtcatgttta attatactca gaagaaattg atgggtttgt tggggtggtg atgaatgatg    1080
agatgatgat catgcatctt cttttcgga gatcggttgt acgtcacgag gagaacccat    1140
gaaaaatgca gatcaracgg caagacaggt cgggaaaaaa aaatgatcaa ttttccctta    1200
agtagccggc ctgccaccct gtccgattgt ggcattttg tggtcacttt ttcatatcgt    1260
gtagtatttt tggttttttg tttttaatgt tttctatgaa ttttgaataa tttgtgcttc    1320
atgaaaattt ttttt                                                     1335
```

<210> SEQ ID NO 41
<211> LENGTH: 1335
<212> TYPE: DNA
<213> ORGANISM: Simmondsia chinensis
<220> FEATURE:
<221> NAME/KEY: gene
<222> LOCATION: (1)..(1335)
<223> OTHER INFORMATION: DNA sequence of Jojoba wax synthase

<400> SEQUENCE: 41

```
gtctccatta caatggaggt ggagaaggag ctaaagacct tctcagaggt atggatctcc      60
gccatagccg ccgcctgcta ctgccgcttc gtccccgccg ttgcccctca cggcggcgct     120
ctccgcctcc tcctcctcct ccccgtcgtc ctcctcttca ttttcctccc cctccgcctc     180
tcctccttcc acctcggcgg gcccaccgcc ttgtatctcg tctggcttgc caacttcaag     240
ctccttctct tcgcctttca tcttggccct ttatctaacc cctctctctc tctccttcac     300
ttcatctcca ccaccctcct ccccatcaag ttcagagatg acccatctaa tgatcatgag     360
aaaaacaaga gaactctgag ttttgagtgg cgtaaagttg ttcttttttgt tgctaagttg     420 gtgtttttg cgggtatttt aaagattat gagtttagaa aagatttgcc tcattttgtg      480
atctcggtgc tttactgttt tcacttctat ctcgggacgg agatcacctt agcagcaagc     540
gcagtcatag ctcgagccac gctagggtta gacctatacc cccagttcaa cgagccatac     600
ttagccacct cgctgcaaga cttctggggg cgcaggtgga acctcatggt gtcagacatc     660
ttggggttga caacatacca gcctgtccgg cgtgtcctct cgaggtgggt caggctgcgg     720
tgggaggtcg ccggcgcaat gttggtggcg ttcacggtgt cggggctaat gcatgaagtg     780
tttttcttct acttaactcg cgcgaggccc tcgtgggagg tgacgggggtt ctttgtgttg     840 catggggttt gcacagccgt ggagatggtg gtgaagaagg cggtttcagg caaggtgcgg     900
ctgcgccggg aggtgtcagg ggcgctgacg gtggggttcg tgatggtgac tggagggtgg     960
ttgtttttgc cgcagctggt gaggcatggg gtagatttga agaccattga tgagtatcct    1020
gtcatgttta attatactca gaagaaattg atgggtttgt tggggtggtg atgaatgatg    1080
agatgatgat catgcatctt cttttcgga gatcggttgt acgtcacgag gagaacccat    1140
gaaaaatgca gatcaracgg caagacaggt cgggaaaaaa aaatgatcaa ttttccctta    1200
agtagccggc ctgccaccct gtccgattgt ggcattttg tggtcacttt ttcatatcgt    1260
gtagtatttt tggttttttg tttttaatgt tttctatgaa ttttgaataa tttgtgcttc    1320
atgaaaattt ttttt                                                     1335
```

<210> SEQ ID NO 42
<211> LENGTH: 352
<212> TYPE: PRT
<213> ORGANISM: Simmondsia chinensis
<220> FEATURE:

-continued

```
<221> NAME/KEY: PEPTIDE
<222> LOCATION: (1)..(352)
<223> OTHER INFORMATION: amino acid sequence for jojoba wax synthase

<400> SEQUENCE: 42
```

| | | | | | | | | | | | | | | | |
|---|---|---|---|---|---|---|---|---|---|---|---|---|---|---|---|
| Met | Glu | Val | Glu | Lys | Glu | Leu | Lys | Thr | Phe | Ser | Glu | Val | Trp | Ile | Ser |
| 1 | | | | 5 | | | | | 10 | | | | | 15 | |
| Ala | Ile | Ala | Ala | Ala | Cys | Tyr | Cys | Arg | Phe | Val | Pro | Ala | Val | Ala | Pro |
| | | | 20 | | | | | 25 | | | | | 30 | | |
| His | Gly | Gly | Ala | Leu | Arg | Leu | Leu | Leu | Leu | Pro | Val | Val | Leu | Leu | |
| | | 35 | | | | | 40 | | | | | 45 | | | |
| Phe | Ile | Phe | Leu | Pro | Leu | Arg | Leu | Ser | Ser | Phe | His | Leu | Gly | Gly | Pro |
| | 50 | | | | | 55 | | | | | 60 | | | | |
| Thr | Ala | Leu | Tyr | Leu | Val | Trp | Leu | Ala | Asn | Phe | Lys | Leu | Leu | Leu | Phe |
| 65 | | | | | 70 | | | | | 75 | | | | | 80 |
| Ala | Phe | His | Leu | Gly | Pro | Leu | Ser | Asn | Pro | Ser | Leu | Ser | Leu | Leu | His |
| | | | | 85 | | | | | 90 | | | | | 95 | |
| Phe | Ile | Ser | Thr | Thr | Leu | Leu | Pro | Ile | Lys | Phe | Arg | Asp | Asp | Pro | Ser |
| | | | 100 | | | | | 105 | | | | | 110 | | |
| Asn | Asp | His | Glu | Lys | Asn | Lys | Arg | Thr | Leu | Ser | Phe | Glu | Trp | Arg | Lys |
| | | 115 | | | | | 120 | | | | | 125 | | | |
| Val | Val | Leu | Phe | Val | Ala | Lys | Leu | Val | Phe | Phe | Ala | Gly | Ile | Leu | Lys |
| | 130 | | | | | 135 | | | | | 140 | | | | |
| Ile | Tyr | Glu | Phe | Arg | Lys | Asp | Leu | Pro | His | Phe | Val | Ile | Ser | Val | Leu |
| 145 | | | | | 150 | | | | | 155 | | | | | 160 |
| Tyr | Cys | Phe | His | Phe | Tyr | Leu | Gly | Thr | Glu | Ile | Thr | Leu | Ala | Ala | Ser |
| | | | | 165 | | | | | 170 | | | | | 175 | |
| Ala | Val | Ile | Ala | Arg | Ala | Thr | Leu | Gly | Leu | Asp | Leu | Tyr | Pro | Gln | Phe |
| | | | 180 | | | | | 185 | | | | | 190 | | |
| Asn | Glu | Pro | Tyr | Leu | Ala | Thr | Ser | Leu | Gln | Asp | Phe | Trp | Gly | Arg | Arg |
| | | 195 | | | | | 200 | | | | | 205 | | | |
| Trp | Asn | Leu | Met | Val | Ser | Asp | Ile | Leu | Gly | Leu | Thr | Thr | Tyr | Gln | Pro |
| | 210 | | | | | 215 | | | | | 220 | | | | |
| Val | Arg | Arg | Val | Leu | Ser | Arg | Trp | Val | Arg | Leu | Arg | Trp | Glu | Val | Ala |
| 225 | | | | | 230 | | | | | 235 | | | | | 240 |
| Gly | Ala | Met | Leu | Val | Ala | Phe | Thr | Val | Ser | Gly | Leu | Met | His | Glu | Val |
| | | | | 245 | | | | | 250 | | | | | 255 | |
| Phe | Phe | Phe | Tyr | Leu | Thr | Arg | Ala | Arg | Pro | Ser | Trp | Glu | Val | Thr | Gly |
| | | | 260 | | | | | 265 | | | | | 270 | | |
| Phe | Phe | Val | Leu | His | Gly | Val | Cys | Thr | Ala | Val | Glu | Met | Val | Val | Lys |
| | | 275 | | | | | 280 | | | | | 285 | | | |
| Lys | Ala | Val | Ser | Gly | Lys | Val | Arg | Leu | Arg | Arg | Glu | Val | Ser | Gly | Ala |
| | 290 | | | | | 295 | | | | | 300 | | | | |
| Leu | Thr | Val | Gly | Phe | Val | Met | Val | Thr | Gly | Gly | Trp | Leu | Phe | Leu | Pro |
| 305 | | | | | 310 | | | | | 315 | | | | | 320 |
| Gln | Leu | Val | Arg | His | Gly | Val | Asp | Leu | Lys | Thr | Ile | Asp | Glu | Tyr | Pro |
| | | | | 325 | | | | | 330 | | | | | 335 | |
| Val | Met | Phe | Asn | Tyr | Thr | Gln | Lys | Lys | Leu | Met | Gly | Leu | Leu | Gly | Trp |
| | | | 340 | | | | | 345 | | | | | 350 | | |

```
<210> SEQ ID NO 43
<211> LENGTH: 1026
<212> TYPE: DNA
<213> ORGANISM: Arabidopsis thaliana
<220> FEATURE:
<221> NAME/KEY: gene
```

<222> LOCATION: (1)..(1026)
<223> OTHER INFORMATION: sequence of AT_WS1

<400> SEQUENCE: 43

| | | |
|---|---|---|
| atggaagaaa agtttagaaa cttaatcgag gtatggatct ctgctttaat ctctctatct | 60 |
| tactgttatt acatatcgtc taaactctcc aaaggtgttc ttcgtctcct ctctattctt | 120 |
| ccagtctgca ttctgtttct tgttcttcct ctgttcctct cttgtgtgca cttttgcgcc | 180 |
| atttcagttc tttttctttc atggcttgca aactttaagc ttcttctatt tgcctttgat | 240 |
| gagggacctt tgttcccact tcctccaaaa ctctcccgtt tcatctgctt cgcttgttta | 300 |
| cccatcaaaa tcagacaaga cccttctcca aatgcgatac caaatcttca tcctaaacct | 360 |
| atgcctaaat gggttttggc tgttaaaatt ttggtcttgg gcgtcttgtt acatgtttat | 420 |
| gaatacaggg atggtttgcc tcggtttgtt gtcttggctc tctattgtct ccatatttac | 480 |
| cttgaggtag aacttgtctt ggtctttgtt ggagccgtgg tatctactct tcttgggtgt | 540 |
| aacatcgagc cggtgttcaa tgagccctac ctagctacct ccctacaaga cttctggagc | 600 |
| cgcagatgga acctcatggt ttcagccgtc ctacgctcaa ccgttcacat tccggttcag | 660 |
| cgttttttca aacgcatact cagtccagac ggggctatgt tgctggggt catggcatcg | 720 |
| ttctttgtct caggcttgat gcatgagctg ctctactttt acatgatccg taagcctcca | 780 |
| acttgggaag tcacttgttt ctttgtgttg catggtgctg ccactgccac tgagatagcg | 840 |
| gtgaagagaa cacaatggtt gaggccaccg caccgggctg tctctggtct tgtagttctg | 900 |
| acgtttgtga gtgtgacggg cgtttggcta ttcctcgctc aagtgctgag aaacaatgtc | 960 |
| catgagaaag cgattggaga atgtttattg gttcttgacc tagccaagtt attcacttct | 1020 |
| tcatga | 1026 |

<210> SEQ ID NO 44
<211> LENGTH: 1071
<212> TYPE: DNA
<213> ORGANISM: Arabidopsis thaliana
<220> FEATURE:
<221> NAME/KEY: gene
<222> LOCATION: (1)..(1071)
<223> OTHER INFORMATION: sequence of AT_WS2

<400> SEQUENCE: 44

| | | |
|---|---|---|
| atgaaacagt tagcaaccaa cagaaccaag agagaaaaga tggaagaaga gttgagaaac | 60 |
| ctaatcaagg tttggatctc tgccttaatc tccatatctt actgttacta catctcatca | 120 |
| aaaatctcca aaggtgttct tcgtctcctc tctcttcttc ccatcttcat catctttctt | 180 |
| cttcttcctc tcttcttctc ttctgtccac ttctgcgtca tctcaggttt cttcttcaca | 240 |
| tggctcgcaa atttcaagct cttttctcttt gctttcgatc aagaaccttt aagcccactt | 300 |
| ccctcaaatc tcaccgcttt cttctgcttc gcttgtttcc ccatcaaaat caataaaaac | 360 |
| ccttcttcaa atcgaatcca caacaaacct atgtctaaat gggtccttgc tttcaaactt | 420 |
| ttgatctttt ccttccttatt acatgtgtat agaaacaact atgattccgg tttatcacgg | 480 |
| ttcgctttct tggctctctt taccattcat gtttacctcg aggcagaact tatcttagtc | 540 |
| ttcgtcggtg ccttgatgtc tatgcttctt ggttgtgaaa tggaaccggt attcaatgat | 600 |
| ccttacttag ccacttcttt acaagagttt tggagccgta gatggaacct catggtccca | 660 |
| gccgtactcc gtccagccgt ccacataccg gttcagcgat tttgtgcacc gttactcggt | 720 |
| ctacaccggg cttttttacgc tggaatgtta gccacgttta ttgtctctgg tttaatgcat | 780 |

-continued

```
gagctgattt actttatgt tatccgcaaa tctccaactt gggaagtcac ttgcttcttt      840
cttttgcatg gagttgtaac ttgcctagag atagcgatga agaggatgcg gtggcttcct      900
acgccacgtc gggcggtctc gggtcttgca attacggtgt ttttgctcgt tacagctggt      960
tggttgtttt accctcaaat gttaagaaat gatgtgcata agagagtgat aagtgaatgt     1020
ttgttggtta ttgacgttgt taaaaggcac gttgtctgta ttttaatgta a             1071
```

<210> SEQ ID NO 45
<211> LENGTH: 1029
<212> TYPE: DNA
<213> ORGANISM: Arabidopsis thaliana
<220> FEATURE:
<221> NAME/KEY: gene
<222> LOCATION: (1)..(1029)
<223> OTHER INFORMATION: sequence of AT_WS3

<400> SEQUENCE: 45

```
atggaagaag aactcaagaa cttcatcaag ctttggattt cagcaataat ctccatatct       60
tactgttact acttatcaac aggaatcaaa gctggtgttt ttcgattact ctctgttctt      120
cctgtatgtg ctctgtttct tgttttttcct ctgtttttct cctatgttca cttctctggt     180
tgcatggctt ttttcctctc atggctcgca aatttcaaac tcatcctctt ctccttcgat      240
caaggtcctc tttccccact tcctcgaact ctctcccgat tcatatgcat cacttgcttc      300
cccatcaagc ctcaacaaaa ccctaatatt caaaattata aaatccccat atggcttttc      360
gccattaaag ttgtcatctt tgttgtcttg ttacaaatgt atgaatacaa acaatatctg      420
tctccggctt tattattggt ttttaattct ctacatatat tcttggagct tgagattgtc      480
tttatgctcg tcaaagcatt ggtctttatc actcttggct gcgatctaga gccacagtcc      540
aatgaaccat acttagccac ttctcttcaa gacttctggg gtcgtcggtg aacctcatg      600 gtcccggcga ttctccggcc ggctgtctac ctcccggcga acgaatggc ctgtcggaaa       660 gttaactccg atcaggctat gttcttggga gttttcgcag cgtttctcgt ctccggtgcg      720
gttcatgaga tgctcttctt ctatcttacc cgtgaggttc ctacagggga agtcacttgg      780
ttctttttgt tacatggagt ttgcacggtg gcggaagtgg cggtgaagaa gagtacattt      840
gtgcggcgat ggtggagagt gagtccgacg gtgtcacgtc ttctgacggt cggttttgtt      900
gttgtgacga gtggttggtt ctttttccct cttataagga gtggcatcat cgaaagactc      960
gctagcgaag ccttaatgtg cattgatttc gtcaagcaca agtttcttct gttacttttg     1020
ggtgattaa                                                             1029
```

<210> SEQ ID NO 46
<211> LENGTH: 1038
<212> TYPE: DNA
<213> ORGANISM: Arabidopsis thaliana
<220> FEATURE:
<221> NAME/KEY: gene
<222> LOCATION: (1)..(1038)
<223> OTHER INFORMATION: sequence of AT_WS4

<400> SEQUENCE: 46

```
atggaggaag aactcatgag cttaatcaaa gtatgggttt atgcaataat ctccatatct       60
tactgttact acacatcaac aagaatcaaa tctggtgttt ttcgattact atctgttctt      120
cctgtttgtg ttctgtttct tgttctccct ctgtttgttt cctctgttca cttttctggt      180
tccacagcat ttttcctctc atggcttgcc aatttcaaac taatcctctt ctccttcgac      240
caaggtccac ttttcccagt tccctcaaat ctctcccgat tcgtctgctt cacttgcttc      300
```

```
cccatcaagc ttcaacaaaa ccctaaacct caaaatcaaa tgcctaaatg gggtttcgca     360
gttaaacttg ccttctttgg tgtgttgttg catatgtatg aatacaaaca acatatgtct     420
ccgactgttc tattggttct ctattctctg catatatact tggagtatga gattctctta     480
gctcccttga aagttctgct tagtatctct ctttggtgcg acctcgagcc gcatttcaat     540
gaaccatact tatccacctc tcttcaagac ttctggggtc gtcgatggaa cctcatggtc     600
ccggcgattc tccggccggc tgtctacctc ccggtgcgac aaatggccgg tcggaaaatg     660
aactctgatc aggctttgtt cttgggagtt tttgcctcgt tccttgtttc cggtgtggtt     720
cacgagctta ttttcttcta ttttacacgt gaatcgccga caggtgaagt cactttgttc     780
tttgtattac atggagtttg cactgccgct gaatgcgctg cgaagaggac gaggttggtg     840
cggcgatgga aggtgagtca gatggtttca cgactgctca cggtgggatt tgttgttatg     900
accggtggtt ggttgttttt ccctcacctt gcaaggagtg gcatgatcga gagactagct     960
gacgaagcct ttttgtttat tggtttcgtc aagcacaagt ttttctacct ttgtagaaac    1020
caatcgctaa aatcgtag                                                  1038

<210> SEQ ID NO 47
<211> LENGTH: 1002
<212> TYPE: DNA
<213> ORGANISM: Arabidopsis thaliana
<220> FEATURE:
<221> NAME/KEY: gene
<222> LOCATION: (1)..(1002)
<223> OTHER INFORMATION: sequence of AT_WS5

<400> SEQUENCE: 47
atggatgaag aactcaagaa cttgatcaaa gtatgggttt ctgcaataat ctcgatatct      60
tattgttact acataccacc tagaatcaaa tctggtgctc ctcgattcct ctctgtttcc     120
cctgttcttg ctctgtttct tgttcttcct ctgtttttct cctctctgca tttatcttta     180
atcacagcgt ttttcctcac atggcttgct aatttcaaac tcatcctctt ctccttcgat     240
aaaggtcctt taatcccaat tccaacaaat ttccctcgat tcttctgctt cacttgcttc     300
cccatcaagg ttcagcaaaa ccctaaatct caaaaccatt tgcccaaatt ggttttcgcc     360
attaaacttg caatctttgc agtgctatta catttgtata gctacagaca aaatctgtct     420
ccgactatac tattaggtct ctattttgtg catctctact tagagattga gattatatta     480
acgtttgtta aagttgttgt ttttatctct cttggctgcg atcttgagcc acagtccaat     540
aaaccgtact tagccacatc tctacaagac ttctggggtc gccggtggaa tctcatggtt     600
ccggcgattc tccggccagc cgtttacgca ccaatgcggc gagtctctga acgcaaaatg     660
agttccggtt gggctctgtt tccggggatt ttggcagcgt ttatcgtctc cggtttggtt     720
cacgaattgc tcttcttcta tttgatacgt gagatgccta caggagaagt tactctgttc     780
tttgtgttac atggcgtttg tactgctgta gaattggcgg tgaagaagaa aacgacggta     840
gcacagcggt ggcggttgag tccggggtgt cgcgggttc tcacggtggg gtttgtgttt     900
gtgactggtg gttggttgtt tacacctcag cttaaaagga gcggggtgat ggagagattc     960
acatctgaag ctgtgttgct cgttgagttc attaagcgat aa                       1002

<210> SEQ ID NO 48
<211> LENGTH: 1041
<212> TYPE: DNA
<213> ORGANISM: Arabidopsis thaliana
<220> FEATURE:
```

<221> NAME/KEY: gene
<222> LOCATION: (1)..(1041)
<223> OTHER INFORMATION: sequence of AT_WS6

<400> SEQUENCE: 48

| | | | | | |
|---|---|---|---|---|---|
| atggaggaag | aactcaagtt | attcatccaa | gtatgggttt | ctgcaatcat | ttcagtaact | 60 |
| tattgttact | acttaacacc | caaaatcaaa | accagtcttc | ttcgattact | atctgttctt | 120 |
| cctgtttgtg | ttttgtttct | tattattcct | atcttttct | ccactgttca | ttcctctttc | 180 |
| actattgcat | ttttcctctc | aggtcttgca | gttccaaaac | tcatcctctt | tgcattagaa | 240 |
| aaaggtcctc | tttttccact | tcctcctaat | ctccctcatt | tcgtctgctt | tgcttgcttc | 300 |
| cccatcaagc | ttcaaaaaaa | acctaaccct | gaaaatacta | accatttccc | caaatgggtt | 360 |
| tttgccctga | agttttcat | ctttggtgcc | ttgttactac | aagcgtatca | ttacaaacaa | 420 |
| tttctatcta | cgaatttct | attgggtctc | tatgctctgc | atatatactt | ggagcttgag | 480 |
| atttccttaa | ccttgataaa | atttctcgtc | agtatcactc | ttgggtgtga | cctcgagcca | 540 |
| caattcaacg | aaccatactt | agccacctct | ctacatgact | tctggggtca | ccgatggaac | 600 |
| ctcatggtct | cgaagattct | ctggctcgca | gtgtacaacc | ccatacggca | atggcgagcc | 660 |
| aagagctccg | agtgggatcg | gttcttcgcg | attttcgcca | cgttcctcgt | ctctggtgtg | 720 |
| gctcacgaga | ttctctactt | ctatttgaca | cgtgagaagc | tacatgggga | ggtgacttgg | 780 |
| ttctttgtgt | tacatgggtt | ttgcatggcg | gctgaagtgg | cactgaagag | gaagacgaag | 840 |
| ttggtgcagc | ggtggccggt | gaatccggca | gtgtcgagac | tgcttacggt | ggggtttgtg | 900 |
| tttgtgactg | gtgtttggct | atttttccccc | cagcctatta | ggcacggctt | gatggagagg | 960 |
| ttcatcaatg | aagacttgtt | tctaattgat | ttctttaatc | gtaagttata | tatcctctta | 1020 |
| gggttgttta | cgagtcttta | a | | | | 1041 |

<210> SEQ ID NO 49
<211> LENGTH: 1020
<212> TYPE: DNA
<213> ORGANISM: Arabidopsis thaliana
<220> FEATURE:
<221> NAME/KEY: gene
<222> LOCATION: (1)..(1020)
<223> OTHER INFORMATION: sequence of AT_WS7

<400> SEQUENCE: 49

| | | | | | |
|---|---|---|---|---|---|
| atggaggaag | aaatcaagag | cttgatcaat | gtagggtttt | taacaattat | ctcagtatct | 60 |
| tactgctact | gcttaccacc | aagaatcaaa | tctggtgttc | ttcgattact | ctctattttt | 120 |
| ccggtctgtg | ttttgttagt | tgttcttcct | ctgttcttct | ccttttcaat | tttcacttcc | 180 |
| accacagcgt | ttttcttatc | agctattgcc | aattcaagac | tcatcctctt | ttcctttgat | 240 |
| caaggtcctc | tttttccact | accttcaaat | ctattcagat | ttacctgctt | tacttgcttc | 300 |
| ccaatccagc | gtcaacaaaa | ccctaaatct | caagatcatt | tgtccacgta | tgttttccc | 360 |
| gttaaaattg | caatctttgt | tgtgttgtta | tatgtgcata | acgacataca | aaaccttcct | 420 |
| cgtactttc | tattgtgtct | ccatccactg | tatgtatatt | tgttacttga | gattctctta | 480 |
| acgctcctta | gaattctaat | gactatcatt | cttggttgtg | acctagagcc | acattttcac | 540 |
| gaaccatact | tagccacatc | tcttcaagac | tttgggtc | gcaggtggaa | cctcatagtc | 600 |
| tcggcaagtc | ttcgggcaat | cgtctacact | cctgtgcggc | gtgtctgcca | acgagtaatg | 660 |
| agctctgatt | atgcaatgtt | gattggtgtt | tttgcgacgt | ttgtaacctc | tggtgtggct | 720 |
| catgaagtgg | ttttcttta | tataacccgt | gcgatgccta | cagggaagt | cgctttattc | 780 |

-continued

```
tttctcttac atggagtttg cacggtggcg gaagtggcag cgaagaggac ggcgtttgta    840
cggaggtggc cggtgagacc agtcgtatct tggatgttca cgatagcgtt tgtaaatgtg    900
accgctggtt ggctgttttt tcctcagttg attcggaaca acctggggga gagatgctcc    960
aatgaaatct ccttgctcat tgatttcttc agaagcaagt tattttattt tccccagtga   1020
```

FATTY ACYL-COA: FATTY ALCOHOL ACYLTRANSFERASES

This application is a continuation in part of U.S. patent application Ser. No. 09/092,562, filed Jun. 5, 1998, and a continuation in part of PCT/US98/11590, Jun. 5, 1998, which claims priority to U.S. patent application Ser. No. 60/048,651, filed Jun. 5, 1997, and is a continuation of U.S. patent application Ser. No. 08/265,047, filed Jun. 23, 1994, issued as U.S. Pat. No. 5,679,881.

Technical Field

The present invention is directed to enzymes, methods to purify, and obtain such enzymes, amino acid and nucleic acid sequences related thereto, and methods of use for such compositions in genetic engineering applications.

INTRODUCTION

Background

Through the development of plant genetic engineering techniques, it is possible to transform and regenerate a variety of plant species to provide plants which have novel and desirable characteristics. One area of interest for such plant genetic engineering techniques is the production of valuable products in plant tissues. Such applications require the use of various DNA constructs and nucleic acid sequences for use in transformation events to generate plants which produce the desired product. For example, plant functional promoters are required for appropriate expression of gene sequences, such expression being either in the whole plant or in selected plant tissues. In addition, selective marker sequences are often used to identify the transformed plant material. Such plant promoters and selectable markers provide valuable tools which are useful in obtaining the novel plants.

A desirable goal which involves such genetic engineering techniques, is the ability to provide crop plants having a convenient source of wax esters. Wax esters are required in a variety of industrial applications, including pharmaceuticals, cosmetics, detergents, plastics, and lubricants. Such products, especially long chain wax esters have previously been available from the sperm whale, an endangered species, or more recently, from the desert shrub, jojoba. Neither of these sources provides a convenient supply of wax esters. Thus, in order to obtain a reliable source of such compounds, transformation of crop plants, which are easily manipulated in terms of growth, harvest and extraction of products, is desirable.

In order to obtain such transformed plants, however, the genes responsible for the biosynthesis of the desired wax ester products must first be obtained. Wax ester production results from the action of at least two enzymatic activities, fatty acyl reductase and fatty acyl:fatty alcohol acyltransferase, or wax synthase. In addition, a β-ketoacyl-Coenzyme A synthase may also be involved in wax biosynthesis by providing very long chain fatty acyl-CoA substrates for the reductase and wax synthase enzymatic reaction. Preliminary studies with such enzymes and extensive analysis and purification of a fatty acyl reductase, indicate that these proteins are associated with membranes, however the enzyme responsible for the fatty acyl:fatty alcohol ligation reaction in wax biosynthesis has not been well characterized. Thus, further study and ultimately, purification of this enzyme is needed so that the gene sequences which encode the enzymatic activity may be obtained.

It is desirable, therefore, to devise a purification protocol whereby the wax synthase protein may be obtained and the amino acid sequence determined and/or antibodies specific for the wax synthase obtained. In this manner, library screening, polymerase chain reaction (PCR) or immunological techniques may be used to identify clones expressing a wax synthase protein. Clones obtained in this manner can be analyzed so that the nucleic acid sequences corresponding to wax synthase activity are identified. The wax synthase nucleic acid sequences may then be utilized in conjunction with fatty acyl reductase proteins, either native to the transgenic host cells or supplied by recombinant techniques, for production of wax esters in host cells.

Relevant Literature

Cell-free homogenates from developing jojoba embryos were reported to have acyl-CoA fatty alcohol acyl transferase activity. The activity was associated with a floating wax pad which formed upon differential centrifugation (Pollard et al. (1979) supra; Wu et al. (1981) supra).

Solubilization of a multienzyme complex from *Euglena gracilis* having fatty acyl-CoA transacylase activity is reported by Wildner and Hallick (Abstract from *The Southwest Consortium Fifth Annual Meeting*, Apr. 22–24, 1990, Las Cruces, N.Mex.).

Ten-fold purification of jojoba acyl-CoA: alcohol transacylase protein is reported by Pushnik et al. (Abstract from *The Southwest Consortium Fourth Annual Meeting*, Feb. 7, 1989, Riverside, Calif.).

An assay for jojoba acyl-CoA:alcohol transacylase activity was reported by Garver et al. (*Analytical Biochemistry* (1992) 207:335–340).

WO 93/10241 is directed to plant fatty acyl-CoA:fatty alcohol O-acyltransferases. A jojoba 57 kD protein is identified as the jojoba fatty acyl-CoA:fatty alcohol O-acyltransferase (wax synthase). The present inventors later reported that the 57 kD protein from jojoba is a β-ketoacyl-CoA synthase involved in the biosynthesis of very long chain fatty acids (Lassner et al. (*The Plant Cell* (1996) 8:281–292).

Photoaffinity labeling of a 57 kD jojoba seed polypeptide postulated to be an acyl-CoA:fatty alcohol acyltransferase was also reported by Shockey et al. (*Plant Phys.* (1995) 107:155–160).

U.S. Pat. No. 5,728,412 describes the isolation of genes encoding soluble wax synthase enzymes which are active on short chain alcohols and acetyl-CoA to produce an acetate ester.

SUMMARY OF THE INVENTION

By this invention, nucleic acid sequences encoding fatty acyl-CoA: fatty alcohol O-acyltransferase protein (fatty alcohol acyltransferase, E.C.2.3.1.75), are provided, wherein said protein is active in the formation of wax esters from fatty alcohol and fatty acyl substrates. This fatty acyl-CoA: fatty alcohol O-acyltransferase is also referred to herein as "wax synthase". The wax synthase of this invention may be active with a variety of fatty acyl and fatty alcohol substrates, including acyl-CoAs and acyl-ACPs. The carbon chain length of these substrates may vary, although a given wax synthase may show preference for acyl and alcohol substrates having a specific chain length or may be active with acyl and alcohol substrates having a wide range with respect to carbon chain length.

In general, the wax synthase of this invention has activity towards at least those acyl and alcohol substrates having a chain length of from 8 to 26 carbons, although other acyl or alcohol substrates may be tested and further activities discovered. In addition, having obtained the wax synthase protein of this invention, further manipulations are now possible as described in further detail below. These manipulations may lead to production or discovery of other related wax synthases.

In one important aspect of this invention, nucleic acid sequences are provided which encode for wax synthase. Methods are described whereby these sequences may be identified and obtained from the amino acid sequences of the wax synthase proteins of this invention. Uses of the structural gene sequences for isolation of other wax synthase sequences, as well as in recombinant constructs for transcription of wax synthase nucleic acid sequences and/or expression of wax synthase proteins in host cells are described. Uses of other nucleic acid sequences associated with wax synthase protein are also considered, such as the use of 5' and 3' noncoding regions.

Thus, this invention encompasses plant wax synthase nucleic acid sequences and the corresponding amino acid sequences, and the use of these nucleic acid sequences in the preparation of oligonucleotides containing wax synthase encoding sequences for analysis and recovery of plant wax synthase gene sequences. The plant wax synthase encoding sequence may encode a complete or partial sequence depending upon the intended use. All or a portion of the genomic sequence, or cDNA sequence, is intended.

Of special interest are recombinant DNA constructs which provide for transcription or transcription and translation (expression) of the plant wax synthase sequences. In particular, constructs which are capable of transcription or transcription and translation in plant host cells are preferred. For some applications a reduction in plant wax synthase may be desired. Thus, recombinant constructs may be designed having the plant wax synthase sequences in a reverse orientation for expression of an anti-sense sequence or use of co-suppression, also known as "transwitch", constructs may be useful. Such constructs may contain a variety of regulatory regions including transcriptional initiation regions obtained from genes preferentially expressed in plant seed tissue. For some uses, it may be desired to use the transcriptional and translational initiation regions of the wax synthase gene either with the wax synthase encoding sequence or to direct the transcription and translation of a heterologous sequence.

In yet a different aspect, this invention relates to a method for producing a wax synthase in a host cell or progeny thereof via the expression of a construct in the cell. Cells containing a wax synthase as a result of the production of the plant wax synthase encoding sequence are also contemplated herein. Such constructs may employ other nucleic acid sequences which encode for proteins involved in the production of wax esters and/or various fatty,acyl species.

Further, it may be recognized that the wax synthases of this invention may find application in the production of wax esters in such host cells which contain fatty acyl and fatty alcohol substrates of the wax synthase. Such host cells may exist in nature or be obtained by transformation with nucleic acid constructs which encode a fatty acyl reductase. Fatty acyl reductase, or "reductase", is active in catalyzing the reduction of a fatty acyl group to the corresponding alcohol. Co-pending U.S. patent application Ser. No. 07/659,975 (filed Feb. 22, 1991), Ser. No. 07/767,251 (filed Sep. 27, 1991) and Ser. No. 07/920,430 (filed Jul. 31, 1992), which are hereby incorporated by reference, are directed to such reductase proteins. This information is also provided in published PCT patent application WO 92/14816. In addition, other sources of wax synthase proteins are described herein which are also desirable sources of reductase proteins.

Especially considered in this aspect of the invention, are plant cells which contain the preferred alcohol substrates of a jojoba wax synthase described herein. A method of providing plant cells with such alcohol substrates is considered wherein said cells are transformed with recombinant nucleic acid constructs which encode a fatty acyl reductase nucleic acid sequence. Thus, plant hosts which do not normally contain significant amounts of the alcohol substrates utilized by wax synthase, may be transformed with a reductase construct such that the alcohols are produced. In this manner, the fatty acyl groups present in the host cell will also provide the source of fatty alcohol substrate utilized by wax synthase in the synthesis of wax esters. Depending on the specificities of the wax synthase and reductase proteins, one recognizes that in this manner, plant cells may be obtained which produce a variety of desirable wax ester products. Such products will have different properties depending on the chain length and degree of saturation of the fatty alcohol and fatty acyl groups. Thus, the wax ester products produced according to the methods herein may be recovered from the host cells and are also considered in this invention.

Also considered in this invention are the modified plants, seeds and wax esters obtained by expression of the plant wax synthase sequences and proteins of this invention.

BRIEF DESCRIPTION OF THE DRAWINGS

FIG. 1A provides results of hydroxyapatite chromatography.

FIG. 2 presents results of analysis of wax synthase activity in column fractions from a second wax synthase purification protocol.

FIG. 3 provides the nucleotide sequence of the PCR product from primers WSPEP14-F1 and WSPEP33-R2 (FIG. 3A) (SEQ ID NO: 39) and the complete nucleotide sequence of a fatty acyl-CoA:fatty alcohol O-acyltransferase from jojoba inferred from 5' and 3' RACE products (FIG. 3B) (SEQ ID NO: 40).

FIG. 10 provides the nucleic acid sequence of jojoba wax synthase (SEQ ID NO: 41).

FIG. 11 provides the amino acid sequence obtained from the nucleic acid sequence of FIG. 10 (SEQ ID NO: 42).

FIG. 12 provides the nucleic acid sequence of AT_WS1 (SEQ ID NO: 43).

FIG. 13 provides the nucleic acid sequence of AT_WS2 (SEQ ID NO: 44).

FIG. 14 provides the nucleic acid sequence of AT_WS3 (SEQ ID NO: 45).

FIG. 15 provides the nucleic acid sequence of AT_WS4 (SEQ ID NO: 46).

FIG. 16 provides the nucleic acid sequence of AT_WS5 (SEQ ID NO: 47).

FIG. 17 provides the nucleic acid sequence of AT_WS6 (SEQ ID NO: 48).

FIG. 18 provides the nucleic acid sequence of AT_WS7 (SEQ ID NO: 49).

FIG. 19 provides an alignment between the amino acid sequences of the jojoba wax synthase, and Arabidopsis AT_WS1, AT_WS2, AT_WS3, AT_WS4, AT_WS5, AT_WS6, and AT_WS7.

FIG. 20 provides a dendogram of the relationships between the amino acid sequences compared in FIG. 19.

DETAILED DESCRIPTION OF THE INVENTION

Figure 1A:
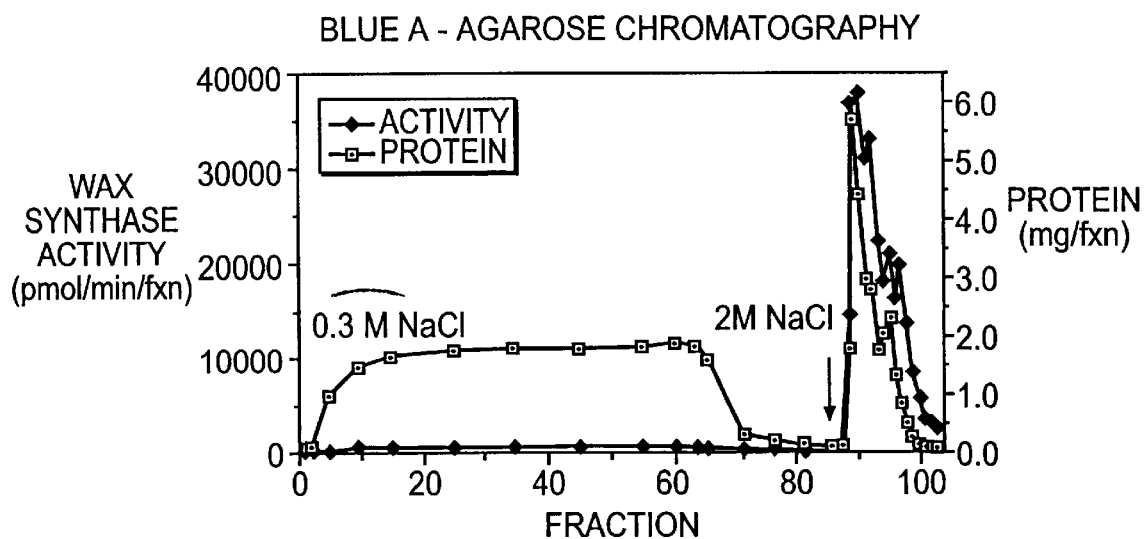
FIG. 1A provides results of Blue A agarose chromatography.
Figure 1B:
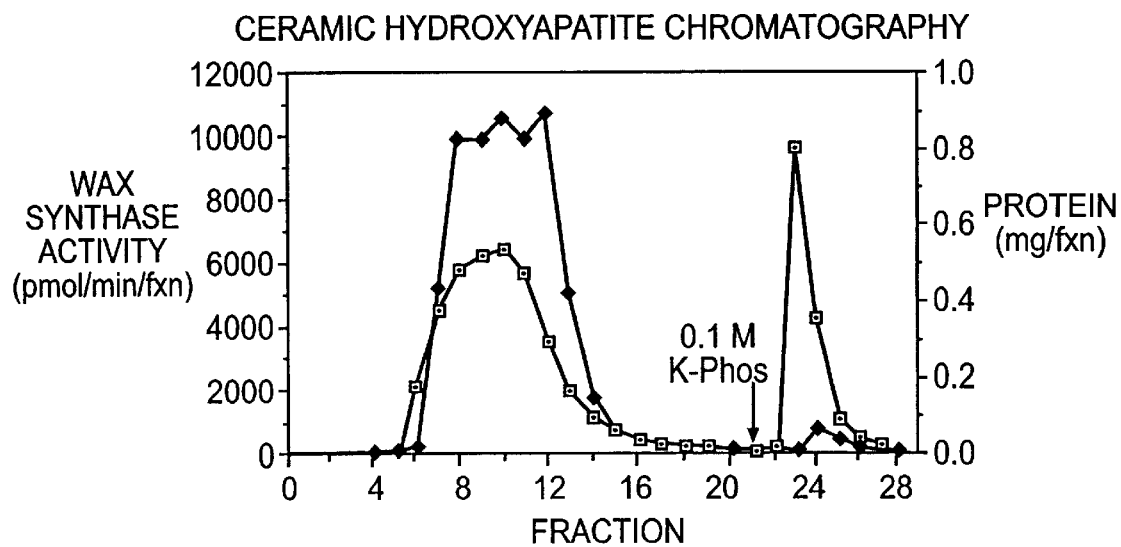
FIG. 1B provides results of ceramic hydroxyapatite chromatography.
Figure 1C:
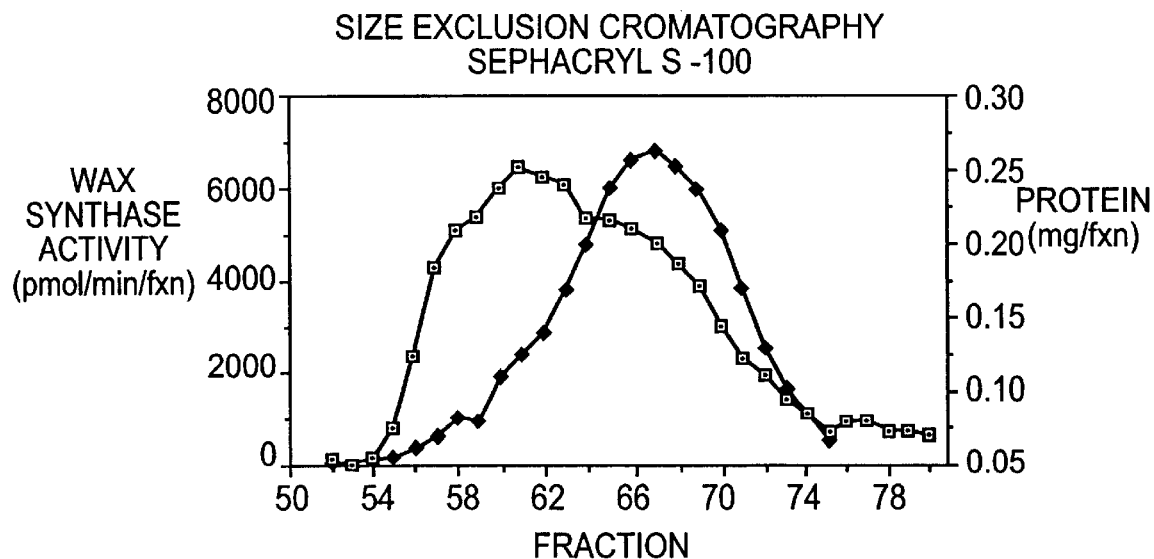
FIG. 1C provides results of Sephracryl S-100 size exclusion chromatography.
Figure 1D:
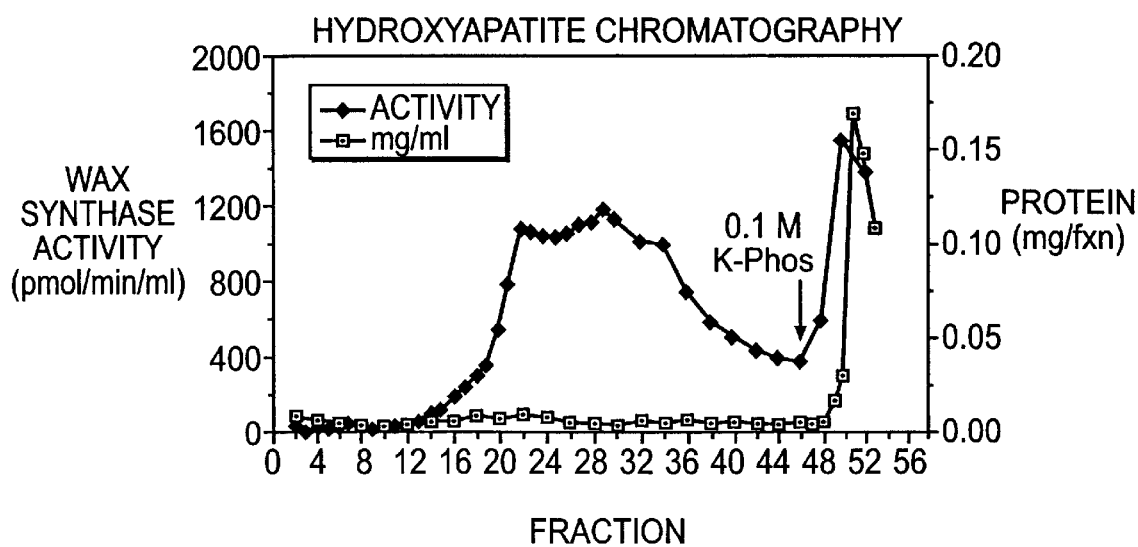
FIG. 1 presents results of analysis of wax synthase activity in column fractions from a first wax synthase purification protocol.

In accordance with the subject invention, nucleic acid sequences are provided which encode for amino acids, such as a protein, polypeptide or peptide fragment, which are active in catalyzing the esterification of a fatty alcohol by a fatty acyl group to produce a wax ester. Such proteins are known as fatty acyl-CoA: fatty alcohol acyltransferase (E.C.2.3.1.75). The acyl-CoA: alcohol acyltransferase of this invention is also referred to hereafter as "wax synthase".

Although typically referred to as an acyl-CoA: alcohol acyltransferase, the wax synthases of this invention may demonstrate activity towards a variety of acyl substrates, including fatty acyl-CoA and fatty acyl-ACP molecules. In addition, both the acyl and alcohol substrates acted upon by the wax synthase may have varying carbon chain lengths and degrees of saturation, although the wax synthase may demonstrate preferential activity towards certain molecules.

Many different organisms produce wax esters from alcohol and acyl substrates and are desirable sources of a wax synthase protein of this invention. For example, plants produce epidermal, or cuticular wax (Kolattukudy (1980) in The *Biochemistry of Plants* (Stumpf, P. K. and Conn, E. E., eds.) Vol. 4, p. 571–645), and the desert shrub, jojoba (Ohlrogge et al. (*Lipids* (1978) 13:203–210), as well as *Murraya koenigii* (Kartha, (1969) *Chemistry and Industry* 4:1342–1343 and Kartha, et al. (1972) *Chemistry and Industry* 891–892), produce a seed storage wax. Wax synthesis has also been observed in various species of bacteria, such as *Acinetobacter* (Fixter et al. (1986) *J. Gen. Microbiol.* 132:3147–3157) and *Micrococcus* (Lloyd (1987) *Microbios* 52:29–37), and by the unicellular orgnanism, Euglena (Khan and Kolattukudy (1975) *Arch. Biochem. Biophys.* 170:400–408). In addition, wax production and wax synthase activity have been reported in microsomal preparations from bovine meibomian glands (Kolattukudy et al. (1986) *J. Lipid Res.* 27:404–411), avian uropygial glands, and various insect and marine organisms. Consequently, many different wax esters which will have various properties may be produced by the wax synthases of this invention, and the activity of the enzyme and type of wax ester produced may depend upon the available substrate or the substrate specificity of the particular wax synthase of interest.

To obtain a reliable source of a wax synthase protein for use in esterification reactions, it is desirable to isolate nucleic acid sequences associated with the wax synthase such that these sequences may be cloned into host cells for the production of the wax synthase enzyme. For example, one may clone nucleic acid sequences encoding a wax synthase protein into vectors for expression in *E. coli* cells to provide a ready source of the wax synthase protein. The wax synthase protein so produced may also be used to raise antibodies against wax synthase proteins for use in identification and purification of related wax synthase proteins from various sources, especially from plants. In addition, further study of the wax synthase protein may lead to site-specific mutagenesis reactions to further characterize and improve its catalytic properties or to alter its fatty alcohol or fatty acyl substrate specificity. A wax synthase with altered substrate specificity may find application in conjunction with other FAS enzymes.

Prior to the instant invention, nucleic acid and amino acid sequences of wax synthase proteins were not known. Thus, in order to obtain the nucleic acid sequences associated with wax synthase, it was necessary to first purify the protein from an available source and determine at least partial amino acid sequence so that appropriate probes useful for isolation of wax synthase nucleic acid sequences could be prepared.

The desert shrub, *Simmondsia chinensis* (jojoba) was identified as a source of a candidate wax synthase protein. Initial studies reveal that the jojoba wax synthase is an integral membrane protein and hydrophobic in nature. In general, membrane associated proteins are difficult to purify as they tend to lose enzymatic activity when they are solubilized, i.e. separated from the membrane environment in which they normally function. Techniques that have been used to solubilize integral membrane proteins include addition of detergents or organic solvents to a preparation of a suitable membrane fraction. Further conventional purification techniques, such as precipitation, ion-exchange, gel-filtration and affinity chromatography may then be utilized, assuming the desired protein still retains functional activity that can be measured using a specific enzymatic assay.

Typically, as a first step towards obtaining a solubilized membrane protein, a microsomal membrane preparation which comprises wax synthase activity is desired. Standard microsomal membrane preparations utilize differential centrifugation of a cell-free homogenate (CFH) to yield a membrane fraction which is free of whole cells, nuclei and soluble protein. (See, for example Mooré et al. (1987) *Biological Membranes: A Practical Approach*, pp. 37–72, eds. Finalay and Evans.) With oilseeds, initial centrifugation steps typically yield a pellet, supernatant and a floating fat pad, and microsomal membranes may then be recovered by further centrifugation of the supernatant.

A protocol is described in U.S. Pat. No. 5,403,918, whereby a jojoba membrane fraction was obtained with good recovery of enzyme activity associated with fatty acyl reductase, another enzyme involved in the formation of wax esters in jojoba. The method also provides membrane fractions having wax synthase activity as described in detail in the examples which follow. In addition, microsomal membrane preparations from jojoba are also described in Lassner et al. (supra). Other procedures are known to those in the art and may be utilized to obtain similar membrane preparations. In addition, methods to assay for wax synthase activity in such preparations are described in Example 1.

A critical stage for further enzyme characterization and purification is that of obtaining solubilized wax synthase protein that is separated from its native lipid bilayer membrane environment, but retains substantial amounts of measurable wax synthase enzymatic activity. The removal of integral membrane proteins from the lipid bilayer is typically accomplished using amphiphilic detergents in aqueous solution, although organic solvents have also been used in a few cases. Many different detergents and methods of solubilization of membrane proteins are known to those skilled in the art, and are also reviewed by Neugebauer (Methods Enzymol. (1990) 182:239–253) and Hjelmiland (*Methods Enzymol.* (1990) 182:253–264).

Often, detergents which are used to solubilize membrane proteins are found to inhibit the enzymatic activity of a desired protein. Several detergents were tested for solubilization of jojoba wax synthase, including CHAPS (3-[(3-cholamidopropyl)-dimethyl-ammonio]-1-propanesulfonate), which was demonstrated in U.S. Pat. No. 5,403,918 to be useful in purification of a fatty acyl reductase from jojoba. All were found to inhibit wax synthase enzymatic activity. Although strong inhibition by CHAPS was observed at concentrations above the CMC, it was found that addition of phospholipids, such as L-phosphatidyl choline, and adjustment of the CHAPS concentration from 1.0% to 0.2%, i.e. to below the CMC, results in reconstitution of a portion of the wax synthase activity. The primary requirement for reconstitution of wax synthase activity is the presence of phospholipids during the removal or dilution of the detergent, so that the wax synthase protein is incorporated into phospholipid vesicles. This differs from the protocol developed for reconstitution of jojoba reductase activity, which does not require addition of phospholipids. Thus, if phospholipids are present in a wax synthase preparation, such as that from a microsomal membrane fraction, activity may be detected simply by removal or dilution of detergent. However, in further purified wax synthase preparations, phospholipids must be added to detect activity. Optimum activity recovery is obtained when a ratio of CHAPS to PL is 2.8/1 (w/w) in the assay. A method to reconstitute and assay wax synthase activity in solubilized wax synthase preparations is described in Example 1.

Having obtained solubilized wax synthase protein, it can be seen that further experiments to characterize the enzyme as to substrate specificity, cofactor requirements and possible activity inhibiting agents may now be conducted. For example, it has been found that the jojoba wax synthase of this invention has a broad range of acyl substrates, including acyl-ACP and acyl-CoA molecules. In addition, the acyl and fatty alcohol substrates may have a broad size range with respect to carbon chain length. For example, activity was tested using substrates having carbon chain lengths of from C12 to C24, and all were shown to be utilized by the enzyme. In addition, activity was shown with fatty acyl and fatty alcohols having varying degrees of unsaturation.

Chromatography techniques may be utilized to provide enriched preparations of plant wax synthase. One such purification step involves chromatography over an immobilized reactive dye matrix, such as the Cibacron Blue F3GA (Blue A) used in this invention. The jojoba wax synthase activity binds to such a column when loaded in a buffer containing approximately 0.3M NaCl, while greater than approximately 85% of other protein passes through or is removed in subsequent washes. As described in U.S. Pat. No. 5,403,918, reductase activity is also bound to the Blue A column under such conditions. It is demonstrated herein that approximately 70% of the wax synthase activity loaded to a Blue A column can be recovered by elution with a 2.0M NaCl buffer wash. The jojoba reductase and β-ketoacyl-CoA synthase (KCS) proteins are also present in this Blue A eluate.

Further purification of the Blue A eluate is obtained by loading the sample onto a cyrstalline hydroxyapatite (HA) column. Wax synthase activity does not bind to the column and is found in the flow through and wash. The majority of the reductase and KCS activities bind to the column, as does the majority of the protein in the sample. The HA fraction enriched in wax synthase activity can be used for size exclusion chromatography, and using a Superdex 75 size exclusion column, the jojoba wax synthase protein is estimated to have a molecular weight of 48 kD.

Using such purification techniques, the jojoba wax synthase protein can be recovered as a substantially purified protein preparation and the amino acid sequence can be obtained. Similarly, due to the hydrophobic nature of the fatty alcohol substrates of wax synthase enzymes, other wax synthases would also be predicted to be associated with membranes in their native cells, and thus purification techniques described herein for jojoba wax synthase, may also be useful in recovery of purified preparation of other wax synthase proteins.

For example, *Euglena gracilis* produces waxes through the enzymatic actions of a fatty acyl-CoA reductase and a fatty acyl-CoA alcohol transacylase, or wax synthase. Typically, waxes having carbon chain lengths ranging from 24–32 are detected in this organism. As described above for jojoba, the Euglena wax synthase enzyme may be solubilized using a CHAPS/NaCl solution, and a partially purified wax synthase preparation is obtained by dye-ligand, HA and size exclusion chromatography.

Acinetobacter species are also known to produce wax ester compositions, although the mechanism is not well defined. As described herein a fatty acyl-CoA alcohol transacylase, or wax synthase activity is detected in Acinetobacter species. The wax synthase activity is solubilized in CHAPS/NaCl, enriched by Blue A column chromatography and may be further purified using such techniques as size exclusion chromatography.

In order to obtain nucleic acid sequences encoding the wax synthase of the present invention, the band containing the purified protein is cut out of an SDS gel to use in amino acid sequencing reactions. In gel digestion was used as opposed to more convenient methods, such as transfer of the protein to nitrocellulose or polyvinylidenedifluoride (PVDF) membranes due to the fact that conditions under which the jojoba wax synthase protein could be blotted and bound to such membranes have not been discovered. A commercial laboratory, W. M. Keck Foundation/Yale University, was provided with gel slices containing purified jojoba wax synthase protein for use in determining amino acid sequences of the jojoba protein by in-gel digest and subsequent protein sequencing. The peptide sequences generated in this manner may be used in PCR gene isolation techniques and cDNA library screening as described in more detail in the following examples.

Further experiments to confirm the identity of the wax synthase may also be desirable, such as expression of the protein in *E. coli*. The wax synthase may then act on fatty acyl and fatty alcohol substrates in such cells to produce wax esters which may be detected by various analytical methods. If the host cells do not contain the alcohol substrate of the wax synthase, activity may be verified by assaying cell extracts. Alternatively, wax synthase protein may be prepared by in vitro translation using wax synthase nucleic acid sequences and commercially available translation kits. Addition of microsomal membrane preparations to the in vitro translation sample may be necessary to obtain active wax synthase protein if membrane insertion is critical to activity. Other testing may include immunological assays, whereby antibodies specific for the candidate protein are prepared and found to inhibit wax synthase activity in protein preparations.

Thus, as described in more detail in the examples below, nucleic acid sequences are isolated using amino acid sequences determined for the proteins associated with wax synthase activity, both to confirm the identity of a wax synthase protein and to provide for. transcription of the sequences and/or expression of the protein in host cells, either prokaryotic or eukaryotic.

As the wax synthase is a membrane bound protein, it may be desirable to express a candidate protein in a plant cell in order to verify the activity. Electroporation or bombardment of plant tissue for transient expression may be useful for this purpose. Ultimately, stable plant expression in a plant which produces substrates recognized by this enzyme is desired. If a plant targeted for transformation with wax synthase sequences does not naturally contain the fatty alcohol and fatty acyl ester substrates of this enzyme, a plant extract may be prepared and assayed for wax synthase activity by adding substrates of the wax synthase to the extract. Constructs and methods for transformation of plant hosts with wax synthase sequences are discussed in more detail below.

The wax synthase nucleic acids of this invention may be genomic or cDNA and may be isolated from cDNA or genomic libraries or directly from isolated plant DNA. As described in more detail in the examples below, a method for obtaining nucleic acid sequence for the jojoba wax synthase by PCR from primers specific for the disclosed jojoba wax synthase peptides is provided herein.

Wax synthase nucleic acid sequences of this invention include those corresponding to the jojoba wax synthase protein, as well as sequences obtainable from the jojoba protein or nucleic acid sequences. By "corresponding" is meant nucleic acid sequences, either DNA or RNA, including those which encode jojoba wax synthase protein or a portion thereof, regulatory sequences found 5' or 3' to said encoding sequences which direct the transcription or transcription and translation (expression) of the wax synthase in jojoba embryos, intron sequences not present in the cDNA, as well as sequences encoding any leader or signal peptide of a precursor wax synthase protein that may be required for insertion or retention into the endoplasmic reticulum membrane, which may or may not be found in the mature wax synthase enzyme.

By sequences "obtainable" from the jojoba sequence or protein, is intended any nucleic acid sequences associated with a desired wax synthase protein that may be synthesized from the jojoba wax synthase amino acid sequence, or alternatively identified in a different organism, and isolated using as probes jojoba wax synthase nucleic acid sequences or antibodies prepared against the jojoba wax synthase protein. In this manner, it can be seen that sequences of these other wax synthases may similarly be used to isolate nucleic acid sequences associated with wax synthase proteins from additional sources.

For isolation of nucleic acid sequences, cDNA or genomic libraries may be prepared using plasmid or viral vectors and techniques well known to those skilled in the art. Useful nucleic acid hybridization and immunological methods that may be used to screen for the desired sequences are also well known to those in the art and are provided, for example in Maniatis, et al. (*Molecular Cloning: A Laboratory Manual*, Second Edition (1989) Cold Spring Harbor Laboratory, Cold Spring Harbor, N.Y.

Typically, a sequence obtainable from the use of nucleic acid probes will show 60–70% sequence identity between the target sequence and the given sequence encoding a wax synthase enzyme of interest. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Oligonucleotide probes can be considerably shorter than the entire nucleic acid sequence encoding a wax synthase enzyme, but should be at least about 10, preferably at least about 15, and more preferably at least about 20 nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, either Northern or Southern blots (to screen desired sources for homology), or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. *(Methods in Enzymology* (1983) 100:266–285).

A useful probe and appropriate hybridization and washing conditions having been identified as described above, cDNA or genomic libraries are screened using the labeled sequences and optimized conditions. The libraries are first plated onto a solid agar medium, and the DNA lifted to an appropriate membrane, usually nitrocellulose or nylon filters. These filters are then hybridized with the labeled probe and washed as discussed above to identify clones containing the related sequences.

For immunological screening, antibodies to the jojoba wax synthase can be prepared by injecting rabbits or mice with the purified protein. Methods of preparing antibodies are well known to those in the art, and companies which specialize in antibody production are also available. Either monoclonal or polyclonal antibodies can be produced, although typically polyclonal antibodies are more useful for gene isolation.

To screen desired plant species, Western analysis is conducted to determine that a related protein is present in a crude extract of the desired plant species, that cross-reacts with the antibodies to the jojoba wax synthase. This is accomplished by immobilization of the plant extract proteins on a membrane, usually nitrocellulose, following electrophoresis, and incubation with the antibody. Many different systems for detection of the antibody/protein complex on the nitrocellulose filters are available, including radiolabeling of the antibody and second antibody/enzyme conjugate systems. Some of the available systems have been described by Oberfelder (*Focus* (1989) BRL/Life Technologies, Inc. 11:1–5). If initial experiments fail to detect a related protein, other detection systems and blocking agents may be utilized. When cross-reactivity is observed, genes encoding the related proteins can be isolated by screening expression libraries representing the desired plant species. Expression libraries can be constructed in a variety of commercially available vectors, including lambda gt11, as described in Maniatis, et al. (supra).

The clones identified as described above using DNA hybridization or immunological screening techniques are then purified and the DNA isolated and analyzed using known techniques. In this manner, it is verified that the clones encode a related wax synthase protein. Other wax synthases may be obtained through the use of the "new" wax synthase in the same manner as the jojoba wax synthase was used.

Alternatively, databases containing nucleic acid and amino acid sequences from various organisms may be searched with the sequences of the present invention to identify similar sequences. Surprisingly, using the jojoba wax synthase protein sequence to search a database containing DNA sequences from Arabidopsis, an approximately 12 Kb sequence containing at least seven repeats of an open reading frame with high similarity to the jojoba sequence are identified. The deduced amino acid sequences demonstrate a high level of homology to the jojoba wax synthase amino acid sequence. For example, amino acid sequence comparisons between jojoba wax synthase and the sequences obtained from the Arabidopsis homologues reveals an identity ranging from about 36% to about 44% between the amino acids. Thus, as shown herein, homologous similarity (identity+similarity) of at least 52% is shown in protein sequence comparisons between the jojoba and Arabidopsis sequences.

It will be recognized by one of ordinary skill in the art that wax synthase nucleic acid sequences of this invention may be modified using standard techniques of site specific mutation or PCR, or modification of the sequence may be accomplished in producing a synthetic nucleic acid sequence. These modified sequences are also considered wax synthase nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of a wax synthase enzyme of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the wax synthase protein) may be synthesized using codons preferred by a selected host. Host-preferred codons may be determined, for example, from the codons used most frequently in the proteins expressed in a desired host species.

The nucleic acid sequences associated with wax synthase proteins will find many uses. For example, recombinant constructs can be prepared which can be used as probes or will provide for expression of the wax synthase protein in host cells. Depending upon the intended use, the constructs may contain the sequence which encodes the entire wax synthase, or a portion thereof. For example, critical regions of the wax synthase, such as an active site may be identified. Further constructs containing only a portion of the wax synthase sequence which encodes the amino acids necessary for a desired wax synthase activity may thus be prepared.

Useful systems for expression of the wax synthase sequences of this invention include prokaryotic cells, such as *E. coli*, yeast cells, and plant cells, both vascular and nonvascular plant cells being desired hosts. In this manner, the wax synthase protein may be produced to allow further studies, such as site-specific mutagenesis of encoding sequences to analyze the effects of specific mutations on reactive properties of the wax synthase protein.

The DNA sequence encoding a wax synthase of this invention may be combined with foreign DNA sequences in a variety of ways. By "foreign" DNA sequences is meant any DNA sequence which is not naturally found joined to the wax synthase sequence, including DNA sequences from the same organism which are not naturally found joined to wax synthase sequences. Both sense and antisense constructs utilizing wax synthase encoding sequences are considered, wherein sense sequence may be used for expression of wax synthase in a host cell, and antisense sequences may be used to decrease the endogenous levels of a homologous wax synthase protein naturally produced by a target organism. In addition, the wax synthase gene sequences of this invention may be employed in a foreign host in conjunction with all or part of the sequences normally associated with the wax synthase, such as regulatory or membrane targeting sequences.

In its component parts, a DNA sequence encoding wax synthase is combined in a recombinant construct having, in the 5' to 3' direction of transcription, a transcription initiation control region capable of promoting transcription and translation in a host cell, the nucleic acid sequence encoding wax synthase and a transcription termination region. Depending upon the host, the regulatory regions will vary, and may include regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, the recombinant constructs will involve regulatory regions functional in plants which provide for expression of the wax synthase gene to produce functional wax synthase protein. The open reading frame, coding for the plant wax synthase or a functional fragment thereof will be joined at its 5' end to a transcription initiation regulatory region such as the wild-type sequence naturally found 5' upstream to the wax synthase structural gene. Numerous other promoter regions from native plant genes are available which provide for a wide variety of constitutive or regulatable expression of structural gene sequences.

In addition to sequences from native plant genes, other sequences can provide for constitutive gene expression in plants, such as regulatory regions associated with Agrobacterium genes, including regions associated with nopaline synthase (Nos), mannopine synthase (Mas), or octopine synthase (Ocs) genes. Also useful are regions which control expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, and the like.

In embodiments wherein the expression of the wax synthase protein is desired in a plant host, the use of all or part of the complete plant wax synthase gene may be desired, namely the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source or enhanced promoters, such as double 35S CaMV promoters, the sequences may be joined together using standard techniques. Additionally, 5' untranslated regions from highly expressed plant genes may be useful to provide for increased expression of the wax synthase proteins described herein.

The DNA constructs which provide for wax synthase expression in plants may be employed with a wide variety of plant life, particularly, plants which produce the fatty acyl-CoA substrates of the wax synthase enzyme, such as Brassica. Other plants of interest produce desirable fatty acyl substrates, such as medium or long chain fatty acyl molecules, and include but are not limited to rapeseed (Canola varieties), sunflower, safflower, cotton, Cuphea, soybean, peanut, coconut and oil palms, and corn. Of particular interest is the use of such constructs in high erucic acid varieties of rapeseed Brassica (HEAR) for production of long-chain liquid waxes. Further uses envisioned for HEAR plants includes the production of varieties containing substantially increased levels of erucic acid as the result of providing an additional wax "sink" for the erucic acid, which is normally stored in the seed TAG.

As to the fatty alcohol substrate of the wax synthase enzyme, other than jojoba, seed plants are not known to produce large quantities of fatty alcohols, although small amounts of this substrate may be available to the wax synthase enzyme. Therefore, in conjunction with the wax synthase constructs of this invention, it is desirable to provide the target host cell with the capability to produce fatty alcohols from the fatty acyl molecules present in the host cells. For example, a plant fatty acyl reductase and methods to provide for expression of the reductase enzymes in plant cells are described in U.S. Pat. No. 5,370,996. The nucleic acid sequence and translated amino acid sequence of the jojoba reductase is provided in FIG. 1 of that patent. Thus, by providing both the wax synthase and reductase proteins to the host plant cell, wax esters may be produced from the fatty alcohol and fatty acyl substrates. Furthermore, expression of β-ketoacyl-CoA synthase in conjunction with expression of wax synthase and reductase proteins is considered in the present invention. In this manner, the production of very long chain fatty acid substrates of these enzymes may be increased in the target plant species.

In addition to the jojoba reductase, reductase enzymes from other organisms may be useful in conjunction with the wax synthases of this invention. Other potential sources of reductase enzymes include Euglena, Acinetobacter, Micrococus, certain insects and marine organisms, and specialized mammalian or avian tissues which are known to contain wax esters, such as bovine meibomian glands or ovian uropygial glands. Other potential sources of reductase proteins may be identified by their ability to produce fatty alcohols or, if wax synthase is also present, wax esters.

The wax synthase and reductase sequences may be provided during the same transformation event, or alternatively, two different transgenic plant lines, one having wax synthase constructs and the other having reductase constructs may be produced by transformation with the various constructs. These plant lines may then be crossed using known plant breeding techniques to provide wax synthase and reductase containing plants for production of wax ester products.

Furthermore, other nucleic acid sequences encoding for enzymes involved in the formation of very long chain fatty acids may also find use in the DNA constructs of the present invention for the production of wax esters in a plant host. Such nucleic acid sequences are known in the art and are as described in U.S. Pat. No. 5,679,881. For example, as described in the examples below, the wax synthase of the present invention is used in plant expression constructs in conjunction with nucleic acid sequences encoding for a fatty acid elongase (described in U.S. Pat. No. 5,679,881, the entirety of which is incorporated herein by reference) and an acyl-CoA reductase (described in U.S. Pat. No. 5,403,918, the entirety of which is incorporated herein by reference). Such plant expression constructs provide for the production of wax esters in transgenic *Arabidopsis thaliana* plants.

For applications leading to wax ester production, 5' upstream non-coding regions obtained from genes regulated during seed maturation are desired, especially those preferentially expressed in plant embryo tissue, such as regions derived from ACP, oleosin (Lee and Huang (1991) *Plant Physiol.* 96:1395–1397) and napin regulatory regions. Transcription initiation regions which provide for preferential expression in seed tissue, i.e., which are undetectable in other plant parts, are considered desirable for wax ester production in order to minimize any disruptive or adverse effects of the gene product in other plant parts. Further, the seeds of such plants may be harvested and the lipid reserves of these seeds recovered to provide a ready source of wax esters. Thus, a novel seed product may be produced in oilseed plants which, absent transformation with wax synthase constructs as described herein, are not known to produce wax esters as a component of their seed lipid reserves.

Such "seed-specific promoters" may be obtained and used in accordance with the teachings of U.S. Pat. No. 5,420,034, and U.S. Pat. No. 5,430,194. In addition, where plant genes, such as the jojoba reductase and wax synthases are expressed, it may be desirable to use the entire plant gene, including 5' and 3' regulatory regions and any introns that are present in the encoding sequence, for expression of the jojoba genes in a transformed plant species, such as Arabidopsis or Brassica.

Regulatory transcription termination regions may be provided in recombinant constructs of this invention as well. Transcription termination regions may be provided by the DNA sequence encoding the plant wax synthase or a convenient transcription termination region derived from a different gene source, especially the transcription termination region which is naturally associated with the transcription initiation region. The transcript termination region will contain at least about 0.5 kb, preferably about 1–3 kb of sequence 3' to the structural gene from which the termination region is derived.

Where expression of the wax synthase, as well as other genes involved in wax synthesis, is to be directed in other plant tissues, additional promoters may find use in the constructs of the present invention. For example, where preferential expression of the genes in the pollen is desired, promoter regions, for example, Rop1At (Li, et al. (1998) *Plant Phyiol.* 118:407–417) and others described by Hamilton, et al. (1998) *Plant Mol Biol.* 38(4)663–669 may be employed. Where preferential expression in the epidermis is desired, promoter regions such as Ntltp1 (Canevascini, et al. (1996) *Plant Physiol.* 112:513–524) may be employed.

Additional plant gene regions may be used to optimize expression of wax synthase and reductase genes in plant tissues. For example, 5' untranslated regions of highly expressed genes, such as that of the small subunit (SSU) of RuBP-carboxylase, inserted 5' to DNA encoding sequences may provide for enhanced translation efficiency. Portions of the SSU leader protein encoding region (such as that encoding the first 6 amino acids) may also be used in such constructs. In addition, for applications where targeting to plant plastid organelles is desirable, transit peptide encoding sequences from SSU or other nuclear-encoded chloroplast proteins may be used in conjunction with wax synthase and reductase sequences.

Depending on the method for introducing the DNA expression constructs into the host cell, other DNA sequences may be required. Importantly, this invention is applicable to dicotyledons and monocotyledons species alike and will be readily applicable to new and/or improved transformation and regeneration techniques.

In developing the recombinant construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the recombinant construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Similarly, genes encoding enzymes providing for production of a compound identifiable by color change, such as GUS, or luminescence, such as luciferase are useful. Depending upon the number of different host species the expression construct or components thereof are introduced, one or more markers may be employed, where different conditions for selection are used for the different hosts.

In addition to the sequences providing for transcription of wax synthase sequences, the DNA constructs of this invention may also provide for expression of an additional gene or genes, whose protein product may act in conjunction with the wax synthase to produce a valuable end product. For example, as discussed above, DNA constructs which provide for expression of wax synthase and a fatty acyl reductase so that wax esters may produced in transformed hosts, are considered in this invention. The constructs may also provide for the expression of a third gene encoding, for example β-ketoacyl-CoA synthase (KCS). Furthermore, production of different wax esters having varying carbon chain lengths and degrees of saturation is desired and may be provided by transforming host plants having fatty alcohol or fatty acyl substrates of varying chain lengths. Such plants may be provided, for example, by methods described in the published international patent application number PCT WO 91/16421, which describes various thioesterase genes and methods of using such genes to produce fatty acyl substrates having varying chain lengths in transformed plant hosts.

Furthermore, to optimize the production of wax esters in oilseed plant hosts, one may wish to decrease the production of the triacylglyceride oils that are normally produced in the seeds of such plants. One method to accomplish this is to antisense a gene critical to this process, but not necessary for the production of wax esters. Such gene targets include diacylglycerol acyltransferase, and other enzymes which catalyse the synthesis of triacylglycerol. Additionally, it may be desirable to provide the oilseed plants with enzymes which may be used to degrade wax esters as a nutrient source, such as may be isolated from jojoba or various other wax producing organisms. In this manner, maximal production of wax esters in seed plant hosts may be achieved.

In addition, by engineering wax synthesis systems into plants which normally do not produce wax, it may be possible to increase the production of novel fatty acids. For example, there may be intrinsic limitations in oilseed triacylglyceride and phospholipid synthesis which prefer specific fatty acids for a given position on the glycerol backbone. Therefore, plants engineered to produce a given "exotic" fatty acid may be limited in the amount of that fatty acid produced due to the limitations of positions on the glycerol backbone. Thus, by introducing a wax synthesis system into a plant, it may be possible to increase the amount of an "exotic" fatty acid produced by providing an alternative fatty acid sink. Furthermore, it is also possible to increase the amount of an "exotic" fatty acid using a wax synthesis system derived from a source which accumulates wax esters which are composed of such fatty acids. For example, by utilizing a wax synthase from Euglena, it is possible to increase the amount of C12 fatty acids.

Furthermore, the introduction of a wax synthesis system into oil producing plants may allow for a further increase in the amount of oil produced as a component of the host cell. By expressing a wax synthesis system in an oil producing plant tissue, such as an oil seed, it is possible to further increase the amount of oil produced in such a tissue, by utilizing the native oil production, such as through triacylglycerol synthesis, and the introduced wax synthesis.

The wax esters produced in the methods described herein may be harvested using techniques for wax extraction from jojoba or by various production methods used to obtain oil products from various oilseed crops. The waxes thus obtained will find application in many industries, including pharmaceuticals, cosmetics, detergents, plastics, and lubricants. Applications will vary depending on the chain length and degree of saturation of the wax ester components. For example, long chain waxes having a double bond in each of the carbon chains are liquid at room temperature, whereas waxes having saturated carbon chain components, may be solid at room temperature, especially if the saturated carbon chains are longer carbon chains.

Furthermore, production of transgenic plants which produce wax esters in the epidermal cell layer provides for enhanced tolerance to various environmental stresses, such as drought tolerance, as well as pathogen and insect tolerances. Such roles for epicuticular waxes are known in the art, and are reviewed, for example, by Post-Beittenmiller (1996) *Annu. Rev. Plant Physiol. Plant Mol. Biol.* 47:405–430 and Jeffree (1986) *Insects and the Plant Surface* (Southwood and Juniper, eds.) 23–64 (Edward Arnold).

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. Other sequences useful in providing for transfer of nucleic acid sequences to host plant cells may be derived from plant pathogenic viruses or plant transposable elements. In addition, techniques of microinjection, DNA particle bombardment, electroporation have been developed which allow for the transformation of various monocot and dicot plant species.

The invention now being generally described, it will be more readily understood by reference to the following examples, which are included for purposes of illustration only and are not intended to limit the invention unless so stated.

EXAMPLES

Example 1

Wax Synthase Assays

Methods to assay for wax synthase activity in microsomal membrane preparations or solubilized protein preparations are described.

A. Radiolabeled Material

The substrate generally used in the wax synthase assays, [1-$^{14}$C]palmitoyl-CoA, is purchased from Amersham (Arlington Heights, Ill.). Other chain length substrates were synthesized in order to perform chain length specification studies. Long chain [1-$^{14}$C]fatty acids (specific activity 51–56 Ci/mole), namely 11-cis-eicosenoic acid, 13-cis-docosenoic acid and 15-cis-tetracosenoic acid are prepared by the reaction of potassium [$^{14}$C]cyanide with the corresponding alcohol mesylate, followed by the base hydrolysis of the alcohol nitrile to the free fatty acid. The free fatty acids are converted to their methyl esters with ethereal diazomethane, and purified by preparative silver nitrate thin layer chromatography (TLC). The fatty acid methyl esters are hydrolyzed back to the free fatty acids. Radiochemical purity is assessed by three TLC methods: normal phase silica TLC, silver nitrate TLC, and C18 reversed phase TLC. Radiochemical purity as measured by these methods was 92–98%. Long chain [1-$^{14}$C]acyl-CoAs are prepared from the corresponding [1-$^{14}$C]free fatty acids by the method of Young and Lynen (*J. Bio. Chem.* (1969) 244:377), to a specific activity of 10 Ci/mole. [1-$^{14}$C]hexadecanal is prepared by the dichromate oxidation of [1-$^{14}$C]hexadecan-1-ol, according to a micro-scale modification of the method of Pletcher and Tate (*Tet. Lett.* (1978) 1601–1602). The product is purified by preparative silica TLC, and stored as a hexane solution at −70° C. until use.

B. Assay for Wax synthase Activity in a Microsomal Membrane Preparation

Wax synthase activity in a microsomal membrane preparation is measured by incubation of 40 μM [1-$^{14}$C]acyl-CoA (usually palmitoyl-CoA, sp. act. 5.1–5.6 mCi/mmol) and 200 mM oleyl alcohol with the sample to be assayed in a total volume of 0.25 ml. The incubation mixture also contains either 25 mM HEPES (4-[2-hydroxyethyll-1-piperazineethane-sulfonic acid), pH 7.5, as the buffering agent with 20% w/v glycerol, 1 mM DTT, 0.5M NaCl or 25 mM Tricine-NaOH, pH 7.8, as the buffering agent with 0.28M NaCl, 10% glycerol, and 2 mM β-mercaptoethanol. Initial studies were performed with the first buffer system, when the pH was chosen to accommodate the preference of the acyl-CoA reductase enzyme. Membrane preparations were later changed to the second buffer system to accommodate the higher pH optimum of wax synthase.

A substrate mixture is prepared in a glass vial, with oleyl alcohol being added immediately before use, and is added to samples. Incubation is carried out at 30° C. for up to one hour. The assay is terminated by placing the assay tube on ice and immediately adding 0.25 ml isopropanol:acetic acid (4:1 v/v). Unlabeled wax esters (0.1 mg) and oleyl alcohol (0.1 mg) are added as carriers. The [$^{14}$C]lipids are extracted by the scaled-down protocol of Hara and Radin (*Anal. Biochem.* (1978) 90:420). Two ml of hexane/isopropanol (3:2, v/v) is added to the terminated assay. The sample is vortexed, 1 ml of aqueous sodium sulphate solution (6.6% w/v) is added, and the sample is again vortexed.

C. Assay for Solubilized Wax synthase Activity

Solubilized wax synthase is assayed using up to 50 μl sample in a 250 μl assay that contains 40 μM 1-$^{14}$C-16:0 CoA (5 Ci/mol), 200 μM 18:1-OH, 0.07% soybean phospholipid (Sigma, P-3644), 0.2%CHAPS, 280 mM NaCl, 25 mM Tricine-NaOH, pH 7.8, 2 mM β-ME and 5.6% glycerol. Phospholipid (50 mg/ml in 0.5% CHAPS) is added directly to the sample, which is in 1% CHAPS, then diluted by a cocktail containing the remaining assay components. Reconstitution of activity is presumed to be based on the incorporation of wax synthase into the phospholipid vesicles. Wax synthase is sensitive to detergent and requires the amount of phospholipid (PL) and detergent (CHAPS) to be balanced at 2.8/1 (CHAPS/PL, w/w) in the assay for maximal activity. Assays for wax synthase activity in samples concentrated by ultra-filtration require a readjustment of the sample volume assayed because of the concentration of CHAPS. Introducing too much CHAPS into the assay results in inhibition of activity. If samples are concentrated by ultrafiltration, the optimum volume of sample to be assayed may be reestablished by performing a concentration curve of %CHAPS in the assay using a small amount of sample and assaying at a fixed concentration of phospholipid and sodium chloride. Wax synthase is less sensitive to changes in PL concentration than it is to changes in CHAPS concentration.

D. Analysis of Assay Products

For analyzing the products of either the microsomal membrane preparation wax synthase assay or the solubilized wax synthase assay, two protocols have been developed. One protocol, described below as "extensive assay" is more time-consuming, but yields more highly quantitative results. The other protocol, described below as "quick assay" also provides a measure of wax synthase activity, but is faster, more convenient and less quantitative.

1. Extensive Analysis: Following addition of the sodium sulphate and vortexing the sample, the upper organic phase is removed and the lower aqueous phase is washed with 4 ml hexane/isopropanol (7:2 v/v). The organic phases are pooled and evaporated to dryness under nitrogen. The lipid residue is resuspended in a small volume of hexane, and an aliquot is assayed for radioactivity by liquid scintillation counting. The remainder of the sample can be used for TLC analysis of the labeled classes and thereby give a measure of total wax produced.

For lipid class analysis the sample is applied to a silica TLC plate, and the plate is developed in hexane/diethyl ether/acetic acid (80:20:1 or 70:30:2 v/v/v). The distribution of radioactivity between the lipid classes, largely wax esters, free fatty acids, fatty alcohols, and polar lipids at the origin, is measured using an AMBIS radioanalytic imaging system (AMBIS Systems Inc., San Diego, Cailf.). If necessary the individual lipid classes can be recovered from the TLC plate for further analysis. Reversed-phase TLC systems using C18 plates developed in methanol have also been used for the analysis.

2. Quick Analysis: Following addition of the sodium sulfate and vortexing the sample, a known percentage of the organic phase is removed and counted via liquid scintillation counting. This calculation is used to estimate the total counts in the organic phase. Another portion of the organic phase is then removed, dryed down under nitrogen, redissolved in hexane and spotted on TLC plates and developed and scanned as described for the detailed assay. In this manner the percentage of the total counts which are incorporated into wax is determined.

Example 2

Further Studies to Characterize Wax Synthase Activity

A. Seed Development and Wax Synthase Activity Profiles

Embryo development was tracked over two summers on five plants in Davis, Calif. Embryo fresh and dry weights were found to increase at a fairly steady rate from about day 80 to about day 130. Lipid extractions reveal that when the embryo fresh weight reaches about 300 mg (about day 80), the ratio of lipid weight to dry weight reaches the maximum level of 50%.

Wax synthase activity was measured in developing embryos as described in Example 1B. As the jojoba seed coats were determined to be the source of an inhibiting factor(s), the seed coats were removed prior to freezing the embryos in liquid nitrogen for storage at −70° C.

Development profiles for wax synthase activities as measured in either a cell free homogenate or a membrane fraction, indicate a large induction in activity which peaks at approximately 110–115 days after anthesis. Embryos for enzymology studies were thus harvested between about 90 to 110 days postanthesis, a period when the wax synthase activity is high, lipid deposition has not reached maximum levels, and the seed coat is easily removed. The highest rate of increase of wax synthase activity is seen between days 80 and 90 postanthesis. Embryos for cDNA library construction were thus harvested between about 80 to 90 days postanthesis when presumably the rate of synthase of wax synthase protein would be maximal. Correspondingly, the level of mRNA encoding wax synthase would be presumed to be maximal at this stage.

B. Microsomal Membrane Preparation

Jojoba embryos are harvested at approximately 90–110 days after flowering, as estimated by measuring water content of the embryos (45–70%). The outer shells and seed coats are removed and the cotyledons quickly frozen in liquid nitrogen and stored at −70° C. for future use. For initial protein preparation, frozen embryos are powdered by pounding in a steel mortar and pestle at liquid nitrogen temperature. In a typical experiment, 70 g of embryos are processed.

The powder is added, at a ratio of 280 ml of solution per 70 g of embryos, to the following high salt solution: 3M NaCl, 0.3M sucrose, 100 mM HEPES, 2 mM DTT, and the protease inhibitors, 1 mM EDTA, 0.7 mg/ml leupeptin, 0.5 mg/ml pepstatin and 17 mg/ml PMSF. A cell free homogenate (CFH) is formed by dispersing the powdered embryos in the buffer with a tissue homogenizer (Kinematica, Switzerland; model PT10/35) for approximately 30 sec. and then filtering through three layers of Miracloth (CalBioChem, LaJolla, Calif.). The filtrate is centrifuged at 100,000×g for one hour.

The resulting sample consists of a pellet, supernatant and a floating fat pad. The fat pad is removed and the supernatant fraction is collected and dialyzed overnight (with three changes of the buffering solution) versus a solution containing 1M NaCl, 100 mM HEPES, 2 mM DTT and 0.5M EDTA. The dialyzate is centrifuged at 200,000×g for 1½ hour to yield a pellet, DP2. The pellet is suspended in 25 mM HEPES and 10% glycerol, at ½₀ of the original CFH volume, to yield the microsomal membrane preparation.

Activity is assayed as described in Example 1. Recovery of wax synthase activity is estimated at 34% of the original activity in the cell free homogenate. Wax synthase activity in this preparation is stable when stored at −70° C.

C. Substrate Specificity

Acyl-CoA and alcohol substrates having varying carbon chain lengths and degrees of unsaturation were added to microsomal membrane fractions prepared as described above to determine the range of substrates recognized by the jojoba wax synthase.

Acyl-CoA and alcohol substrates having varying carbon chain lengths and degrees of unsaturation were added to microsomal membrane fractions prepared as described in Example 3A to determine the range of substrates recognized by the jojoba wax synthase. Assays were performed as described in Example 1B using the Tricine buffer system with the following change, both acyl-CoA and alcohol concentrations were 40 $\mu$M instead of the 200 $\mu$M alcohol concentration normally used. Acyl-CoA's were prepared as 2.5 mM stocks (in 1.25 mM Na Acetate buffer pH 4.8 and 1.5% CHAPS) and 4 $\mu$l of these stocks were used in a 250 $\mu$l assay making the final CHAPS concentration 0.024%. Without the addition of detergent, the long-chain saturated acyl-CoA's would not dissolve in the buffer. Alcohols were prepared as 25 mM stocks in 2-methoxyethanol and 0.4 $\mu$l of the stock was used in a 250 $\mu$l assay. To evaluate the acyl-CoA specificity, 1-$^{14}$C-hexadecanol (10.3 mCi/mmol, Sigma 31,326-2) was used as substrate. The purchased 1-$^{14}$C-hexadecanol was only 62% pure and had to be further purified by thin layer chromatography prior to use. The product was spotted onto a glass silica gel TLC plate and migrated in hexane:diethyl ether:acetic acid (70:30:2). Unlabeled alcohol was spotted in outside lanes and used to identify the migration level of the radiolabeled product. The TLC plate was briefly exposed to iodine vapors to identify the location of the alcohol. The 1-$^{14}$C-hexadecanol spot was scraped from the TLC plate and transferred to a new vial. The product was eluted from the silica with hexane/isopropanol and the organic extract was filtered to remove silica. The filtered solvent was transferred to a new vial where the solvent was evaporated to dryness. The final product was resuspended in 2-methoxyethanol at a concentration of 0.15 $\mu$Ci/$\mu$l. The final product appeared to be 100% pure by TLC in the solvent system above. The 1-$^{14}$C-16:0-CoA was as described in Example 1. Results of these experiments are presented in Table 1 below.

TABLE 1

| Structure | Acyl Group | pmol/min/mg Alcohol Group |
|---|---|---|
| 8:0 | 147.5 | 2656.3 |
| 10:0 | 197.8 | 2396.8 |
| 12:0 | 345.5 | 5663.4 |
| 14:0 | 1584.6 | 4919.1 |
| 16:0 | 1533.8 | 5250.6 |
| 18:0 | 1693.8 | 2557.9 |
| 20:0 | 1373.2 | 1666.4 |
| 22:0 | 1196.6 | 1555.9 |
| 24:0 | 1308.3 | 2582.0 |
| 18:1 9-c | 821.9 | 12623.8 |
| 18:1 9-t | nd | 12600.2 |
| 18:1 11-c | nd | 12147.6 |
| 18:1 11-t | nd | 13739.4 |
| 18:2 9-c, 12-c | 198.8 | 11344.2 |
| 18:3 9-2, 12-c, 15-c | 516.1 | nd |
| 20:1 11-c | 3880.1 | 6172.4 |
| 22:1 13-c | 916.8 | 2783.0 |
| 22:1 13-t | nd | 1862.0 |
| 24:1 15-c | 1794.0 | 1576.3 |

For comparison purposes it is desirable to evaluate acyl-CoA's and alcohol's at equivalent concentrations, however, in practicality there is an endogenous pool of alcohol present in jojoba microsomal fractions of unknown concentration. This pool dilutes the $^{14}$C labeled hexadecanol used to evaluate the acyl-CoA's rendering some of the waxes formed undetectable. The result is an underestimation of the specific activity for all of the acyl-CoA's relative to the specific activities of the alcohols.

The above results demonstrate that the jojoba wax synthase utilizes a broad range of fatty acyl-CoA and fatty alcohol substrates.

In addition, wax synthase activity towards various acyl-thioester substrates was similarly tested using palmitoyl-CoA, palmitoyl-ACP and N-acetyl-S-palmitoyl cysteamine as acyl substrates. The greatest activity was observed with the acyl-CoA substrate. Significant activity (~10% of that with acyl-CoA) was observed with acyl-ACP, but no activity was detectable with the N-acetyl-S-palmitoyl cysteamine substrate.

D. Effectors of Activity

Various sulphydryl agents were screened for their effect on wax synthase activity. Organomercurial compounds were shown to strongly inhibit activity. Iodoacetamide and N-ethylmaleamide were much less effective. Inhibition by para-hydroxymercuribenzoate was observed, but this inhibition could be reversed by subsequent addition of DTT. These results demonstrate that inhibition by para-hydroxymercuribenzoate involves blocking of an essential sulphydryl group.

Example 3

Purification of Jojoba Wax Synthase

Methods are described which may be used for isolation of a jojoba membrane preparation having wax synthase activity, solubilization of wax synthase activity, and further purification of the wax synthase protein.

A. Microsomal Membrane Preparation

The following modification of the method described in Example 2 is employed and provides an improved membrane fraction useful for purification of wax synthase from solubilized membranes.

Typically, 100 g of jojoba embryos are added to 400 ml of extraction buffer (40 mM Tricine-NaOH, pH 7.8, 200 mM KCl, 10 mM EDTA, 5 mM β-mercaptoethanol), ground in a blender, and homogenized with a Polytron tissue disrupter. All subsequent steps are performed at 4° C. The blended material is filtered through Miracloth (CalBioChem). Centrifugation (20,000×g; 20 min.) of the filtrate yielded a floating wax layer, a turbid supernatant fraction and a dark green pellet. The supernatant fraction is collected and centrifuged (100,000×g; 2 h) to obtain membrane pellets which are then resuspended in 40 ml of Buffer A (25 mM Tricine-NaOH, pH 7.8, 200 mM KCl, 5 mM EDTA, 5 mM β-mercaptoethanol) containing 50% (w/v) sucrose. This homogenate is distributed into four SW28 centrifuge tubes (Beckman) and each is overlaid with 10 ml Buffer A containing 20% sucrose and then with 13 ml Buffer A. After centrifugation (28,000 rpm; 2 h), a membrane fraction is collected from the 20%/50% sucrose interface, diluted with four volumes Buffer A and collected by centrifugation (200,000×g; 1 h). The membranes are then homogenized in 10 ml storage buffer [25 mM Tricine-NaOH, pH 7.8, 1 M NaCl, 10% (w/v) glycerol, 5 mM β-mercaptoethanol)]. The protein concentration of membranes prepared via this protocol is typically between 7 and 9 mg/ml. Protein concentrations are estimated as described (Bradford, 1976) using BSA as the protein standard.

B. Solubilization of Wax synthase Protein

The membrane suspension is adjusted to approximately 0.83 mg of protein per ml by dilution with storage buffer (25 mM Tricine-NaOH, pH 7.8, 1M NaCl, 10% glycerol, 5 mM β-mercaptoethanol). Solid 3-([3-cholamidopropyl] dimethyl-ammonio)-1-propanesulfate (CHAPS) is added to achieve a final concentration of 2% (w/v) and a detergent to protein ratio of 24:1. After incubation on ice for 1 hr, the sample is centrifuged (200,000 g for 1 hr), and the supernatant fraction collected.

C. Purification of Wax Synthase Activity

The 200,000g supernatant fraction is diluted (with 0.57% CHAPS, 25 mM Tricine-NaOH, pH 7.8, 20% glycerol) to yield final concentrations of NaCl and CHAPS of 0.3M and 1%, respectively. The sample is loaded onto a Blue A-agarose (Amicon, Inc., Beverly, Mass.) column that has been equilibrated with buffer B (25 mM Tricine-NaOH, pH 7.8, 1% CHAPS, 20% glycerol,) containing 0.3M NaCl. After washing with equilibration buffer, wax synthase activity is eluted with buffer B containing 2M NaCl. Active fractions eluted from the Blue A column are pooled (Blue Pool) and used for further chromatography.

Two purification protocols were used for band identification and further purification of the wax synthase protein. In Protocol 1 (FIG. 1), the Blue Pool was concentrated 5.4 fold by ultrafiltration in a pressure cell fitted with a YM 30 membrane (Amicon, Inc., Beverly, Mass.). One-half of the concentrate was applied to a Ceramic Hydroxyapatite (CHT) column (Bio-Scale CHT-2; Bio-Rad, Hercules, Calif.) Equilibrated in buffer B containing 2M NaCl. The column was washed with 6 column volumes of equilibration buffer and bound proteins were eluted with buffer B containing 0.1M dipotassium phosphate and 2M NaCl. After reequilibration of the CHT column, the second half of the Blue Pool concentrate was chromatographed in the same manner. In order to detect activity, wax synthase was assayed according to the protocol for samples concentrated by ultrafiltration. Wax synthase activity, measured on CHT-Run 1, was found in the flow through and wash. Protein profiles of the two CHT runs were identical so the CHT-run 2 was not assayed. Active fractions from the two CHT runs were pooled and concentrated 10 fold and applied to a Sephacryl S100 HR column (2.5×90 cm) equilibrated in buffer B with 1.0 M NaCl. Protein and activity determinations were made and active fractions were selected from the retained portion of the run which maximized activity and minimized protein. The S100 pool (fractions 64–70) was applied to a crystalline hydroxylapatite (HA) column (Bio-Gel HT; Bio-Rad, Hercules, Calif., 1×19.3 cm) equilibrated in buffer B with 1 M NaCl. Again, the majority of the wax synthase activity was present in the flow through and wash. Bound proteins were eluted in buffer B with 0.1M dipotassium phosphate, and 1M NaCl. Fractions from the final HA run were examined by SDS-PAGE. A single protein migrating at 33 kD on SDS-PAGE was correlated with the presence of wax synthase activity.

Figure 2A:
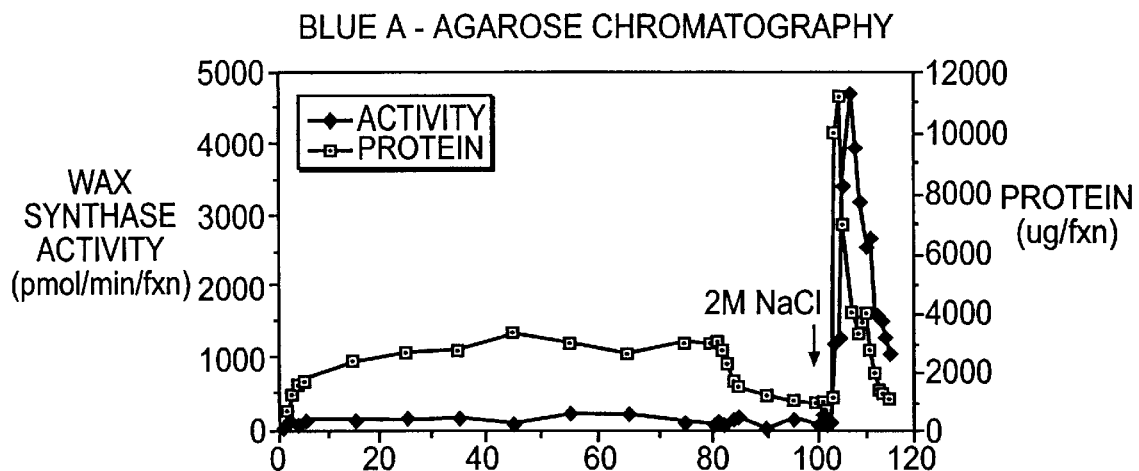
FIG. 2A provides results of Blue A agarose chromatography.
Figure 2B:
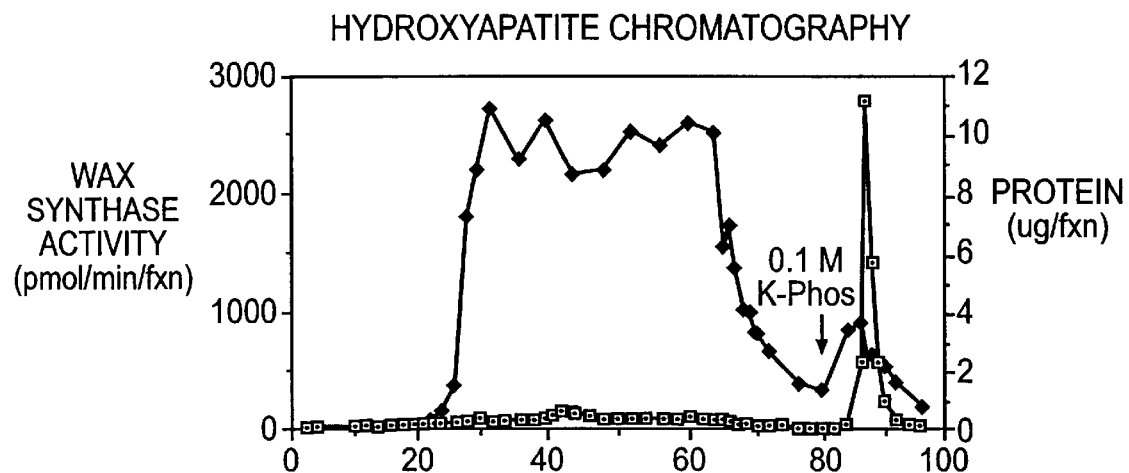
FIG. 2B provides results of hydroxyapatite chromatography.
Figure 2C:
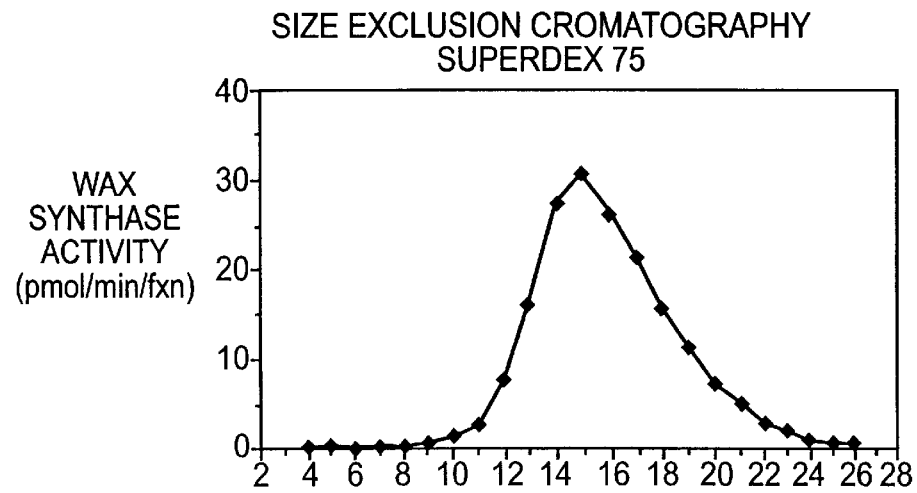
FIG. 2C provides results of Superdex 75 size exclusion chromatography.

In a second preparation (Protocol 2, FIG. 2) the Blue Pool was applied directly to a crystalline HA column (1×11.7 cm), equilibrated in buffer B with 1M NaCl, without concentration. Two fractions were selected for further purification by size exclusion chromatography on a Superdex 75 HR 10/30 column (Bio-Rad, Hercules, Calif.; sizing range:5000–75,000 daltons) equilibrated with 25 mM Tricine-NaOH, pH 7.8, 1% CHAPS, 20% glycerol, 1M NaCl. Wax synthase activity was measured according to the protocol described for solubilized samples in Example 1C. One fraction eluted early in the flow through of the HA column (fraction 31) and the other eluted in the wash (fraction 67). The protein profiles of the two fractions were different based on SDS-PAGE analysis. Both Superdex 75 runs were examined by gradient SDS-PAGE and a protein of approximately 33 kD was identified that chromatographed with activity. A calibration curve was generated using molecular mass standards chromatographed under the same buffer and column conditions. Comparison of the elution volume of the peak of Wax Synthase activity to this standard curve yielded a value of 48 kDa for the molecular mass of the solubilized enzyme.

A chart representing the purification of wax synthase from Protocol 1 (Table 2) shows a 150 fold purification of the enzyme from the solubilized protein fraction.

TABLE 2

Purification of Jojoba Wax Synthase

| Purification Step | Enzyme Activity (nmol/min) | Yield % | Protein (mg) | Specific Activity (nmol/min/mg) | Purification (fold) |
| --- | --- | --- | --- | --- | --- |
| Solubilized Fraction | 274.4 | 100 | 415 | 0.7 | 1 |
| Blue A Agarose | 214.7 | 78.2 | 15 | 14.3 | 22 |
| Ceramic Hydroxyapatite | 176.6 | 64.3 | 6.4 | 27.6 | 42 |
| Sephacryl S-100 (sizing) | 41.3 | 15.1 | 1.2 | 33.1 | 50 |
| Hydroxyapatite (crystalline) | 18.8 | 6.9 | 0.2 | 99.2 | 150 |

D. SDS PAGE Analysis

Samples from the column fractions were diluted in SDS PAGE sample buffer (1× buffer=2% SDS, 250 mM β-mercaptoethanol, 0.0025% bromphenol blue) and analyzed by electrophoresis. Polyacrylamide gradient gel electrophoresis (10–13%) was carried out according to the method of Laemmli (*Nature* (1970) 227:680–685) with some of the modifications of Delepelaire (*Proc. Nat. Acad. Sci.* (1979) 76:111–115). Sodium dodecyl sulfate was used in the upper reservoir buffer at 0.1% but was ommitted from the lower reservoir buffer, stacking and resolving gels. The stacking gel contained 5% of a 30% acrylamide stock (29.2% acrylamide, 0.8% N,N'-bis-methyleneacrylamide, w/v), 0.06% ammonium persulfate (w/v) and 0.1% TEMED (v/v). The resolving gel contained a 10–13% linear gradient of acrylamide stock stabilized by a 0–10% linear gradient of sucrose. Electrophoresis was carried out at room temperature at 150V, constant voltage, for 9–10 hours. Proteins were visualized by staining with silver according to the method of Blum et al. (*Electrophoresis* (1987) 8:93–99 or with Coomassie Blue (0.1% Coomassie Blue R-250, 50% methanol, 10% acetic acid). The 33 kDa protein identified as wax synthase does not appear as a major component of the active fraction until purification through the hydroxyapatite column. Following purification Protocol 1 (Example 3C) the only protein that correlates with activity on the final column is one at 33 kDa.

Example 4

Preparation of Protein for In-Gel Digestion

A. Preparation of Samples for SDS-PAGE by Concentration

Odd numbered fractions from the flow through/wash of the final HA column (Protocol 1) were pooled and concentrated three fold by ultrafiltration in a pressure cell fitted with a YM 30 membrane (Amicon, Inc., Beverly, Mass.). The sample was further concentrated using two Centricon-30 units (Amicon, Inc., Beverly, Mass.) to volumes of approximately 50 μl. Each sample was treated with 6 μl SDS Cocktail (4 μl 20%SDS, 1 μl 14.3M β-metcaptoethanol, and 1 μl 0.1% Bromophenol Blue). After sitting at room temperature for 15 minutes, the samples were applied to a 10–13% acrylamide gradient gel (Example 3D) (16×16 cm×1 mm thick) and proteins were resolved by electrophoresis at 150V, constant voltage, for 9.5 hours. The gel was stained with 0.1% Coomassie Blue in 50% methanol, 10% acetic acid for 15 minutes then destained in 50% methanol, 10% acetic acid for 2×20 minutes. The 33 kD Wax Synthase band was excised from the gel and destained in 50% ethanol for 3×20 minutes. One lane contained a streak of protein and was not used in the final digestion.

B. Preparation of Samples for SDS-PAGE by Precipitation

Aliquots (0.8 ml) of the even numbered fractions from the final HA column (Protocol 1) were pooled in groups of three over the column profile. The pools were divided equally into three, 1.5 ml vials. Protein was precipitated by the addition of 0.2 ml 40% TCA. After 30 minutes on ice the samples were centrifuged (12,000×g, 15 minutes at 4 C) to pellet the precipitated protein. The supernatants were removed and the pellets washed twice with 0.6 ml ice cold acetone. The final three pellets for each pooled set of samples were resuspended with the same 50 μl of SDS sample buffer by transfering the buffer from one vial to the next. The emptied vials, that had already been resuspended, were washed with 10 μl of sample buffer for a total resuspended volume of 60 μl for each pooled sample. The samples were applied to a 12% acrylamide Tris/Glycine mini-gel (Novex, San Diego, Calif., 1.5 mm×10 well) and proteins were resolved by electrophoresis at 150 V, constant voltage, for 20 minutes beyond the elution of dye from the foot of the gel. The gel was stained with Coomassie Blue and destained using Gel-Clear (Novex, San Diego, Calif.). Wax Synthase was excised from three non-equivalent lanes on the gel representing the peak and tailing fractions from the column. The gel slices were placed in 1.5 ml vials and destained with 1 ml of 50% methanol, 10% acetic acid for 2 hours. The destain solution was removed and the gel slices were frozen in liquid nitrogen and sent on dry ice, overnight, to the W M Keck Foundation Biotechnology Resource Laboratory at Yale University for in-gel-digestion. One gel slice from the sample concentrated by ultrafiltration and three gel slices from the samples concentrated by precipitation were pooled for in-gel tryptic digestion.

Example 5

Determination of Amino Acid Sequence

Protein sequencing was performed at the W. M. Keck Foundation Biotechnology Resource Laboratory, Yale University. Procedures include amino acid analysis of a portion (10–15%) of the gel slice for quantitation and amino acid composition, digestion of the protein with one of the proteolytic enzymes (trypsin or lysyl endopeptidase), and fractionation of the products by reverse phase HPLC. Absorbance peaks are selected from the HPLC run and subjected to laser desorption mass spectrometry to determine the presence, amount, and mass of the peptide prior to protein sequencing. The longest peptides are selected for microsequencing.

Amino acid seqeunces of jojoba wax synthase peptides obtained by trypsin digestion are presented in Table 3 below using the one letter code.

TABLE 3

| Amino Acid Sequence of Jojoba Wax Synthase Tryptic Peptides | | |
| --- | --- | --- |
| WSpep29 | FVPAVAPHGGALR | (SEQ ID NO: 1) |
| WSpep33 | TIDEYPVMFNYTQK | (SEQ ID NO: 2) |

Example 6

Purification of Additional Wax Synthases and Reductames

A. Adaptation of Jojoba Wax Synthase Solubilization and Purification Methods to Obtain Partially Purified Preparations of Wax Synthase From Other Organisms are Described.

Acinetobacter

Cells of *Acinetobacter calcoaceticus* strain BD413 (ATCC #33305) are grown on ECLB (*E. coli* luria broth), collected during the logarithmic growth phase and washed in a buffer containing either HEPES-NaOH, pH 7.5, or Tricine-NaOH pH 7.8, in 0.1M NaCl, 1 mM DTT and protease inhibitors. Washed cells were resuspended in fresh buffer and ruptured by passage through a French pressure cell (two passes at ~16,000 p.s.i.). Unbroken cells are removed by centrifugation at 5000×g for 10 minutes, and membranes are collected by centrifugation at 100,000×g for 1 hour. The membrane pellet is homogenized in storage buffer (25 mM HEPES-NaOH, pH 7.5, or 25 mM Tricine-NaOH, pH 7.8, in 10% (w/v) glycerol, 100 mM NaCl). Wax synthase activity is detected in these membranes using assay conditions described for the jojoba enzyme in Example 1B, using (1-$^{14}$C)palmitoyl-CoA and 18:1 alcohol as the substrates.

Wax synthase activity is solubilized by incubation of the membranes with 2% CHAPS in the presence of 0.5M NaCl, at a detergent to protein ratio of 5:1. Solubilization of the activity is demonstrated by the detection of wax synthase enzyme activity in the supernatant fraction after centrifugation at 200,000 g for 1 hour and by size exclusion chromatography (i.e. the activity elutes from the column in the retained fractions as a symmetrical peak). The activity of the solubilized enzyme is detected by simple dilution of the CHAPS concentration to ~0.3% (i.e. to below its CMC). Incorporation of the enzyme into phospholipid vesicles is not required to detect solubilized activity.

For purification, the solubilized Acinetobacter wax synthase activity is subjected to chromatographic procedures similar to those described for the jojoba wax synthase. In one protocol, the soluble protein preparation is loaded to a Blue A agarose column under low salt conditions (100 mM NaCl in a column buffer containing 0.75% % CHAPS, 10% glycerol, 25 mM HEPES-NaOH, pH 7.5) and eluted from the column using 1.0M NaCl in the column buffer.

Size exclusion chromatography on Superose 12 (Pharmacia; Piscataway, N.J.) medium is used to obtain an estimate of the size of the native enzyme. Comparison to molecular mass standards chromatographed under identical conditions yields an apparent mass of ~40 kDa for the solubilized wax synthase.

In another protocol, solubilized protein is loaded onto a Blue A column equilibrated with 25 mM Tricine-NaOH, pH 7.8, 1% CHAPS, 20% glycerol containing 0.1M NaCl and eluted in the same buffer containing 1.0 M NaCl. The eluted material is then loaded onto a hydroxyapatite column equilibrated with column buffer containing 1.0 M NaCl and unlike the jojoba wax synthase, the acinetobacter wax synthase activity binds the column and is eluted in a gradient of 1–100 mM dipotassium phosphate. When examined by SDS-PAGE, several protein candidates can be correlated with wax synthase activity.

Euglena *Euglena gracilis*, strain Z (ATCC No. 12716) is grown heterotrophically in the dark (Tani et al. (1987) *Agric. Biol. Chem.* 51:225–230) at ~26° C. with moderate shaking. Cells are collected and washed in buffer containing 25 mM Bis-Tris-Propane, pH 7.0, 0.25M NaCl and 1 mM EDTA. Washed cells are resuspended in fresh buffer and ruptured by passage through a French pressure cell (two passes at ~16,000 p.s.i.). Unbroken cells, cell debris and nuclei are removed by centrifugation at 20,000×g for 20 minutes, and microsomal membranes are collected by centrifugation at 200,000×g for 1 hour. The membrane pellet is homogenized in storage buffer (25 mM Bis-Tris-Propane, pH 7.0, 0.25M NaCl, 10% (w/v) glycerol and 1 mm EDTA). Wax synthase activity is detected in these membranes using assay conditions as described for the jojoba enzyme. The radiolabelled substrate is the same as for the jojoba example (i.e. [1-$^{14}$C] palmitoyl-CoA), however, 16:0 rather than 18:1 is used as the alcohol acceptor, and Bis-Tris-Propane buffer at pH 7.0 is utilized.

The Euglena wax synthase activity is solubilized by incubation of the membranes with 2% CHAPS in the presence of 0.5M NaCl. Solubilization of the protein is demonstrated by the detection of enzyme activity in the supernatant fraction after centrifugation at 200,000×g for 1 hour. The activity of the solubilized enzyme is detected by dilution of the CHAPS concentration to ~0.3% (i.e. to below its CMC). It is not necessary to incorporate the enzyme into phospholipid vesicles as was the case for the solubilized jojoba wax synthase.

For partial purification, the solubilized Euglena wax synthase activity is subjected to chromatographic separation on Blue A agarose medium. The column is equilibrated with 0.1M NaCl in a column buffer containing; 25 mM Bis-Tris- Propane, pH 7.0, 20% (w/v) glycerol, 0.75% CHAPS and 1 mM EDTA. The sample containing solubilized wax synthase activity is diluted to 0.1M NaCl and loaded onto a 1×7 cm column (5.5 ml bed volume). The column is washed with equilibration buffer and subjected to a linear NaCl gradient (0.1M to 1.0M NaCl) in column buffer. Wax synthase activity is eluted as a broad peak in the last half of the salt gradient.

SDS-PAGE analysis of column fractions reveals that the polypeptide complexity of the activity eluted from the column is greatly reduced relative to the loaded material. A polypeptide with an apparent molecular mass of ~41 kD was observed to track with wax synthase activity in the column fractions. Further purification techniques, such as described for jojoba and Acinetobacter are conducted to verify the association of wax synthase activity with the ~41 kD peptide.

For further analysis of wax synthase activity in Euglena, size exclusion chromatography was conducted as follows. A microsomal membrane preparation was obtained from Euglena cells grown on liquid, heterotrophic, medium (Tani et al., supra) in the dark. Wax synthase activity was solubilized by treating the membranes with 2% (w/v) CHAPS and 500 mM NaCl in a buffered solution (25 mM Bis-Tris, pH 7.0, 1 mM EDTA and 10% (w/v) glycerol) for 1 hour on ice. After dilution of the CHAPS to 0.75% and the NaCl to 200 mM by addition of a dilution buffer, the sample was centrifuged at ~200,000×g for 1.5 hours. The supernatant fraction was loaded onto a Blue A dye column preequilibrated with Column Buffer (25 mM Bis-Tris pH 7.0, 1 mM EDTA, 10% glycerol, 0.75% CHAPS) which also contained 200 mM NaCl. The column was washed with Column Buffer containing 200 mM NaCl until the A280 of the effluent returned to the preload value. Wax synthase activity which had bound to the column was released by increasing the NaCl concentration in the Column Buffer to 1.5M. The fractions from the Blue A column containing wax synthase activity released by the 1.5M NaCl (~20 ml combined volume) were pooled and concentrated approximately 30-fold via ultrafiltration (Amicon pressure cell fitted with a YM 30 membrane). The concentrated material from the Blue A column was used as the sample for a separation via size exclusion chromatography on Superose 12 medium (Pharmacia).

Approximately 200 µ of the sample was loaded onto a Superose 12 column (HR 10/30), pre-equilibrated with Column Buffer containing 0.5M NaCl, and developed at a flow rate of 0.1 ml/min. The wax synthase activity eluted from the column as a smooth peak. Comparison of the elution volume of the wax synthase activity with the elution profiles of molecular mass standard proteins yielded an estimate of 166 kD for the apparent molecular mass of the enzyme. Fractions which contained wax synthase activity were analyzed via SDS-polyacrylamide gel electrophoresis followed by silver staining. A preliminary analysis of the polypeptide profiles of the various fractions did not reveal any proteins with molecular masses of 100 kD or greater whose staining intensity appeared to match the activity profile. The wax synthase polypeptide may be present as a minor component in the sample mixture that is not readily detectable on the silver-stained gel. Alternatively, the enzyme may be composed of subunits which are dissociated during SDS-PAGE.

Example 7

Isolation of Wax Synthase Nucleic Acid Sequences

DNA sequences encoding wax synthase peptides are obtained from jojoba using synthetic oligonucleotides designed from wax synthase peptide sequences. The wax synthase nucleic acid sequences may be obtained by amplification of DNA by polymerase chain reaction (PCR) using oligonucleotides as primers, or alternatively, by screening a cDNA or genomic DNA library by radiolabeling the oligonucleotides or previously isolated sequences for use as probes.

A. Construction of Jojoba cDNA Libraries

RNA may be isolated using the methods described by Cathala, et al. (1983) *DNA*, 3:329–335. RNA is isolated from jojoba embryos collected at 80–90 days post-anthesis using a polyribosome isolation method, initially described by Jackson and Larkins (*Plant Physiol.* (1976) 57:5–10), as modified by Goldberg et al. (*Developmental Biol.* (1981) 83:201–217). In this procedure all steps, unless specifically stated, are carried out at 4° C. 10 gm of tissue are ground in liquid nitrogen in a Waring blender until the tissue becomes a fine powder. After the liquid nitrogen has evaporated, 170 ml of extraction buffer (200 mM Tris pH 9.0, 160 mM KCl, 25 mM EGTA, 70 mM MgC12, 1% Triton X-100, 05% sodium deoxycholate, 1 mM spermidine, 10 mM β-mercaptoethanol, and 500 mM sucrose) is added and the tissue is homogenized for about 2 minutes. The homogenate is filtered through sterile miracloth and centrifuged at 12,000×g for 20 minutes. The supernatant is decanted into a 500 ml sterile flask, and 1/19 volume of a 20% detergent solution (20% Brij 35, 20% Tween 40, 20% Noidet p-40 w/v) is added at room temperature. The solution is stirred at 4° C. for 30 minutes at a moderate speed and the supernatant is then centrifuged at 12,000×g for 30 minutes.

About 30 ml of supernatant is aliquoted into sterile Ti 60 centrifuge tubes and underlaid with 7 ml of a solution containing 40 mM Tris pH 9.0, 5 mM EGTA, 200 mM KCl, 30 mM MgC12, 1.8M sucrose, 5 mM β-mercaptoethanol. The tubes are filled to the top with extraction buffer, and spun at 60,000 rpm for 4 hours at 4° C. in a Ti60 rotor. Following centrifugation, the supernatant is aspirated off and 0.5 ml of resuspension buffer (40 mM Tris pH 9.0, 5 mM EGTA, 200 mM KCl, 30 mM $MgCl_2$, 5 mM β-mercaptoethanol) is added to each tube. The tubes are placed on ice for 10 minutes, after which the pellets are thoroughly resuspended and pooled. The supernatant is then centrifuged at 120×g for 10 minutes to remove insoluble material. One volume of self-digested 1 mg/ml proteinase K in 20 mM Tris pH 7.6, 200 mM EDTA, 2% N-laurylsarcosinate is added to the supernatant and the mixture incubated at room temperature for 30 minutes.

RNA is precipitated by adding 1/10 volume of sodium acetate and 2 volumes of ethanol. After several hours at 20° C. RNA is pelleted by centrifugation at 12,000×g at 4° C. for 30 minutes. The pellet is resuspended in 10 ml of TE buffer (10 mM Tris, 1 mM EDTA) and extracted with an equal volume of Tris pH 7.5 saturated phenol. The phases are separated by centrifuging at 10,000×g for 20 minutes at 4° C. The aqueous phase is removed and the organic phase is re-extracted with one volume of TE buffer. The aqueous phases are then pooled and extracted with one volume of chloroform. The phases are again separated by centrifugation and the aqueous phase ethanol precipitated as previously described, to yield the polyribosomal RNA.

Polysaccharide contaminants in the polyribosomal RNA preparation are removed by running the RNA over a cellulose column (Sigma-cell 50) in high salt buffer (0.5M NaCl, 20 mM Tris pH 7.5, 1 mM EDTA, 0.1% SDS). The contaminant binds to the column and the RNA is collected in the eluant. The eluant fractions are pooled and the RNA is ethanol precipitated. The precipitated total RNA is then resuspended in a smaller volume and applied to an oligo d(T) cellulose column to isolate the polyadenylated RNA.

Polyadenylated RNA is used to construct a cDNA library in the plasmid cloning vector pCGN1703, derived from the commercial cloning vector Bluescribe M13- (Stratagene Cloning Systems; San Diego, Calif.), and made as follows. The polylinker of Bluescribe M13- is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with a synthetic linker having restriction sites for BamHI, PstI, XbaI, ApaI and SmaI, a 5' overhang of AATT, and a 3' overhang of TCGA. The insertion of the linker into pCGN1700 eliminates the EcoRI site, recreates the SstI (also, sometimes referred to as "SacI" herein) site found in Bluescribe, and adds the new restriction sites contained on the linker. The resulting plasmid pCGN1702, is digested with HindIII and blunt-ended with Klenow enzyme; the linear DNA is partially digested with PvuII and ligated with T4 DNA wax synthase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang stick-ends using terminal deoxynucleotidyl transferase. The tailed plasmid is separated from undigested or un-tailed plasmid by oligo(dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI stick-end at one end and a G-tail at the other. This complex is cyclized using an annealed synthetic cyclizing linker which has a 5' BamHI sticky-end, recognition sequences for restriction enzymes NotI, EcoRI and SstI, and a 3° C-tail end. Following ligation and repair the circular complexes are transformed into *E. coli* strain DH5a (BRL, Gaithersburg, Md.) to generate the cDNA library. The jojoba embryo cDNA bank contains between approximately 1.5× $10^6$ clones with an average cDNA insert size of approximately 500 base pairs.

Additionally, jojoba polyadenylated RNA is also used to construct a cDNA library in the cloning vector lZAPII/ EcoRI (Stratagene, San Diego, Calif.). The library is constructed using protocols, DNA and bacterial strains as supplied by the manufacturer. Clones are packaged using Gigapack Gold packaging extracts (Stratagene), also according to manufacturer's recommendations. The cDNA library constructed in this manner contains approximately 1×$10^6$ clones with an average cDNA insert size of approximately 400 base pairs.

B. Synthetic Oligonucleotides

In general, for use as PCR primers from single stranded DNA template reverse-transcribed from mRNA, oligonucleotides containing the sense orientation sequence corresponding to wax synthase peptide encoding sequences are prepared. These oligonucleotides are used as primers for the "forward" amplification reaction to produce sense strand DNA.

For the "reverse" reaction for amplification of the non-coding DNA strand, an oligonucleotide may be designed to be identical to a portion of a primer used to prepare DNA template for PCR. Alternatively, oligonucleotides which contain sequence complementary to wax synthase peptide encoding sequences may be used in combination with a "forward" wax synthase oligonucleotide primer as described above.

Where the wax synthase peptide sequences contain amino acids which may be encoded by a number of different codons, the forward or reverse primers may be "degenerate" oligonucleotides, i.e. containing a mixture of all or some of the possible encoding sequences for a particular peptide region. To reduce the number of different oligonucleotides present in such a mixture, it is preferable to select peptide regions which have the least number of possible encoding sequences when preparing the synthetic oligonucleotide for PCR primers. Similarly, where the synthetic oligonucleotide is to be used to directly screen a library for wax synthase sequences, lower degeneracy oligonucleotides are preferred.

Following is an example of the sequence of peptide WSPEP33 (center line) and the forward (top line) and reverse (bottom line) DNA sequences that encode the peptide WSPEP33 (SEQ ID NO: 3).

5' TTY GTN CCN GCN GTN GCN CCN CAY GGN GGN GCN YTN MGN 3'
F V P A V A P H G G A L R
3' AAR CAN GGN CGN CAN CGN GGN GTR CCN CCN CGN RAN KCN 5'

Following is an example of the sequence of peptide WSPEP29 (center line) and the forward (top line) and reverse (bottom line) DNA sequences that encode the peptide WSPEP29 (SEQ ID NO: 4).

5' ACN ATH GAY GAR TAY CCN GTN ATG TTY AAY TAY ACN CAR AAR 3'
T I D E Y P V M F N Y T Q K
3' TGN TAD CTR CTY ATR GGN CAN TAC AAR TTR ATR TGN GTY TTY 5'

Following is an example of the sequence of peptide WSPEP14 (center line) and the forward (top line) and reverse (bottom line) DNA sequences that encode the peptide WSPEP14 (SEQ ID NO: 5).

5' TTY MGN GAY GAY CCN WSN AAY GAY CAY 3'
F R D D P S N D H
3' AAR KCN CTR CTR GGN WSN TTR CTR GTR 5'

Following are sequences of synthetic oligonucleotides which may be used to obtain wax synthase sequences. The oligonucleotide names reflect the particular wax synthase peptide fragment numbers as listed in Example 5. The letter "F" in the oligonucleotide name designates a PCR forward reaction primer. The letter "R" designates a PCR reverse reaction primer.

```
                                         (SEQ ID NO: 6)
WSPEP29-F1    5' TTYGTNCCNGCNGTNGC 3'

(SEQ ID NO: 7)
WSPEP29-F2    5' GCNCCNCAYGGNGGNGC 3'

(SEQ ID NO: 8)
WSPFP29-R1    5' GCNCCNCCRTGNGGNGC 3'

(SEQ ID NO: 9)
WSPEP29-R2    5' GCNACNGCNGGNACRAA 3'

(SEQ ID NO: 10)
WSPEP33-F1    5' ACNATHGAYGARTAYCCNGT 3'
```

```
                                                  (SEQ ID NO: 11)
WSPEP33-F2      5' CCNGTNATGTTYAAYTAYAC 3'

(SEQ ID NO: 12)
WSPEP33-R1      5' TTYTGNGTRTARTTRAACAT 3'

(SEQ ID NO: 13)
WSPEP33-R2      5' AACATNACNGGRTAYTCRTC 3'

(SEQ ID NO: 14)
WSPEP14-F1      5' GAYGAYCCNWSNAAYGAYCA 3'

(SEQ ID NO: 15)
WSPEP14-R1      5' TGRTCRTTNSWNGGRTCRTC 3'
```

The nucleotide base codes for the above oligonucleotides are as follows:

| | | |
|---|---|---|
| A = adenine | T = thymine | Y = cytosine or thymine |
| C = cytosine | U = uracil | R = adenine or guanine |
| G = guanine | I = inosine | O = inosine or cytosine |
| H = adenine, cytosine or thymine | | |
| N = adenine, cytosine, guanine or thymine | | |
| W = adenine or thymine | | |
| S = guanine or cytosine | | |
| B = guanine, cytosine or thymine | | |
| K = guanine or thymine | | |
| M = adenine or cytosine | | |

C. PCR Reactions

Poly(A)+RNA is isolated from total RNA prepared from jojoba tissue as described above. cDNA is prepared from poly(A)+ or total RNA by reverse transcription using the Marathon cDNA Amplification Kit (Clontech Laboraties Inc according to the manufacturer's directions. The jojoba cDNA is used in PCR reactions 1–16 set forth below.

PCR is conducted in a Perkin Elmer Cetus GeneAmp PCR System 9600 PCR machine using reverse transcribed single-stranded cDNA as template. Commercially available PCR reaction and optimization reagents are used according to manufacturer's specifications

| Reaction | Forward Primer | Reverse Primer |
|---|---|---|
| 1 | WSPEP14-F1 | WSPEP29-R1 |
| 2 | WSPEP14-F1 | WSPEP29-R2 |
| 3 | WSPEP14-F1 | WSPEP33-R1 |
| 4 | WSPEP14-F1 | WSPEP33-R2 |
| 5 | WSPEP29-F1 | WSPEP14-R1 |
| 6 | WSPEP29-F1 | WSPEP33-R1 |
| 7 | WSPEP29-F1 | WSPEP33-R2 |
| 8 | WSPEP29-F2 | WSPEP14-R1 |
| 9 | WSPEP29-F2 | WSPEP33-R1 |
| 10 | WSPEP29-F2 | WSPEP33-R2 |
| 11 | WSPEP33-F1 | WSPEP14-R1 |
| 12 | WSPEP33-F1 | WSPEP29-R1 |
| 13 | WSPEP33-F1 | WSPEP29-R2 |
| 14 | WSPEP33-F2 | WSPEP14-R1 |
| 15 | WSPEP33-F2 | WSPEP29-R1 |
| 16 | WSPEP33-F2 | WSPEP29-R2 |

The temperature program used for PCR amplification is as follows: 1 cycle of 95 degrees C. for 2 minutes; 4 cycles of 95 degrees C. for 30 seconds, 60 degrees C. for 1 minute, and 72 degrees C. for 4 minutes; 4 cycles of 95 degrees C. for 30 seconds, 57 degrees C. for 1 minute, and 72 degrees C. for 4 minutes; 4 cycles of 95 degrees C. for 30 seconds, 54 degrees C. for 1 minute, and 72 degrees C. for 4 minutes; 4 cycles of 95 degrees C. for 30 seconds, 51 degrees C. for 1 minute, and 72 degrees C. for 4 minutes; and 25 cycles of 95 degrees C. for 30 seconds, 48 degrees C. for 1 minute, and 72 degrees C. for 4 minutes.

From reactions 3 and 4, a PCR product approximately 700 nucleotides in length was detected. The PCR product was purified using gel electrophoresis and cloned into pCR2.1 using a Topo TA cloning kit (Invitrogen Corp.). The DNA sequence of the cloned PCR product was determined and was 708 nucleotides long (FIG. 3).

The entire cDNA can be amplified using 5' and 3' RACE (Frohman et al., 1988) using the Marathon cDNA Amplification Kit (Clontech Laboratories Inc.) according to the manufacturers instructions. From the sequence of the 708 nucleotide PCR fragment (SEQ ID NO: 39) derived using primers WSPEP14-F1 and WSPEP33-R2 the following primers were synthesized:

```
                              (SEQ ID NO: 16)
WSRACEF1    GATTTGCCTCATTTTGTGATCTCGGTGCT (SEQ ID NO: 17)
WSRACEF2    GACCTATACCCCCAGTTCAACGAGCCATAC (SEQ ID NO: 18)
WSRACEF3    TTCAACGAGCCATACTTAGCCACCTCGCTG (SEQ ID NO: 19)
WSRACER1    AACAACCACCCTCCAGTCACCATCACGAAC (SEQ ID NO: 20)
WSRACER2    TTGCCTGAAACCGCCTTCTTCACCACCATC (SEQ ID NO: 21)
WSRACER3    AAGATGTCTGACACCATGAGGTTCCACCTG
```

3' RACE reactions were set up using parimers WSRACEF1, WSRACEF2, and WSRACEF3. 5'RACE reactions were set up using parimers WSRACER1,WSRACER2, and WSRACER3. PCR reactions were performed according to the manufacturer's protocol (Clontech Laboraties Inc.). All 6 PCR reactions gave visible PCR products ranging in size from approximately 700 nucleotides to 1000 nucleotides. The PCR products were gel purified and cloned into pCR2.1 according to the manufacturer's protocol (Invitrogen Corp.). The DNA sequence of several clones from both the 5' and 3' RACE reactions and the previous PCR product derived from primers WSPEP14-F1 and WSPEP33-R2 were assembled using sequencher software (Gene Codes Corp.). The assembled sequence of all the PCR products contains the coding region of the cDNA sequence.

To isolate a gene fragment suitable for cloning the wax synthase gene into expression cassettes for plant lipid modification, the coding region of the gene can be amplified from cDNA using the primers WAXSYNFOR (SEQ ID NO: 22) and WASXYNREV (SEQ ID NO: 23). The sequence of WAXSYNFOR is GGATCCGTCGACACAATGGAGGT-GGAGAAGGAGCTAAAG, and the sequence of WASX-YNREV is GCATGCAGATCTCACCACCCCAACAAAC-CCATC. The PCR reaction is performed using the Marathon cDNA (Clontech Laboratories Inc.) according to the manufacturer's instructions. The PCR program consists of 30 cycles of 94 degrees C. for 15 seconds, 60 degrees C. for 1 minute, 72 degrees C. for 2 minutes. The PCR products were cloned into pCR2.1 according to the manufacturers protocol (Invitrogen Corp.). The resulting plasmid was designated pCGN8538. The nucleic acid sequence and the derived amino acid sequence of the jojoba wax synthase is determined and shown in FIGS. 10 and 11, respectively.

Example 8

Generation of Transgenic Plants Containing the Wax Synthase cDNA

Figure 5B:
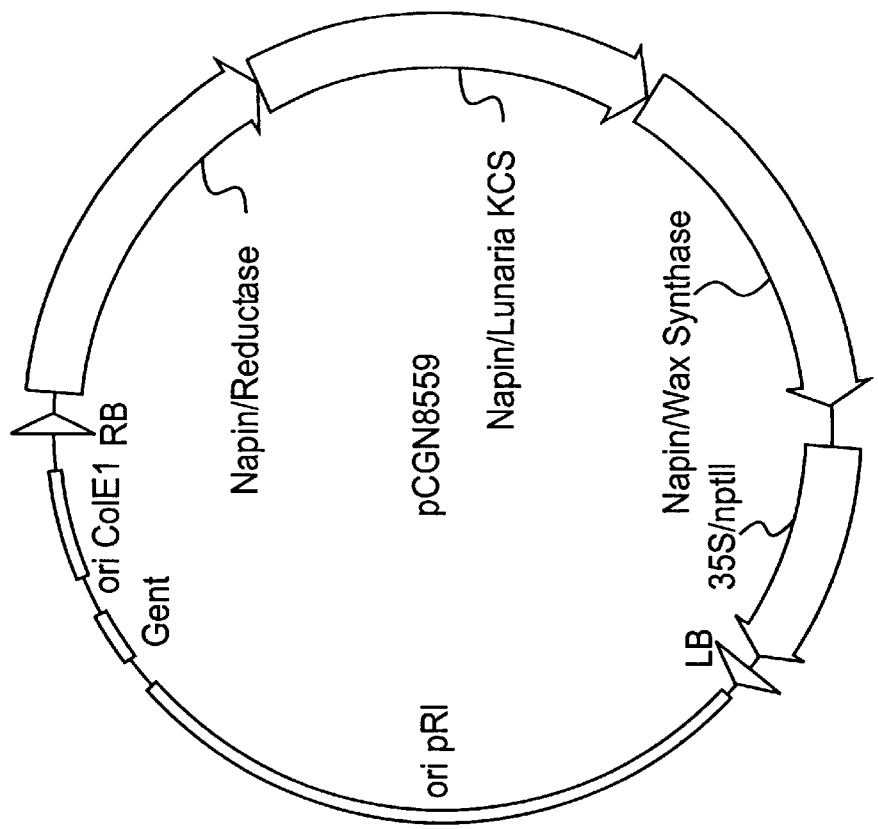
FIG. 5 provides schematic representations of the binary vectors pCGN8557 (FIG. 5A) and pCGN8559 (FIG. 5B).
Figure 5A:
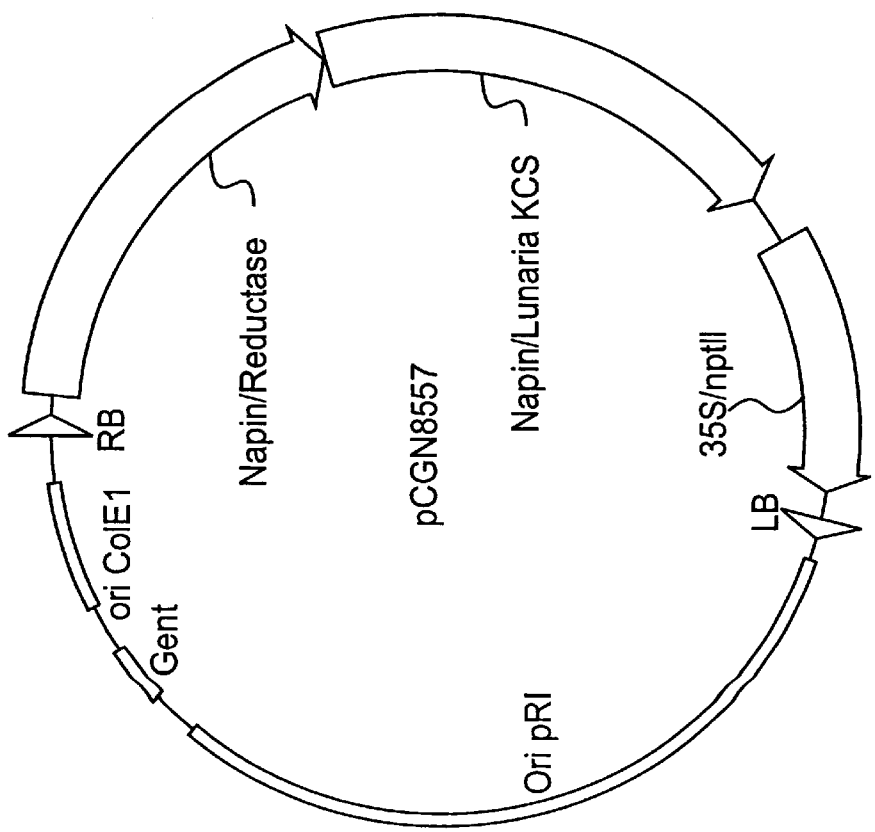

Two plant binary vectors were constructed. Plasmid pCGN8559 contains 3 genes necessary for wax biosynthesis: the condensing enzyme involved in fatty acid elongation to chain lengths greater than 18 carbons (KCS), the acyl-CoA reductase involved in formation of fatty alcohols, and the wax synthase. A control plasmid, pCGN8557, contains the KCS and acyl-CoA reductase genes. The Asp718 fragment of pCGN7698, which contains the jojoba acyl-CoA reductase under control of napin regulatory sequences, was cloned into the Asp718 site of binary vector pCGN5139 to form pCGN8555. The NotI fragment of pCGN7844, which contains the Lunaria KCS under control of napin regulatory sequences, was cloned into the NotI site of pCGN8555 to form pCGN 8557 (FIG. 5A). The SalI-BglII fragment from pCGN8538 which contains the coding region of the jojoba wax synthase gene, was cloned into the napin expression cassette of pCGN7770 digested with the same two restriction endonucleases to form pCGN8553. The Sse8387 fragment of pCGN8553, which contains the jojoba wax synthase under control of napin regulatory sequences, was cloned into the Sse8387 site of pCGN8557 to form pCGN8559 (FIG. 5B). The binary vectors were introduced into Agrobacterium tumefaciens EHA105 via electroporation. The vectors were used to transform *Arabidopsis thaliana* ecotype No-O according to the vacuum infiltration protocol of Bent et al. (1994, Science 265:1856–1860).

Example 9

Analysis of Developing Arabidopgig Seed

Figure 4:
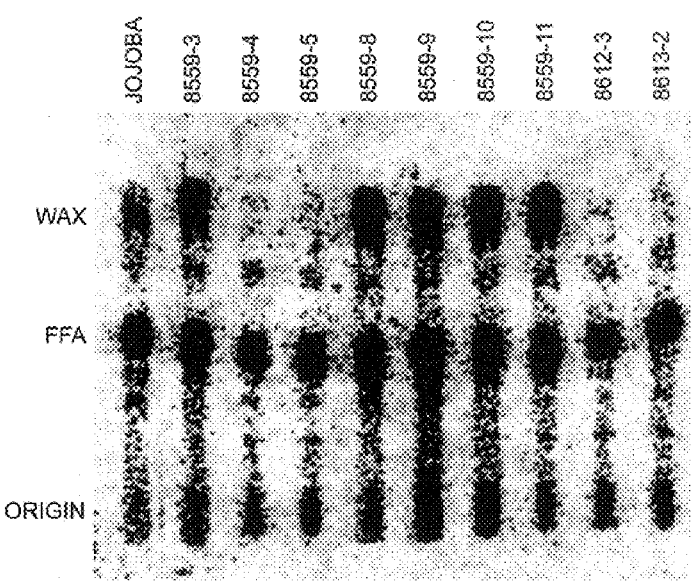
FIG. 4 provides the Radioimage of TLC plate showing incorporation of 1-$^{14}$C 16:0 CoA into wax in assays of the pellet fractions prepared from developing seeds of Arabidopsis transformed with pCGN8559. A membrane fraction from developing jojoba seed is the positive control. Background activity is illustrated in the assays of Arabidopsis plants 8612-3 and 8613-2.

Siliques were harvested from seven Arabidopsis plants transformed with pCGN8559 which were in various stages of development. Developing seed was removed from ten siliques collected from each plant and homogenized in 275 µl of buffer (100 mM HEPES/NaOH pH 7.5, 250 mM NaCl). A portion of the homogenate (200 µl) was centrifuged at 16000×g for 20 minutes at 4° C. resulting in a supernatant and pellet. The pellet was resuspended in 200 µl of the same buffer. The homogenate and the two fractions were assayed for wax synthase activity according to the protocol detailed in Example 1B. 25 µl of sample were used per assay in a final volume of 250 µl. The assay buffer contained 40 µM $1\text{-}^{14}C$ 16:0-CoA (specific activity 5 µCi/µmol), 200 µM 18:1 alcohol, 50 mM HEPES/NaOH pH 7.5, 250 mM NaCl and 2 mM β-mercaptoethanol. TLC analysis showed the incorporation of radiolabel from $1\text{-}^{14}C$ 16:0-CoA into a band which comigrated with a wax standard in 5 of the 7 plants analyzed (FIG. 4). This activity was detected in the homogenate and pellet fractions but not in the supernatant fraction. The wax synthase activity detected in these samples is several orders of magnitude greater than an endogenous wax synthase activity previously shown to be present in developing Arabidopsis seed. The activity detected in 8612-3 and 8613-2 is indicative of this endogenous "background" activity. A positive control for wax activity was the jojoba (DP2) membrane fraction.

Example 10

Analysis of the Seed Oil
A. Thin-layer Chromatographic Analysis

Figure 6:
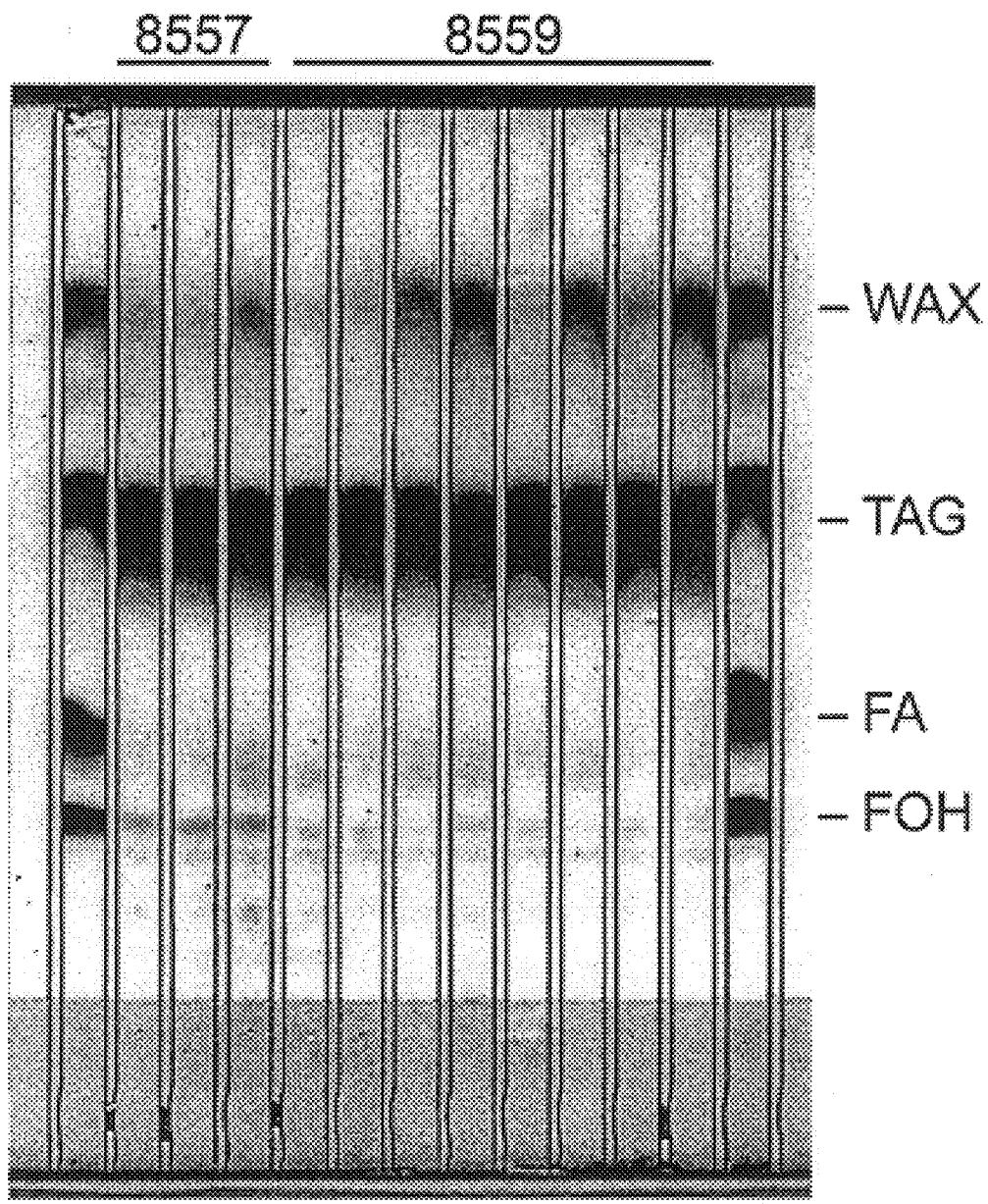
FIG. 6 provides the results of TLC of the production of wax in the seed oil of Arabidopsis plants containing the vectors pCGN8557 or pCGN8559.

Seeds from Arabidopsis plants were homogenized in hexane using a mortar and pestle. The hexane was transferred to a new vial and evaporated under nitrogen gas and the oil was resuspended in hexane at a concentration of 10 mg/ml. 10 µl of the oil solution was spotted on a silica gel-G TLC plate and the chromatogram was developed in hexane:diethyl ether:acetic acid (80:20:1). The lipids were stained with iodine. Elevated levels of wax were seen in the oil extracted from plants expressing pCGN8559 that also tested positive for wax synthase activity by assay. Intermediate levels of wax were detected in seeds from pCGN8557 which contained only reductase/KCS and low, background levels of wax were detected in Arabidopsis No-O controls (FIG. 6).

B. Gas Chromatographic Analysis

The oil in about 10 mg of Arabidopsis seed was derivatized to form fatty acid methyl esters (FAME) and free alcohol. The extractable lipid was analyzed for FAME and alcohol content by gas chromatography. Internal standard 17:0 TAG was spiked into the lipid fraction and derivatization was carried out at 90° C. in the presence of acidic methanol and toluene. Lipid products were extracted by adding hexane and 1M aqueous NaCl. The fatty acid methyl esters (FAME) and alcohols were separated on a 0.25 mm×15 m Supelcowax-10 column. Percent composition of the products was determined by their weight contribution to the sample (Table 3A). A correction factor for the Flame Ionization Detector (FID) response, determined experimentally to be 1.155, was used to adjust the quantitation of the alcohol peak relative to the 17:0 methyl ester standard. The weight composition was used to determine the percentage of very long chain carbon groups (>18C) present (Table 3B).

| A | Fatty Acyl Groups | | | | | | | | | | | | | |
|---|---|---|---|---|---|---|---|---|---|---|---|---|---|---|
| Sample | 16:0 | 16:1 | 18:0 | 18:1 | 18:2 | 18:3 | 20:0 | 20:1 | 20:2 | 22:0 | 22:1 | 22:2 | 24:0 | 24:1 |
| 8559-3 | 6.1 | 0.3 | 2.3 | 14.7 | 21.5 | 19.3 | 1.1 | 12.2 | 1.0 | 0.8 | 9.8 | 0.1 | 1.0 | 3.4 |
| 8559-4 | 6.1 | 0.3 | 2.8 | 17.5 | 25.1 | 18.9 | 2.2 | 22.1 | 1.9 | 0.3 | 2.4 | 0.1 | 0.1 | 0.2 |
| 8559-5 | 6.1 | 0.3 | 2.8 | 17.2 | 25.4 | 18.9 | 2.3 | 22.0 | 1.9 | 0.3 | 2.4 | 0.1 | 0.1 | 0.2 |
| 8559-6 | 6.0 | 0.3 | 2.7 | 17.9 | 25.4 | 18.9 | 2.2 | 21.7 | 1.9 | 0.3 | 2.4 | 0.1 | 0.1 | 0.2 |
| 8559-7 | 6.0 | 0.3 | 2.6 | 17.0 | 25.2 | 19.6 | 2.2 | 22.1 | 1.9 | 0.3 | 2.4 | 0.1 | 0.1 | 0.2 |
| 8559-8 | 5.9 | 0.3 | 2.2 | 14.9 | 21.4 | 18.7 | 1.1 | 13.5 | 1.1 | 0.7 | 8.7 | 0.2 | 0.6 | 2.0 |
| 8559-9 | 5.9 | 0.4 | 2.0 | 13.3 | 21.7 | 14.8 | 1.2 | 12.9 | 1.1 | 0.7 | 8.8 | 0.2 | 1.7 | 6.5 |
| 8559-10 | 5.7 | 0.4 | 1.9 | 13.5 | 20.6 | 19.0 | 1.0 | 10.7 | 0.9 | 0.8 | 10.1 | 0.2 | 1.3 | 5.5 |
| 8559-11 | 5.5 | 0.2 | 1.6 | 10.9 | 17.5 | 17.8 | 0.7 | 8.9 | 0.7 | 0.9 | 11.3 | 0.2 | 1.3 | 5.3 |
| 8559-13 | 6.1 | 0.3 | 2.8 | 16.8 | 24.3 | 18.8 | 2.1 | 19.4 | 1.6 | 0.5 | 5.3 | 0.1 | 0.4 | 1.3 |
| 8559-14 | 5.6 | 0.3 | 2.7 | 18.3 | 24.4 | 18.5 | 2.2 | 22.5 | 2.0 | 0.3 | 2.8 | 0.1 | 0.1 | 0.2 |
| 8559-15 | 6.1 | 0.5 | 1.8 | 12.6 | 20.8 | 16.4 | 1.0 | 11.8 | 1.0 | 0.8 | 9.4 | 0.2 | 1.1 | 4.5 |
| 8559-16 | 5.9 | 0.3 | 2.8 | 17.9 | 24.4 | 18.5 | 2.3 | 22.6 | 1.9 | 0.3 | 2.6 | 0.1 | 0.2 | 0.2 |
| 8559-17 | 5.8 | 0.3 | 2.5 | 16.7 | 23.2 | 18.9 | 1.7 | 17.2 | 1.4 | 0.6 | 7.3 | 0.1 | 0.5 | 2.3 |
| 8559-18 | 5.7 | 0.4 | 1.7 | 10.9 | 18.5 | 16.4 | 1.0 | 12.4 | 1.0 | 0.8 | 8.3 | 0.2 | 1.2 | 4.3 |
| 8557-1 | 5.6 | 0.3 | 2.4 | 16.6 | 22.5 | 19.6 | 1.5 | 15.4 | 1.3 | 0.6 | 8.0 | 0.2 | 0.5 | 2.7 |
| 8557-3 | 5.9 | 0.3 | 2.6 | 16.6 | 22.3 | 21.1 | 2.1 | 21.4 | 2.1 | 0.3 | 2.8 | 0.1 | 0.1 | 0.2 |

-continued

| | | | | | | | | | | | | | | |
|---|---|---|---|---|---|---|---|---|---|---|---|---|---|---|
| 8557-4 | 6.4 | 0.4 | 2.5 | 14.1 | 23.0 | 17.7 | 1.4 | 12.8 | 1.3 | 0.8 | 8.8 | 0.2 | 0.8 | 2.5 |
| 8557-5 | 5.6 | 0.2 | 2.3 | 13.6 | 21.9 | 21.8 | 1.1 | 11.3 | 1.3 | 0.8 | 10.9 | 0.2 | 0.7 | 3.2 |
| 8557-6 | 5.8 | 0.4 | 2.6 | 14.4 | 23.1 | 19.6 | 1.4 | 14.3 | 1.4 | 0.7 | 8.8 | 0.2 | 0.7 | 3.1 |
| 8557-7 | 5.5 | 0.3 | 2.4 | 13.7 | 23.2 | 21.0 | 1.6 | 17.4 | 1.7 | 0.6 | 8.9 | 0.2 | 0.5 | 2.8 |
| 8557-8 | 6.0 | 0.4 | 2.3 | 12.6 | 21.5 | 20.9 | 0.9 | 8.7 | 1.0 | 0.9 | 12.3 | 0.3 | 0.9 | 4.3 |
| 8557-9 | 5.6 | 0.3 | 2.4 | 14.4 | 22.5 | 21.7 | 1.2 | 12.6 | 1.3 | 0.7 | 10.5 | 0.2 | 0.6 | 3.1 |
| 8557-10 | 6.0 | 0.3 | 2.5 | 14.3 | 22.6 | 21.1 | 1.2 | 11.7 | 1.3 | 0.8 | 10.1 | 0.2 | 0.7 | 3.0 |
| 8557-11 | 6.0 | 0.4 | 2.5 | 13.2 | 22.4 | 19.5 | 1.2 | 11.8 | 1.2 | 0.8 | 10.1 | 0.2 | 0.9 | 3.8 |
| 8557-12 | 5.7 | 0.3 | 2.8 | 16.3 | 24.5 | 19.4 | 2.1 | 23.4 | 2.1 | 0.3 | 2.6 | 0.1 | 0.1 | 0.2 |
| 8557-13 | 6.1 | 0.3 | 2.5 | 13.3 | 22.3 | 21.2 | 1.1 | 11.2 | 1.2 | 0.8 | 10.6 | 0.2 | 0.7 | 3.0 |
| 8557-14 | 5.9 | 0.2 | 2.5 | 13.4 | 23.0 | 19.4 | 1.1 | 11.4 | 1.3 | 0.8 | 10.9 | 0.2 | 0.7 | 2.9 |
| N0-O-1 | 6.5 | 0.4 | 3.1 | 15.6 | 26.3 | 17.7 | 2.7 | 22.1 | 2.1 | 0.4 | 2.6 | 0.2 | 0.2 | 0.2 |
| N0-O-2 | 6.4 | 0.4 | 3.1 | 15.6 | 26.2 | 17.9 | 2.7 | 22.0 | 2.1 | 0.4 | 2.6 | 0.2 | 0.2 | 0.2 |
| N0-O-3 | 6.4 | 0.4 | 3.1 | 15.6 | 26.3 | 17.6 | 2.7 | 22.1 | 2.1 | 0.4 | 2.6 | 0.2 | 0.2 | 0.2 |

| | A | Fatty Alcohols | | | B VLCFA |
|---|---|---|---|---|---|
| Sample | OH18:1 | OH20:1 | OH22:1 | OH24:1 | wt % |
| 8559-3 | 0.1 | 0.5 | 3.3 | 2.4 | 35.7 |
| 8559-4 | 0.0 | 0.0 | 0.0 | 0.0 | 29.4 |
| 8559-5 | 0.0 | 0.0 | 0.0 | 0.0 | 29.3 |
| 8559-6 | 0.0 | 0.0 | 0.0 | 0.0 | 28.8 |
| 8559-7 | 0.0 | 0.0 | 0.0 | 0.0 | 29.4 |
| 8559-8 | 0.1 | 1.0 | 5.3 | 2.2 | 36.5 |
| 8559-9 | 0.1 | 0.4 | 3.8 | 4.4 | 42.0 |
| 8559-10 | 0.0 | 0.5 | 4.2 | 3.6 | 38.9 |
| 8559-11 | 0.2 | 1.1 | 9.3 | 6.5 | 46.5 |
| 8559-13 | 0.0 | 0.1 | 0.1 | 0.1 | 31.0 |
| 8559-14 | 0.0 | 0.0 | 0.0 | 0.0 | 30.2 |
| 8559-15 | 0.2 | 0.8 | 6.7 | 4.3 | 41.9 |
| 8559-16 | 0.0 | 0.0 | 0.0 | 0.0 | 30.2 |
| 8559-17 | 0.0 | 0.2 | 0.7 | 0.5 | 32.5 |
| 8559-18 | 0.0 | 1.3 | 9.9 | 5.9 | 46.4 |
| 8557-1 | 0:0 | 0.1 | 1.1 | 1.5 | 33.0 |
| 8557-3 | 0.0 | 1.8 | 0.2 | 0.0 | 31.1 |
| 8557-4 | 0.0 | 0.3 | 2.9 | 4.2 | 35.9 |
| 8557-5 | 0.0 | 0.2 | 2.1 | 2.8 | 34.6 |
| 8557-6 | 0.0 | 0.1 | 1.3 | 2.1 | 34.1 |
| 8557-7 | 0.0 | 0.0 | 0.1 | 0.2 | 34.0 |
| 8557-8 | 0.0 | 0.2 | 2.6 | 4.0 | 36.2 |
| 8557-9 | 0.0 | 0.1 | 1.2 | 1.4 | 33.1 |
| 8557-10 | 0.0 | 0.2 | 1.9 | 2.4 | 33.3 |
| 8557-11 | 0.0 | 0.2 | 2.2 | 3.6 | 36.0 |
| 8557-12 | 0.0 | 0.0 | 0.0 | 0.0 | 30.9 |
| 8557-13 | 0.0 | 0.2 | 2.1 | 3.0 | 34.2 |
| 8557-14 | 0.0 | 0.2 | 2.7 | 3.2 | 35.5 |
| No-O-1 | 0.0 | 0.0 | 0.0 | 0.0 | 30.5 |
| No-O-2 | 0.0 | 0.0 | 0.0 | 0.0 | 30.4 |
| No-O-3 | 0.0 | 0.0 | 0.0 | 0.0 | 30.6 |

C. $^{13}$C-NMR Analysis of Intact Arabidopsis Seed

Figure 7:
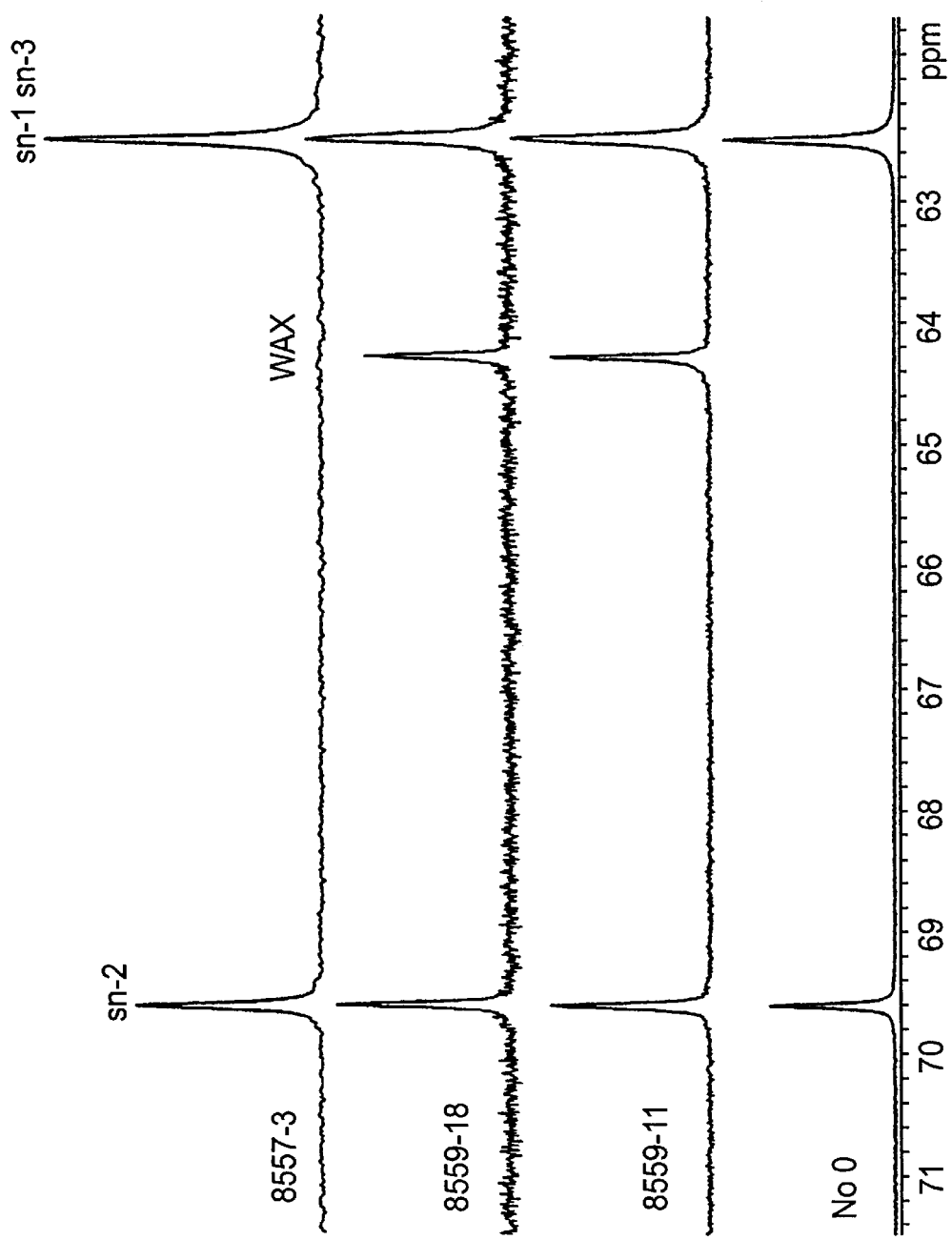
FIG. 7 provides the results of 13C-NMR spectra analysis of intact mature Arabidopsis seed containing either pCGN8557 or pCGM8559.

TLC analysis showed that plants expressing pCGN8559 did not contain any free alcohol therefore the alcohol peak present in the transmethylated samples was likely due to the derivatization of wax present in the seed oil. Based on this evidence it is estimated the amount of wax in plants expressing pCGN8559 at twice the weight of the alcohol detected by gas chromatography (Table 4A). This was not the case for plants expressing pCGN8557 where both alcohol and wax spots were visible by TLC after exposure to iodine vapor. In order to find a more direct measure of the amount of wax present, $^{13}$C-NMR spectra is obtained for intact mature Arabidopsis seed to determine the molar ratio of wax and TAG. A region of the spectra between 60–70 ppm was identified as containing unique carbon shifts for the sn-2 carbon of the glycerol backbone at 69.5 ppm, representing the molar amount of TAG, and the first carbon on the alcohol side of the wax ester linkage at 64.2 ppm, representing the molar amount of wax (FIG. 7). Ratios of these two unique carbons were determined. From these ratios the mole percent wax was calculated (Table 4B). The mole percent data was converted to weight percent data using the following conversion:

Wt %=100*(mole %wax*molecular weight wax) (mole %wax*MW wax)+[(100–mole %wax)*MW TAG)]

The molecular weight of wax and TAG was assigned as 20:1—20:1 wax and tri 20:1 TAG.

Figure 8:
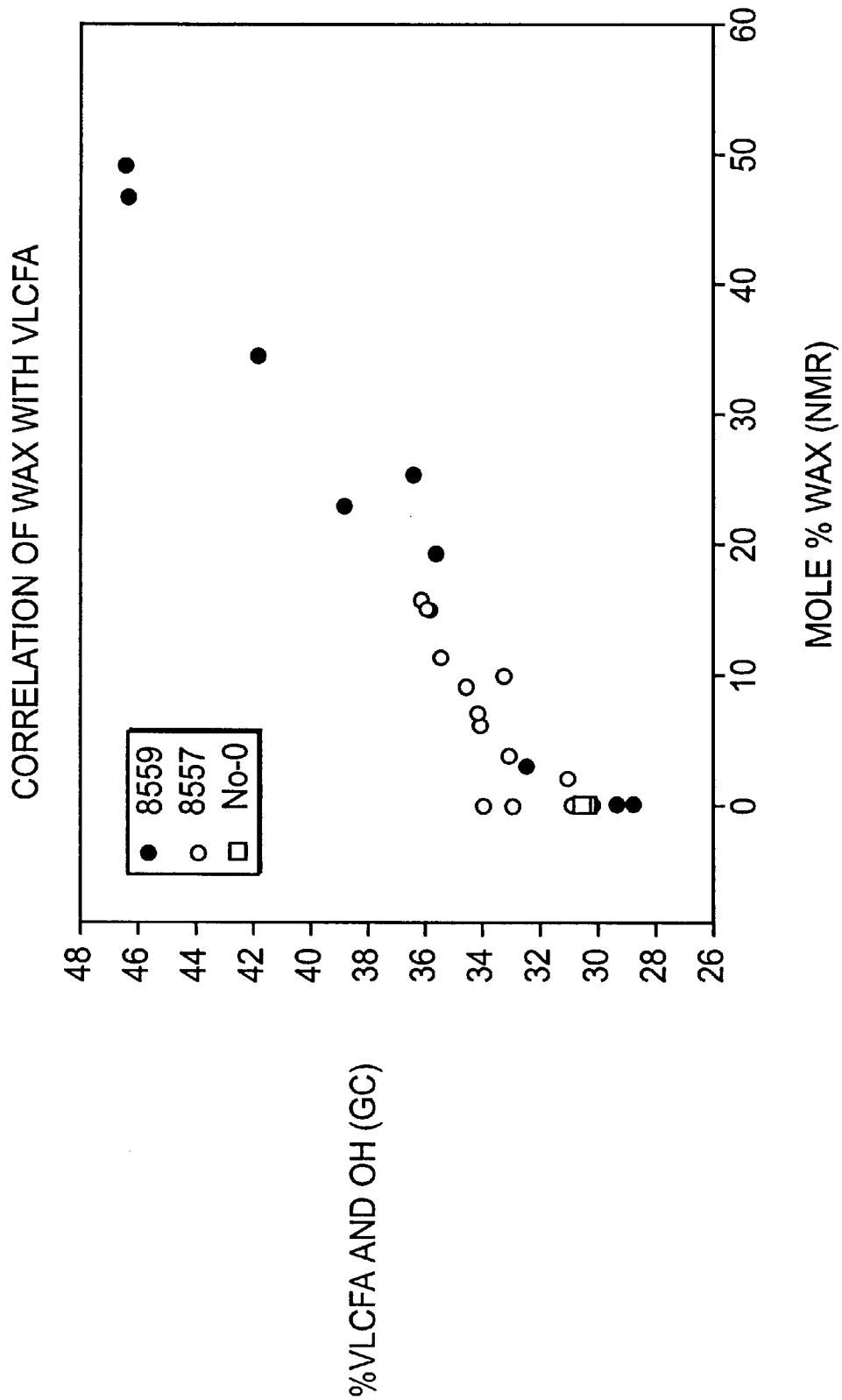
FIG. 8 provides a graph representing the contribution of wax synthase to the production of very long chain fatty acids.

The weight percent of wax calculated by the GC method was in agreement with the weight percent wax determined by the nondestructive measurement using $^{13}$C-NMR. Using this method a determination of the mole percent wax present in the plants expressing pCGN8557 is obtained. A calculation of the contribution of wax synthase to the production of very long chain fatty acids (VLCFAs) is shown in FIG. 8.

TABLE 4

| Sample | GC wt % OH | GC wt % wax | NMR wt % wax | Wax mole % wax |
|---|---|---|---|---|
| 8559-3 | 6.2 | 12.4 | 12.8 | 19.4 |
| 8559-4 | 0.0 | 0.0 | 0.0 | 0.0 |
| 8559-5 | 0.0 | 0.0 | 0.0 | 0.0 |

TABLE 4-continued

| Sample | GC wt % OH | GC wt % wax | NMR wt % wax | Wax mole % wax |
|---|---|---|---|---|
| 8559-6 | 0.0 | 0.0 | 0.0 | 0.0 |
| 8559-7 | 0.0 | 0.0 | 0.0 | 0.0 |
| 8559-8 | 8.6 | 17.1 | 17.2 | 25.4 |
| 8559-9 | 8.7 | 17.5 | nd | nd |
| 8559-10 | 8.4 | 16.7 | 15.5 | 23.1 |
| 8559-11 | 17.1 | 34.1 | 37.2 | 49.2 |
| 8559-13 | 0.3 | 0.5 | nd | nd |
| 8559-14 | 0.0 | 0.0 | nd | nd |
| 8559-15 | 12.0 | 24.1 | 24.4 | 34.6 |
| 8559-16 | 0.0 | 0.0 | 0.0 | 0.0 |
| 8559-17 | 1.4 | 2.8 | 1.9 | 3.0 |
| 8559-18 | 17.2 | 34.3 | 34.9 | 46.8 |
| 8557-1 | 2.7 | — | nd | nd |
| 8557-3 | 2.0 | — | 1.2 | 2.0 |
| 8557-4 | 7.4 | — | 9.9 | 15.3 |
| 8557-5 | 5.1 | — | 5.8 | 9.1 |
| 8557-6 | 3.6 | — | 3.8 | 6.0 |
| 8557-7 | 0.2 | — | 0.0 | 0.0 |
| 8557-8 | 6.8 | — | 10.4 | 16.0 |
| 8557-9 | 2.8 | — | 2.4 | 3.8 |
| 8557-10 | 4.4 | — | 6.3 | 9.9 |
| 8557-11 | 6.0 | — | 9.9 | 15.3 |
| 8557-12 | 0.0 | — | 0.0 | 0.0 |
| 8557-13 | 5.4 | — | 4.4 | 7.0 |
| 8557-14 | 6.1 | — | 7.4 | 11.5 |
| No-O-1 | 0.0 | — | 0.0 | |
| No-O-2 | 0.0 | — | 0.0 | |
| No-O-3 | 0.0 | — | nd | |

Example 11

Analysis of Transgenic Arabidopsis Leaves

Figure 9:
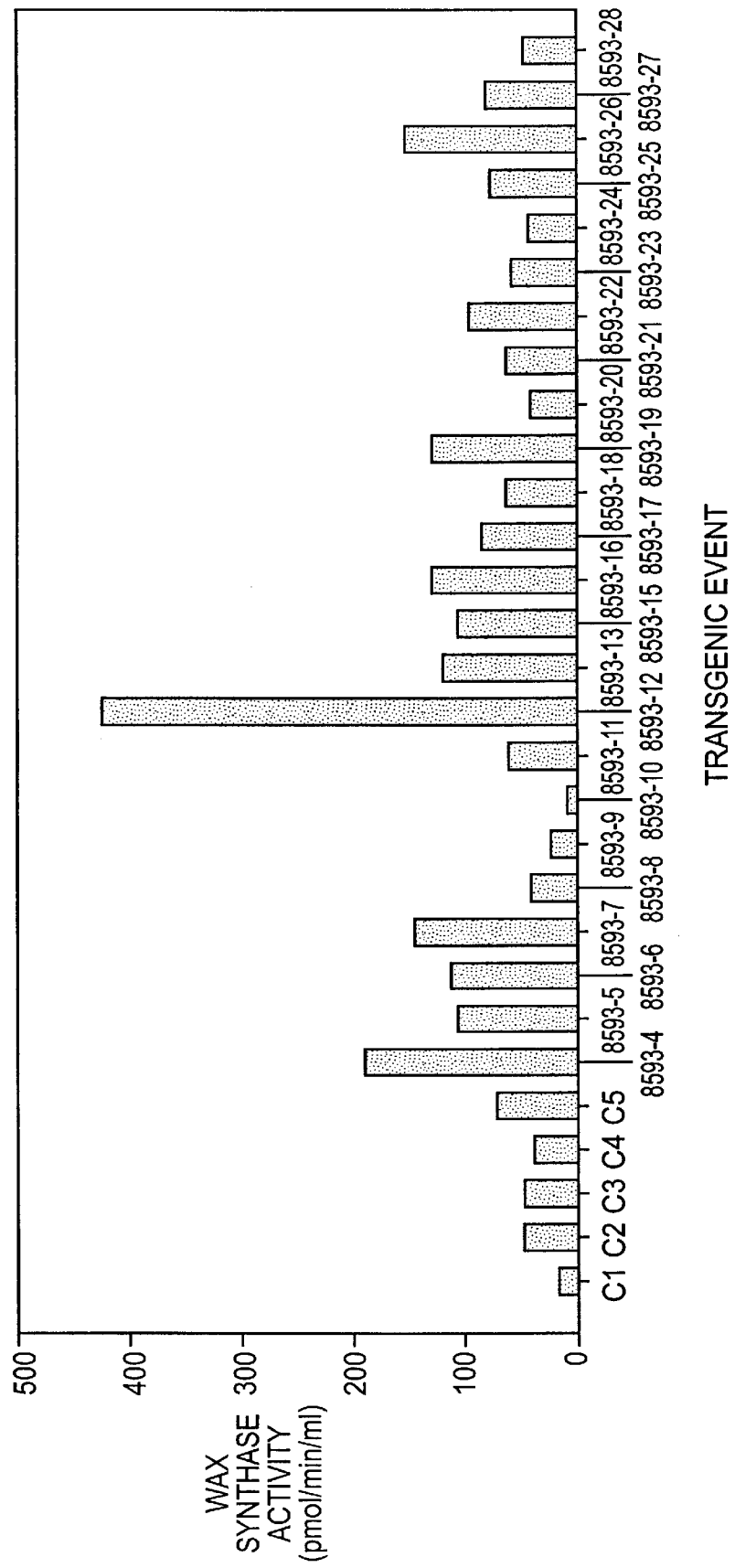
FIG. 9 provides wax synthase activity results from various transgenic Arabidopsis lines containing pCGN8593.

Rosette leaves from plants transformed with construct pCGN 8593, expressing wax synthase under the control of the 35S promoter, were analyzed for wax synthase activity. Leaves were homogenized in 200 μl homogenization buffer (100 mM Tricine/NaOH, pH 7.8, 280 mM NaCl, 10% glycerol, and protease inhibitors 0.1 μM Aprotinin, 1 μM Leupeptin, and 100 μM Pefabloc) and the solids were pelleted by centrifugation at 16,000×g for 10 min and 4° C. The supernatant was removed and the pellet resuspended in 200 μl homogenization buffer. This fraction was referred to as the P1 fraction. Five control leaves harvested from Arabidopsis cultivar No-O were assayed as controls. The P1 fractions were assayed for wax synthase activity as described in Example 1B. Wax synthase activity in the plants expressing pCGN8593 was compared with the average activity found in the No-O controls. Eleven of the 24 plants analyzed demonstrated activity more than twice the average background level found in No-O (FIG. 9). One plant demonstrated nearly a 10-fold increase in activity.

Example 12

Identification of Additional Wax Synthase Sequences

Figure 19A:
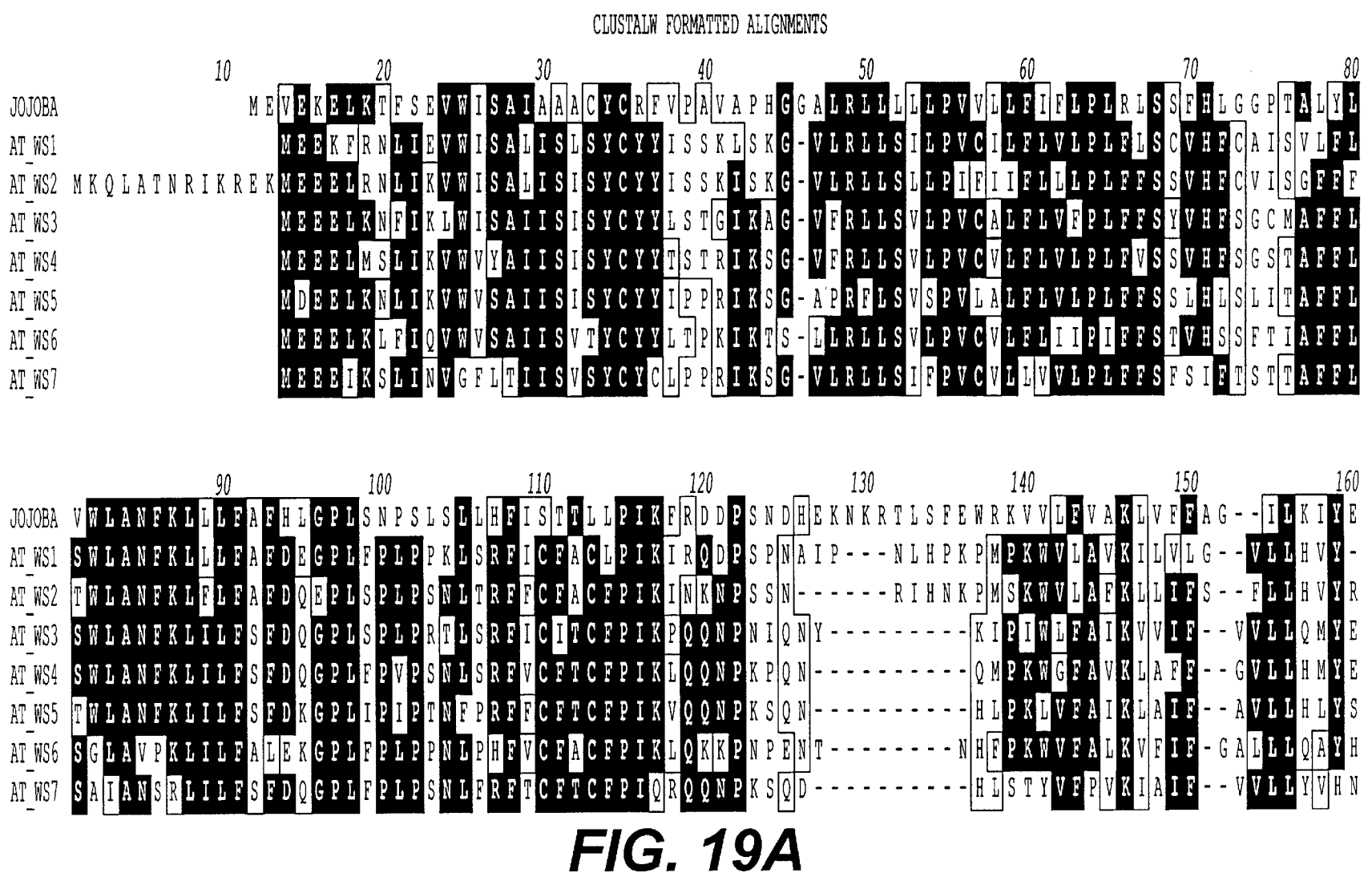
Figure 19B:
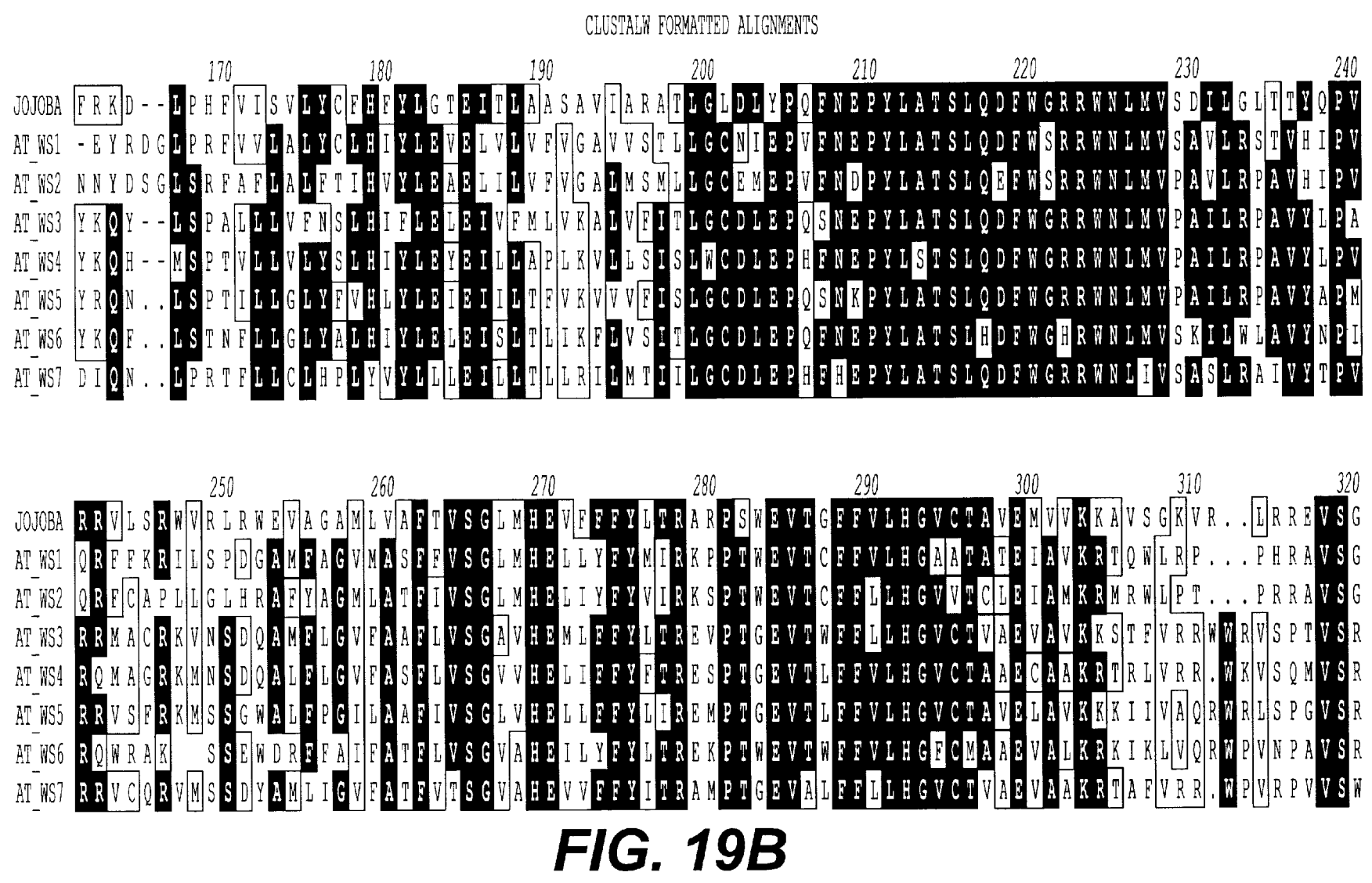
Figure 19C:
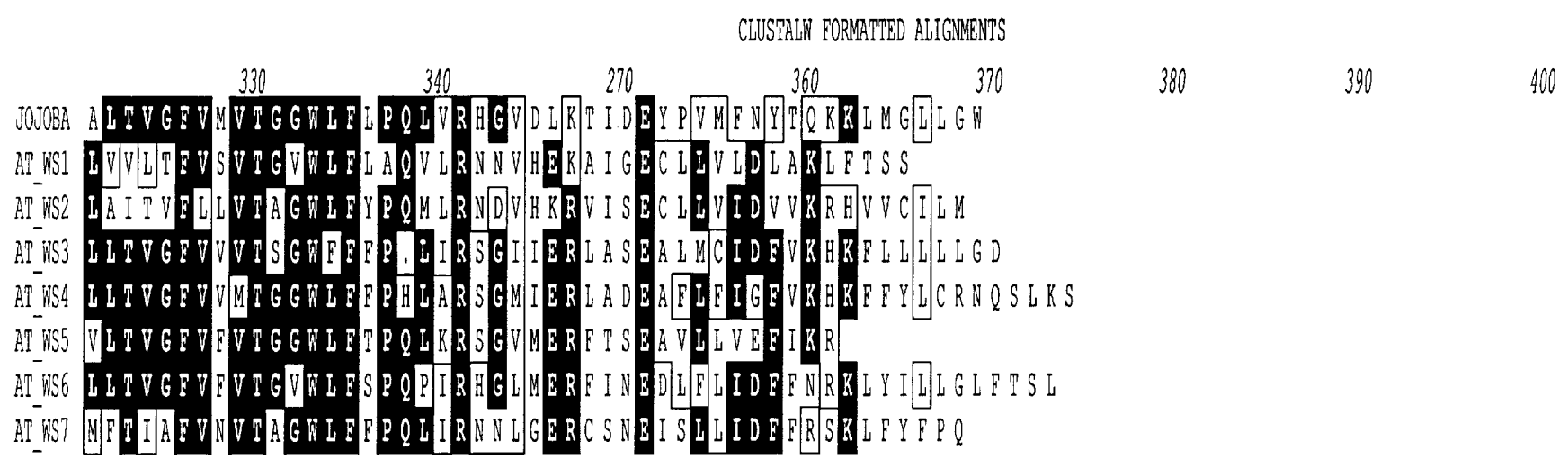

The protein sequence of the jojoba wax synthase (FIG. 11) is used to query the Arabidopsis DNA sequence database (http://genome-www.stanford.edu/Arabidopsis/). One of the accessions, P1 clone MTE17(Genbank accession AB015479), contains 7 repeats of open reading frames with similarity to the jojoba wax synthase. The open reading frames have been designated ATWS1 to ATWS7 (FIGS. 12–18, respectively). They are found between nucleotides 23670 and 11479 of MTE17 using the numbering system of the Genbank entry. The inferred protein sequences are aligned with the jojoba wax synthase sequence (FIG. 19) and a dendogram (FIG. 20) of their relationships is constructed using the Clustal W algorithm of MacVector 6.5 (Oxford Molecular). The sequence alignment in FIG. 19 shows a series of peptide sequences which are conserved between the amino acid sequences (Table 5). The percent identities and similarities are also determined, and are presented in table 6.

TABLE 5

| | SEQUENCE | SEQ ID NO: |
|---|---|---|
| 1 | LXLF(A/S)(F/L)XX(G/E) | 24 |
| 2 | PYL(A/S)TSL(Q/H)(D/E)FW(G/S)(R/H)RWNL(M/I)V | 25 |
| 3 | FX(V/T)SGXXHEXX(F/Y)FYX(I/T)R | 26 |
| 4 | P(S/T)(W/G)EV(T/A)XFF(V/L)LHG | 27 |

TABLE 6

| SEQUENCES COMPARED | PERCENT IDENTITY | PERCENT SIMILARITY |
|---|---|---|
| JoWS vs ATWS1 | 41% | 17% |
| JoWS vs ATWS2 | 37% | 19% |
| JoWS vs ATWS3 | 42% | 15% |
| JoWS vs ATWS4 | 42% | 16% |
| JoWS vs ATWS5 | 44% | 13% |
| JoWS vs ATWS6 | 41% | 17% |
| JoWS vs ATWS7 | 36% | 16% |
| ATWS3 vs ATWS6 | 59% | 14% |
| ATWS3 vs ATWS1 | 49% | 17% |
| ATWS3 vs ATWS4 | 71% | 10% |
| ATWS3 vs ATWS7 | 55% | 15% |
| ATWS3 vs ATWS2 | 49% | 21% |
| ATWS3 vs ATWS5 | 64% | 14% |
| ATWS6 vs ATWS1 | 47% | 18% |
| ATWS6 vs ATWS4 | 57% | 15% |
| ATWS6 vs ATWS7 | 51% | 17% |
| ATWS6 vs ATWS2 | 45% | 18% |
| ATWS6 vs ATWS5 | 57% | 15% |
| ATWS1 vs ATWS4 | 52% | 17% |
| ATWS1 vs ATWS7 | 46% | 19% |
| ATWS1 vs ATWS2 | 65% | 12% |
| ATWS1 vs ATWS5 | 49% | 17% |
| ATWS4 vs ATWS7 | 58% | 13% |
| ATWS4 vs ATWS2 | 50% | 19% |
| ATWS4 vs ATWS5 | 65% | 13% |
| ATWS7 vs ATWS2 | 45% | 18% |
| ATWS7 vs ATWS5 | 55% | 16% |
| ATWS2 vs ATWS5 | 49% | 17% |

Complementary DNA (cDNA) is constructed from Arabidopsis RNA isolated from immature seeds, whole seedlings (vegetative tissue), and inflorescences (flowers and flower stalks) using the SMART PCR cDNA Library construction kit according to the manufacturer's protocol (Clontech). SMART cDNA is also constructed from RNA from Brassica napus leaves, and immature seeds harvested at 15 days after pollination (DAP), 18 DAP, and 30 DAP. The SMART cDNAs are used for virtual Northern analysis, according to the protocol in the SMART cDNA manual from Clontech, of expression of the Arabidopsis ATWS cDNAs. ATWS2 is most highly expressed in Arabidopsis immature seeds and Brassica 30 DAP seeds. Expression is not detected in Brassica leaves or Arabidopsis seedlings. This is an expression pattern consistent with that expected for DAGAT, since triglycerides are primarily formed in developing seeds of these plants.

Example 13

Expression Constructs for AT-WS Homologues

To characterize the Arabidopsis sequence which is preferentially expressed in the developing seeds, constructs are prepared to direct the expression of the sequence in host plant cells.

A plasmid containing the napin cassette derived from pCGN3223 (described in U.S. Pat. No. 5,639,790, the entirety of which is incorporated herein by reference) was modified to make it more usefill for cloning large DNA fragments containing multiple restriction sites, and to allow the cloning of multiple napin fusion genes into plant binary transformation vectors. An adapter comprised of the self annealed oligonucleotide of sequence 5'-CGCGATT-TAAATGGCGCGCCCTGCAGGCGGCCGCCTGC-AGGGCGCGCCATTTAAAT (SEQ ID NO: 28) was ligated into the cloning vector pBC SK+(Stratagene) after digestion with the restriction endonuclease BssHII to construct vector pCGN7765. Plasmids pCGN3223 and pCGN7765 were digested with NotI and ligated together. The resultant vector, pCGN7770, contains the pCGN7765 backbone with the napin seed specific expression cassette from pCGN3223.

The cloning cassette, pCGN7787, essentially the same regulatory elements as pCGN7770, with the exception of the napin regulatory regions of pCGN7770 have been replaced with the double CAMV 35S promoter and the tml1 polyadenylation and transcriptional termination region.

A binary vector for plant transformation, pCGN5139, was constructed from pCGN1558 (McBride and Summerfelt, (1990) Plant Molecular Biology, 14:269–276). The polylinker of pCGN1558 was replaced as a HindIII/Asp718 fragment with a polylinker containing unique restriction endonuclease sites, AscI, PacI, XbaI, SwaI, BamHI,and NotI. The Asp718 and HindIII restriction endonuclease sites are retained in pCGN5139.

A series of turbo binary vectors are constructed to allow for the rapid cloning of DNA sequences into binary vectors containing transcriptional initiation regions (promoters) and transcriptional termination regions.

The plasmid pCGN8618 was constructed by ligating oligonucleotides 5'-TCGAGGATCCGCGGCCGCAAGC-TTCCTGCAGG-3' (SEQ ID NO: 29) and 5'-TCGACCTGCAGGAAGCTTGCGGCCGCGGATCC-3' (SEQ ID NO: 30) into SalI/XhoI-digested pCGN7770. A fragment containing the napin promoter, polylinker and napin 3' region was excised from pCGN8618 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8622.

The plasmid pCGN8619 was constructed by ligating oligonucleotides 5'-TCGACCTGCAGGAAGCTTGCGG-CCGCGGATCC-3' (SEQ ID NO: 31) and 5'-TCGAGGATCCGCGGCCGCAAGCTTCCTGCAGG -3' (SEQ ID NO: 32) into SalI/XhoI-digested pCGN7770. A fragment containing the napin promoter, polylinker and napin 3' region was removed from pCGN8619 by digestion with Asp7l8I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8623.

The plasmid pCGN8620 was constructed by ligating oligonucleotides 5'-TCGAGGATCCGCGGCCGCAAG-CTTCCTGCAGGAGCT-3' (SEQ ID NO: 33) and 5'-CCTGCAGGAAGCTTGCGGCCGCGGATCC -3' (SEQ ID NO: 34) into SalI/SacI-digested pCGN7787. A fragment containing the d35S promoter, polylinker and tml 3' region was removed from pCGN8621 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8624.

The plasmid pCGN8621 was constructed by ligating oligonucleotides 5'-TCGACCTGCAGGAAGCTTGC-GGCCGCGGATCCAGCT-3' (SEQ ID NO: 35) and 5'-GGATCCGCGGCCGCAAGCTTCCTGCAGG-3' (SEQ ID NO: 36) into SalI/SacI-digested pCGN7787. A fragment containing the d35S promoter, polylinker and tml 3' region was removed from pCGN8621 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8625.

The open reading frame of AT-WS2 was PCR amplified from Arabidopsis genomic DNA using the primers 5'-GGATCCGCGGCCGCATTATGAAACAGTTAGCAA-CCAACAG-3' (SEQ ID NO: 37) and 5'-GGATCC-CCTGCAGGTTACATTAAAATACAGACAACGTGCC-3' (SEQ ID NO: 38). The PCR product is cloned into plasmid pCR 2.1 according to the manufacturer's protocol (Clontech) to generate the plasmid pCGN9706. To direct transcription of a sense transcript under control of a napin expression cassette in transgenic plants, plasmid pCGN9712 is constructed by cloning the NotI/Sse8387I fragment from pCGN9706 into NotI/PstI digested binary vector pCGN8622. To direct transcription of an antisense transcript under control of a napin expression cassette in transgenic plants, plasmid pCGN9713 was constructed by cloning the NotI/Sse8387I fragment from pCGN9706 into NotI/PstI digested binary vector pCGN8623. To direct transcription of a sense transcript under control of a double 35S expression cassette in transgenic plants, plasmid pCGN9714 was constructed by cloning the NotI/Sse8387I fragment from pCGN9706 into NotI/PstI digested binary vector pCGN8624. Plasmids pCGN9712, pCGN9713, and pCGN9714 were introduced into Agrobacterium tumefaciens EHA105 by electroporation, and the resultant Agrobacterium strains were used to transform *Arabidopsis thaliana* plants by vacuum infiltration.

Example 14

Plant Transformation Methods and Analyses

A variety of methods have been developed to insert a DNA sequence of interest into the genome of a plant host to obtain the transcription or transcription and translation of the sequence to effect phenotypic changes.

High erucic acid varieties, such as cultivar Reston, or Canola-type varieties of *Brassica napus* may be transformed using Agrobacterium mediated transformation methods as described by Radke et al. (*Theor. Appl. Genet.* (1988) 75:685–694; *Plant Cell Reports* (1992) 11:499–505). Transgenic *Arabidopsis thaliana* plants may be obtained by Agrobacterium-mediated transformation as described by Valverkens et al., (*Proc. Nat. Acad. Sci.* (1988) 85:5536–5540), or as described by Bent et al. ((1994), *Science* 265:1856–1860), or Bechtold et al. ((1993), *C.R.Acad.Sci, Life Sciences* 316:1194–1199). Other plant species may be similarly transformed using related techniques.

Alternatively, microprojectile bombardment methods, such as described by Klein et al. (*Bio/Technology* 10:286–291) may also be used to obtain transformed plants comprising the reductase and wax synthase expression constructs described herein.

Seeds or other plant material from transformed plants may be analyzed for wax synthase activity using the wax synthase assay methods described in Example 1.

The above results demonstrate nucleic acid sequences obtained from partially purified wax synthase proteins are active in the formation of wax esters from fatty alcohol and fatty acyl substrates. Methods to obtain the wax synthase proteins and amino acid sequences thereof are provided. Such nucleic acid sequences may be manipulated to provide for transcription of the sequences and/or expression of wax synthase proteins in host cells, which proteins may be used for a variety of applications. Such applications include the production of wax ester compounds when the wax synthase is used in host cells having a source of fatty alcohol substrates, which substrates may be native to the host cells or supplied by use of recombinant constructs encoding a fatty acyl reductase protein which is active in the formation of alcohols from fatty acyl substrates.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. A recombinant DNA construct comprising a nucleic acid sequence which encodes the amino acid sequence of SEQ ID NO: 42.

2. An isolated polynucleotide comprising a nucleic acid sequence which encodes the amino acid sequence of SEQ ID NO: 42.

* * * * *